United States Patent
Prakash et al.

(10) Patent No.: US 11,766,486 B2
(45) Date of Patent: *Sep. 26, 2023

(54) METHODS OF DELIVERING ANIONIC AGENTS IN VIVO USING NON-VIRAL NANOPARTICLE-BASED DELIVERY SYSTEMS

(71) Applicant: NANORA PHARMA INC., Montreal (CA)

(72) Inventors: Satya Prakash, Brossard (CA); Meenakshi Malhotra, Montreal (CA)

(73) Assignee: NANORA PHARMA INC., Montreal (CA)

(\*) Notice: Subject to any disclaimer, the term of this patent is extended or adjusted under 35 U.S.C. 154(b) by 270 days.

This patent is subject to a terminal disclaimer.

(21) Appl. No.: 17/069,701

(22) Filed: Oct. 13, 2020

(65) Prior Publication Data
US 2021/0106695 A1 Apr. 15, 2021

Related U.S. Application Data

(63) Continuation of application No. 16/218,347, filed on Dec. 12, 2018, now Pat. No. 10,799,601, which is a (Continued)

(51) Int. Cl.
*A61K 9/51* (2006.01)
*A61K 48/00* (2006.01)
(Continued)

(52) U.S. Cl.
CPC .......... *A61K 48/0008* (2013.01); *A61K 47/60* (2017.08); *A61K 47/61* (2017.08); (Continued)

(58) Field of Classification Search
None
See application file for complete search history.

(56) References Cited

U.S. PATENT DOCUMENTS 6,602,952 B1 8/2003 Bentley et al.
6,958,325 B2 10/2005 Domb
(Continued)

OTHER PUBLICATIONS

Bozkir et al, "Chitosan Nanoparticles for Plasmid DNA Delivery: Effect of Chitosan Molecular Structure on Formulation and Release Characteristics" Drug Delivery, 2004, v 11, n 2, p. 107-112.
(Continued)

*Primary Examiner* — Kevin S Orwig
(74) *Attorney, Agent, or Firm* — Greer, Burns & Crain, LTD.; Gregory P. Einhorn

(57) ABSTRACT

The present invention concerns a polymeric material for the production of a non-viral nanoparticle. The polymeric material comprises (i) a hydrophilic linear polymer having a first end and a second end, (iii) a cross-linkable cationic polymer covalently bonded to the first end of the hydrophilic linear polymer, and (iii) at least one targeting/penetrating peptide covalently associated to the second end of the hydrophilic linear polymer. Also disclosed herein are nanoparticles produced with these polymeric material, processes for making the polymeric material and the nanoparticles as well as use of the nanoparticles.

13 Claims, 22 Drawing Sheets
Specification includes a Sequence Listing.

Related U.S. Application Data continuation of application No. 15/335,408, filed on Oct. 26, 2016, now abandoned, which is a continuation of application No. 13/916,941, filed on Jun. 13, 2013, now abandoned.

(60) Provisional application No. 61/660,139, filed on Jun. 15, 2012.

(51) Int. Cl.

| | |
|---|---|
| *C12N 15/88* | (2006.01) |
| *C12N 15/11* | (2006.01) |
| *A61K 47/69* | (2017.01) |
| *A61K 47/61* | (2017.01) |
| *A61K 47/60* | (2017.01) |

(52) U.S. Cl.
CPC ...... *A61K 47/6913* (2017.08); *A61K 47/6935* (2017.08); *A61K 47/6939* (2017.08); *A61K 48/0041* (2013.01); *C12N 15/111* (2013.01); *C12N 15/88* (2013.01); *C12N 2310/14* (2013.01); *C12N 2320/32* (2013.01); *C12N 2810/6054* (2013.01); *C12N 2810/851* (2013.01)

(56) References Cited

U.S. PATENT DOCUMENTS

| | | | |
|---|---|---|---|
| 7,772,382 | B2 | 8/2010 | Okamoto et al. |
| 7,803,351 | B2 | 9/2010 | Sharma et al. |
| 8,420,802 | B2 | 4/2013 | Jardine et al. |
| 8,431,543 | B2 | 4/2013 | Park et al. |
| 2004/0071654 | A1 | 4/2004 | Anderson et al. |
| 2004/0156904 | A1 | 8/2004 | Saltman et al. |
| 2006/0093674 | A1 | 5/2006 | Slobodkin et al. |
| 2008/0085242 | A1 | 4/2008 | Artursson et al. |
| 2009/0110719 | A1 | 4/2009 | Roy et al. |
| 2010/0113559 | A1 | 5/2010 | Park et al. |
| 2014/0141094 | A1 | 5/2014 | Smyth et al. |

OTHER PUBLICATIONS

Mao et al, "Chitosan-DNA nanoparticles as gene carriers: synthesis, characterization and transfection efficiency" Journal of Controlled Release, 2001, v 70, p. 399-421.
Kurita et al, "Chemoselective Protection of the Amino Groups of Chitosan by Controlled Phthaloylation: Facile Preparation of a Precursor Useful for Chemical Modifications" Bio Macromolecules, 2002, v 3, n 1.
Ifuku et al, "Preparation of highly chemoselective N-phthaloyl chitosan in aqueous media" Green Chemistry, 2011, v 13, p. 1499-1502.
Goosen, "Applications of Chitan and Chitosan" Technology & Engineering, 1996, p. 108-112.
Calvo,P, Remunan-Lopez,C, Vila-Jato,JL, Alonso,MJ: Novel hydrophilic chitosan-polyethylene oxide nanoparticles as protein carriers. J Appl Polym Sci 63:125-132, 1997.
Kurita K, Ikeda H, Yoshida Y, Shimojoh M, Harata M: Chemoselective protection of the amino groups of chitosan by controlled phthaloylation: facile preparation of a precursor useful for chemical modifications. Biomacromolecules 3:1-4, 2002.
Lin WJ, Chen MH: Synthesis of multifunctional chitosan with galactose as a targeting ligand for glycoprotein receptor. Carbohydrate polymers 67:474-480, 2007.
Malhotra,M, Kulamarva,A, Sebak,S, Paul ,A, Bhathena,J, Mirzaei,M, Prakash,S: Ultrafine chitosan nanoparticles as an efficient nucleic acid delivery system targeting neuronal cells. Drug Development and Industrial Pharmacy 35:719-726, 2009.
Takai et al., Polo-like kinase (Piks) and cancer, Oncogene, 2005, vol. 24, p. 287-291.
Wang et al, Delivery of siRNA therapeutics: barriers and carriers, The AAPS Journal. 2010, vol. 12, pp. 492-503.
Lai et al. Nucleic acid delivery with chitosan and its derivatives, J. Contrl. Release, 2009, vol. 134, pp. 158-168.
Han et al. in oral delivery of shRNA and siRNA via multiplefunctional polymeric nanoparticles for synergistic cancer therapy. Biomaterials, 2014, pp. 4589-4600.
Shim et al. (siRNA as a conventional drug in the clinic? Challenges and current technologies, Drug Discovery Today: Technologies, 2012, vol. 9, pp. e167-e173, published online Jan. 30, 2012).
Burnett et al. (Current Progress of siRNA/shRNA Therapeutics in Clinical Trials, Biotechnol. J., 2011, vol. 6, pp. 1130-1146).
Malhotra et al. (A novel method for synthesizing PEGiylated chitosan nanoparticles: strategy, preparation, and in vitro analysis, Int. J. Nanomedicine, 2011, vol. 6, pp. 485-494).
Rahmat et al. (Synergistic effects of conjugating cell penetrating peptides and thiomers on non-viral transfection efficiency, Biomaterials, 2012, vol. 33, pp. 2321-2326, available online on Dec. 9, 2011).
Kissel I (Chitosan-based formulation for delivery of ON and siRNA, Advanced Drug Delivery Reviews, 2010, vol. 62, pp. 12-27).
Chirachanchai et al. ( One-Pot Synthesis in Aqueous System for Water-Soluble Chitosan-graft-polyethylene glycol Methyl Ether, Biopolymers, 2006, vol. 82, pp. 580-586).
Prakash et al. (Uitrafine chitosan nanoparticles as efficient nucleic acid delivery system targeting neuronal cells, Drug Development and Industrial Pharmacy, 2009, vol. 35, pp. 719-726).
Agilent monograph (Polymer molecular weight distribution and definition of MW average, p. 1 ).
Yang et al., synthesis and characterization of chitosan-g-poly(ethylene glycol)-folate as a non-viral carrier for tumor targeted gene delivery, Biomaterials, 2007, vol. 28, pp. 540-549.
Aminabhavi et al. chitosan as carrier for targeted delivery of small interference RNA, Int. J. Ph arm. 2010, vol. 399, pp. 1-11.
Kissel et al., nano-carriers for DNA delivery to the lung based upon a TAT-derived peptide covalently coupled to PEG-PEI, J. Controlled Release, 2005, vol. 1 09, pp. 299-316.
Alpar et al., Development and characterization of chitosan nanoparticles for siRNA delivery, J. Controlled Release, 2006, vol. 115, pp. 216-225.
Bramwell et al. (Biodegradable mucoadhesive particles for nasal and pulmonary antigen and DNA delivery, Advanced Drug Delivery Reviews, 2005, vol. 57, pp. 411-430).
Boudreau et al., in RNAi medicine for the brain: progresses and challenges, Human Molecular Genetics, 2011, vol. 20, pp. R21-R27.
Rush et al. Non-viral gene therapy for neurological diseases, with an emphasis on targeted gene delivery, Journal of Controlled Release, 2012, vol. 157, pp. 183-189.
Zhang, Y., etal. Biotechnol. Appl. Biochem. (2007). 46; pp. 197-204 (Year: 2007).
Malhotra, M., etal. Drug Dev. Ind. Pharm. (2009), 35(6); pp. 719-772 (Year: 2009).
Fangkangwanwong, J., et al. Biopolymers. (2006), 82; pp. 580-586 (Year: 2006).
Torchilin, V. Biopolymers (Peptide Sci.). (2008), 90(5); pp. 604-610 (Year: 2008).
Malhotra, M., et al. Int. J. Nanomedicine (2011), 6; pp. 485-494 (Year: 2011).
Judge, A. D., etal. J. Clin. Invest. (2009), 119(3); pp. 661-673 (Year: 2009).

d) CS-O-PEG-CONH-TAT e) TAT peptide

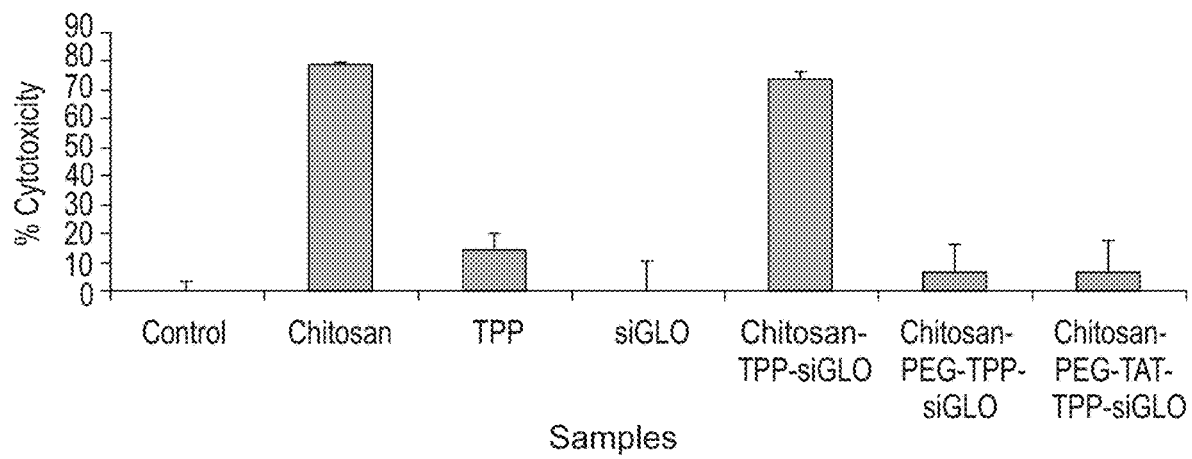
FIG. 8
FIG. 9

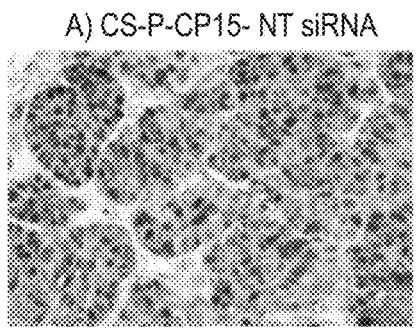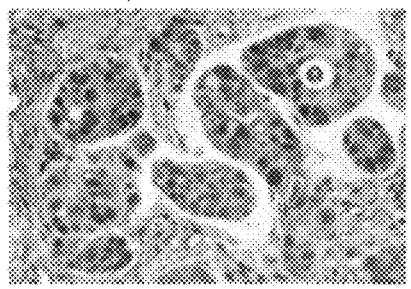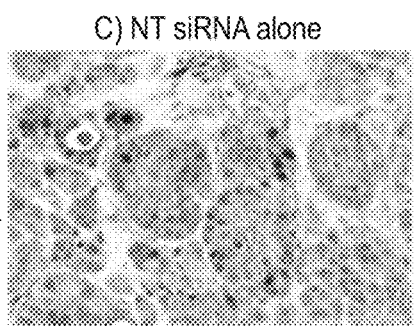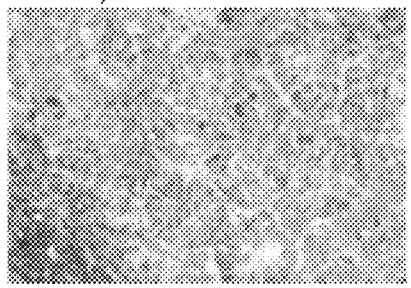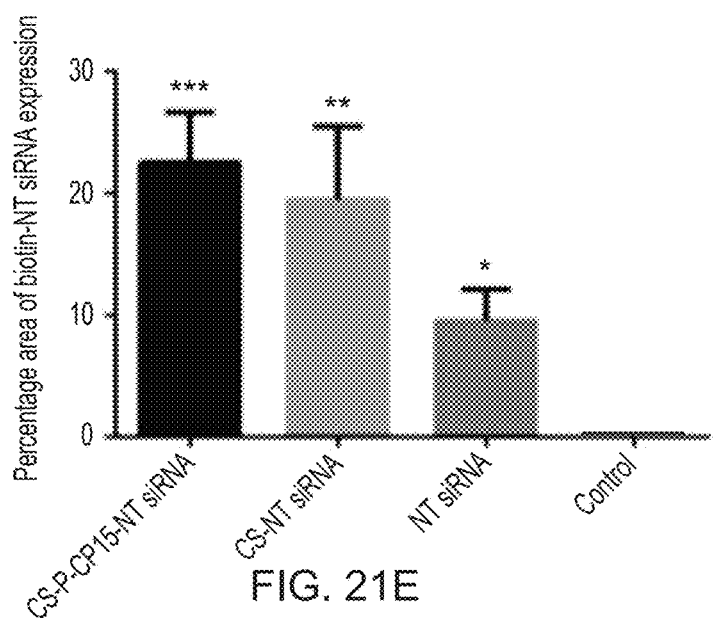

METHODS OF DELIVERING ANIONIC AGENTS IN VIVO USING NON-VIRAL NANOPARTICLE-BASED DELIVERY SYSTEMS

CROSS-REFERENCE TO RELATED APPLICATIONS AND DOCUMENTS

This application is a continuation of U.S. utility patent application Ser. No. 16/218,347, filed Dec. 12, 2018, now U.S. Pat. No. 10,799,601, which is a continuation of U.S. utility patent application Ser. No. 15/335,408, filed Oct. 26, 2016, now abandoned, which is a continuation of and claims priority under 35 U.S.C. § 120 from application Ser. No. 13/916,941 filed Jun. 13, 2013, now abandoned, which claims priority from U.S. provisional patent application 61/660,139 filed on Jun. 15, 2012. The contents of these priority applications are incorporated herein in their entirety. A sequence listing in a computer readable format is enclosed and incorporated herein in its entirety.

TECHNOLOGICAL FIELD

The present invention relates to the development of nanoparticles for delivery of anionic agents such as, for example, nucleic acids, drugs and other molecules. The non-viral nanoparticle design involves the chemical modification of a cationic cross-linkable polymer (such as chitosan) with a hydrophilic linear polymer (such as polyethylene glycol) and a targeting/penetrating peptide. The nanoparticle system can be used for in vitro applications as well as in vivo applications.

BACKGROUND

Delivering agents specifically to a tissue, an organ or a cell type in vivo is a complex task. However, such specific delivery may be crucial for providing therapeutic benefits and/or limiting undesirable side effects. In addition, some agents may also benefit from being more efficiently translocated across a biological membrane and/or a cellular membrane (such as, for example, the cytoplasmic membrane or the nuclear membrane).

One application where specific drug-delivery and/or upregulated cellular uptake is important is neurodegenerative diseases. Neurodegenerative diseases are characterized by progressive, age-related loss of specific subsets of neural cells, which lead to diverse clinical phenotypes depending on the underlying anatomical involvement. The etiology of neurodegenerative diseases is most often multifactorial, likely a result of gene—environmental interaction, which may lead to diseases like Parkinson's, Alzheimer's, Huntington's, Amyotrophic lateral sclerosis (ALS) and Spino Cerebellar Ataxia (SCA). These diseases tend to progress slowly over the time and generally target older population. Currently, there is no treatment available for many of the neurodegenerative diseases that may halt the progression of the disease. The current clinical strategy to deliver drug/gene to the central nervous system involves surgical interventions, which can later pose surgical complications like fluid retention in the ventricles etc., which can have fatal side-effects. It has been estimated that up to 98% of the newly developed small molecules will not/cannot cross the blood-brain barrier (BBB). Also, it is challenging to achieve sufficient distribution and diffusion of the therapeutic drug.

Another application where specific drug-delivery and/or upregulated cellular uptake is important is cancer. Cancer is characterized by uncontrolled growth of a group of cells that infests adjacent tissues and often metastasizes to other organs via lymphatic system or blood stream. Cancer is primarily caused by environmental factors (90-95%) and few with genetic (5-10%). The uncontrolled growth of group of cells in the case of cancer is usually triggered by malfunctioning of the genes that manipulate cell's growth and differentiation. Typically the alteration in cell growth promoting, oncogenes and cell division inhibiting, tumor suppressive genes lead to the formation of cancer cells. The genetic causes of cancer are usually due to gain or loss of an entire chromosome due to errors in mitosis or changes in nucleotide leading to mutations in the genomic DNA. Depending on the stage of the cancer the treatment options available include surgical removal, chemotherapy with anticancer drugs, such as 5-fluorouracil, oxaliplatin and leucovorin, radiation therapy, immunotherapy and hormone block therapy with drugs like cetuximab and panitumumab. However, it has been shown that cancers with genetic origin are not benefited with these chemotherapies. Moreover, the toxicity and side effects have severely limited the safety and effectiveness of these methods.

RNA interference has been demonstrated as an effective/novel therapeutic modality in vivo for the reduction of pathological molecules in neurons, leading to significant efficacy in animal models of Alzheimer's disease, ALS, anxiety, depression, encephalitis, Huntington's disease, neuropathic pain and spinocerebellar ataxia. In addition, siRNAs targeted against proliferation-associated signal transduction pathways, which can halt the tumor progression in animal models, is also emerging as an appealing approach for cancer therapy. SiRNA mediated gene therapy is further being explored by using it in combination with antineoplastic agents as a combinatorial therapy towards cancer treatment.

The therapeutic delivery across BBB and physiological barriers of small molecules like siRNA/nucleic acids/proteins and drugs is challenging or rather ineffective owing to their instability in physiological conditions, improper cellular distribution, low bioactivity, high dosage requirement, and the necessity for continuous long-term infusions. Moreover, off-target effects of siRNA have shown to induce and activate immune responses through Toll-like receptor (TLR)-dependent and TLR independent mechanisms, which can cause toxicological effects due to the activation of interferons (IFNs) and inflammatory cytokines. Though, this strategy can be used as a therapeutic option for cancer therapy, it can also lead to unwanted toxicological effects on non-cancerous cells. The application of a novel therapeutic modality highly depends on the development of an efficient and clinically feasible means of safe administration. Recent advancements in siRNA mediated gene therapy is focusing on the incorporation of specific nucleotide chemistries in the siRNA sequence, such as 2'-O-methyl-modified nucleotides, in order to improve its pharmacologic and nuclease resistant properties and low immuno-stimulatory effect. However, to streamline the systemic delivery of siRNAs in vivo to a specific target tissue, a site-directed delivery strategy is essential.

Various commercially available delivery/transfection reagents do fulfill the need of siRNA delivery in substantially lower doses than compared to siRNA delivered alone, but they lack to emphasize on issues such as target specificity, cytotoxicity, immunological responses, stable systemic delivery and off-target effects of these reagents. Moreover, the efficacy of most of these commercially available transfection reagents is limited to in vitro use. In addition to transfection reagents, viral gene therapy vectors have shown to be most effective but concerns regarding their safety, immunogenicity has limited their use. Moreover, for in vivo applications, delivery via systemic route targets multiple sites, which may not be an ideal deal for many biomedical applications. Thus, development of a delivery vehicle that can address these issues and identify cell-specific receptors, with an ability to distinguish between diseased and normal cells and efficiently delivers a sufficient dose of siRNA to the intracellular compartment of the cell type of interest within the target tissue will be an effective approach to overcome the limitations of currently used therapeutics in in vivo models.

Cationic biodegradable polymers, such as polyethyleneimine (PEI), are commonly used for siRNA transfection, providing a positively charged vehicle to carry the negatively charged siRNA into the target cells. Most of the nanoparticles that are widely being accepted as an alternative approach to gene delivery are developed from cyclodextrin polycations, poly-L Lysine, polyamidoamines, chitosan, quantum dots and liposomes to deliver siRNA for on-target gene silencing. However, transfection frequency, cytotoxicity, serum stability, and active targeting are some of the major concerns associated with non-viral mode of delivery. To overcome the aforementioned effects of nanoparticles, they are surface coated with PEG to eliminate phagocyte capture and nonspecific immune stimulation, which provides better stability and extended blood circulation with low toxicity. Conjugating siRNA with cholesterol and transfection enhancers, such as penetratin1, provides substantial advantage for in vivo delivery and bioactivity of siRNA.

Lipid nanoparticles have been used for drug delivery targeting brain. However, such formulations lack active targeting to the tissue of interest. It has been proposed to use monoclonal antibody as a targeting moiety on a non-viral liposome nanoparticles targeting brain. However, the high molecular weight of antibodies makes the overall size of the nanoparticles big in size, which can therefore be a hindrance to achieve optimal biodistribution at the targeted site. A recent addition to the art is the use of PEI and nucleic acid complex for intraventricular stereotactic screening of stem cells of the brain as a treatment for neurodegenerative diseases and demyelinating diseases. However, PEI as has been known to be a non-biodegradable and toxic could be replaced by biodegradable nanocomplexes with cell-targeting ligands.

In summary, it would be highly desirable to be provided with a delivery system for specifically delivering agents to a tissue (or a group of tissues), an organ (or a group of organs) or a cell type (or a group of cell types). The cellular specificity of the delivery system could be used to lower the dose of the agent as well as limit, if any, the undesirable effects associated with the agent. The delivery system is preferably not based on a viral system and is not capable of reproducing once it enters a cell. It would also be desirable that the delivery system be used in vitro for research purposes, ex vivo for cellular therapy applications as well as in vivo for therapy or diagnostics. In some embodiments, it would be desirable to be provided with a delivery system that is also capable of more efficiently translocating across a biological membrane and/or a cellular membrane (such as, for example, the cytoplasmic membrane or the nuclear membrane).

SUMMARY

According to a first aspect, the present invention provides a polymeric material of a non-viral nanoparticle. The polymeric material comprises (i) a linear polyethylene glycol polymer having a first end and a second end, (ii) a cross-linkable cationic chitosan polymer covalently associated to the first end of the linear polyethylene glycol polymer, and (iii) at least one targeting/penetrating peptide covalently associated to the second end of the linear polyethylene glycol polymer. In one embodiment, the linear polyethylene glycol polymer has an average molecular weight between about 1000 to about 5 000 Da. In another embodiment, the linear polyethylene glycol polymer has an average molecular weight of about 2 000 Da. In still another embodiment, the cross-linkable cationic chitosan polymer has an average molecular weight of about 10 to about 200 000 Da. In still a further embodiment, the average molecular weight of the cross-linkable cationic chitosan polymer is about 1 00 000 Da. In one embodiment, the cross-linkable cationic chitosan polymer has a degree of deacetylation of about 75 to about 85%. In another embodiment, the degree of deacetylation of the cross-linkable cationic chitosan polymer is about 80%. In yet another embodiment, the at least one targeting/penetrating peptide can bind to a cell surface or cell-associated receptor, such as, for example, a targeting peptide having an amino acid sequence comprising $NH_2$-YQPP-STNKNTKSQRRKGSTFEEHK-$NH_2$ (MGF) (SEQ ID NO: 1), a targeting peptide having an amino acid sequence comprising $NH_2$-VHLGYAT-$NH_2$ (CP15) (SEQ ID NO: 2) and/or or a targeting peptide having an amino acid sequence comprising $NH_2$-VPWMEPAYQRFL-$NH_2$ (P160) (SEQ ID NO: 3). In another embodiment, the at least one targeting/penetrating peptide can facilitate the translocation of the non-viral particle across a biological or a cellular membrane, such as, for example, a penetrating peptide having an amino acid sequence comprising $NH_2$-RKKRRQRRR-$NH_2$ (TAT) (SEQ ID NO: 4).

In a second aspect, the present invention provides a process for making the polymeric material described herein. Broadly, the process comprises (i) reacting the first end of a linear polyethylene glycol polymer derivative with the cross-linkable cationic chitosan polymer to form a covalent bond between the cross-linkable cationic chitosan polymer and the linear polyethylene glycol polymer, and (ii) reacting the second end of the linear polyethylene glycol polymer derivative with the at least one targeting/penetrating peptide to form a covalent bond between the at least one targeting/penetrating peptide and the linear polyethylene glycol polymer. In an embodiment, the process further comprises, in step (i) prior to reacting the first end, protecting at least one amine group of the cross-linkable cationic chitosan polymer. In still another embodiment, the process further comprises, after step (ii), deprotecting the at least one amine group of the cross-linkable cationic chitosan polymer. In an embodiment, the linear polyethylene glycol polymer derivative is a linear monomethyl ether polyethylene glycol (mPEG-OH). In another embodiment, the process further comprises, in step (i) prior to reacting the first end, activating the first end of the linear polyethylene glycol monomethyl ether by reacting the polyethylene glycol monomethyl ether with succinic anhydride to form mPEG-COOH and reacting the mPEG-COOH with thionyl chloride to form a mPEG-COCl. In still another embodiment, the process further comprises, in step (i), reacting the mPEG-COCl with the cross-linkable cationic chitosan polymer to form a PEGylated chitosan. In yet another embodiment, the process further comprises, in step (ii) prior to reacting the second end, activating the second end of the polyethylene glycol monomethyl ether by reacting the methyl ether group of the polyethylene glycol with aluminium chloride in ethanethiol to convert the methyl ether group to a hydroxyl group and reacting the hydroxyl group of the polyethylene glycol with succinic anhydride to form an activated PEG-COOH. In an embodiment, the process further comprises, in step (ii), reacting the activated PEG-COOH with the at least one targeting/penetrating peptide to form the polymeric material.

According to a third aspect, the present invention provides a non-viral nanoparticle. The non-viral nanoparticles comprises (i) a plurality of polymeric materials as described herein or produced by the process described herein, wherein the cationic polymer is cross-linked so as to form an internal core; and (ii) an anionic agent entrapped in the internal core. In an embodiment, the anionic agent is a nucleic acid molecule, such as, for example, a short interfering RNA (siRNA). In an embodiment, the non-viral nanoparticles have a diameter of less than 5 nm. In another embodiment, the non-viral nanoparticles have a diameter between 5 and 10 nm. In a further embodiment, the non-viral nanoparticles have a diameter between 100 and 200 nm. In still another embodiment, the non-viral nanoparticle have a diameter between about 5 nm to about 100 nm or between about 50 nm to about 300 nm. In yet another embodiment, the plurality of polymeric materials comprises a first polymeric material having a first targeting/penetrating peptide that can bind to a cell surface or cell-associated receptor and a second polymeric material having a second targeting/penetrating peptide that can facilitate the translocation of the non-viral particle across a cellular membrane. In such embodiment, the first targeting/penetrating peptide can have an amino acid sequence comprising NH$_2$-YQPP-STNKNTKSQRRKGSTFEEHK-NH$_2$ (MGF) (SEQ ID NO: 2) and/or the second targeting/penetrating peptide can have an amino acid sequence comprising NH$_2$-RKKRRQRRR-NH$_2$ (TAT) (SEQ ID NO: 4).

According to a fourth aspect, the present invention provides a process for making a non-viral nanoparticle. Broadly, the process comprises (i) admixing an anionic agent with a cross-linker to form a first solution; and (ii) adding the first solution to a second solution comprising a plurality of polymeric materials described herein or produced by the process described herein so as to form the non-viral nanoparticle. In an embodiment, the cross-linker is sodium tripolyphosphate (TPP). In another embodiment, the anionic agent is a nucleic acid molecule, such as, for example, a short interfering (RNA). In an embodiment, the non-viral nanoparticle has a diameter between about 5 nm to about 100 nm or between about 50 nm to about 300 nm. In an embodiment, the non-viral nanoparticles have a diameter of less than 5 nm. In another embodiment, the non-viral nanoparticles have a diameter between 5 and 10 nm. In a further embodiment, the non-viral nanoparticles have a diameter between 100 and 200 nm. In still another embodiment, the plurality of polymeric materials comprises a first polymeric material having a first targeting/penetrating peptide that can bind to a cell surface or cell-associated receptor and a second polymeric material having a second targeting/penetrating peptide that can facilitate the translocation of the non-viral particle across a cellular membrane. In such embodiment, the first targeting/penetrating peptide can have an amino acid sequence comprising NH$_2$-YQPP-STNKNTKSQRRKGSTFEEHK-NH$_2$ (MGF) (SEQ ID NO: 1) and/or the second targeting/penetrating peptide can have an amino acid sequence comprising NH$_2$-RKKRRQRRR-NH$_2$ (TAT) (SEQ ID NO: 4).

According to a fifth aspect, the present invention provides a method of delivering an anionic agent to a cell. Broadly the method comprises contacting the non-viral nanoparticle described herein or produced by the process described herein with the cell under conditions sufficient for allowing the anionic agent to enter the cell. In an embodiment, the cell is in vitro. In another embodiment, the cell is to be introduced into an individual in need thereof. In still another embodiment, wherein the cell is in an individual in need thereof. In an embodiment, the non-viral nanoparticle is formulated for intranasal administration prior to being administered to the individual, such as, for example, as an intranasal drop. In another embodiment, the method is for the delivery of the agent to the brain. In another embodiment, the method is for the prevention, treatment and/or alleviation of symptoms associated to a neurodegenerative disease or a brain cancer. In some embodiments, the neurodegenerative disease is selected from the group consisting or spinocerebellar ataxia, Huntington's disease, Parkinson's disease, Alzheimer's disease, dementia and amyotrophic lateral sclerosis. In other embodiment, the non-viral nanoparticle is formulated for intravenous administration prior to being administered to the individual. In another embodiment, the method is for the prevention, treatment and/or alleviations of symptoms associated with a proliferative disease, such as, for example cancer (e.g. colon cancer, breast cancer or brain cancer).

Throughout this application, various terms are used and some of them are more precisely defined herein.

Anionic agent. The anionic agent bears a net negative charge (at a physiological pH) and can be formulated inside the internal core formed by the cross-linked cationic polymer. In one embodiment, it is a therapeutic agent which can mediate a therapeutic/biological action on a cell or in an organism. In another embodiment, it is a diagnostic agent which can specifically be located in a cell or in a tissue for diagnostic purposes (e.g. imaging for example). The anionic agent can be a nucleic acid molecule, such as a RNA or a DNA. In some embodiments, the anionic agent can be, for example an small interfering RNA (siRNA), short hairpin (shRNA), ribozymes, micro RNA (miRNA), triplex oligonucleotides, antisense oligonucleotides, plasmid DNA (pDNA) as well as combinations thereof. In another embodiment, the anionic agent is a small chemical entity, such as a drug (e.g. an anti-cancer drug).

Cross-linkable cationic polymer. This polymer bears a net positive and is capable of being cross-linked. Its cross-linkability may be inherent to the polymer (e.g. the polymer may itself contain cross-linkable groups). However, the polymer can also be modified to augment its cross-linkability. The cross-linkable moieties of the polymer are preferably amino groups. This polymer is preferably biocompatible. This polymer, in some embodiments, can be considered hydrophobic or slightly soluble in water. Once integrated in the polymeric material or the nanoparticle, the polymer preferably is not cytotoxic. In an embodiment, the cationic polymer is chitosan.

Chitosan. Chitosan is a polysaccharide obtained by N-deacetylation of chitin. In industrial scale procedures, chitosan is obtained from chitin by alkali treatment of crustacean shells. Chitosan is also present in nature in the cell walls of some fungi and algae and in insects. Chitosan is mainly composed of β-1,4-linked D-glucosamine units with a variable content of N-acetyl-D-glucosamine units. The percentage of N-acetyl-D-glucosamine units is defined as the degree of N-acetylation of chitosan ("DA"), while the percentage of D-glucosamine units is also called the degree of deacetylation ("DDA") of chitosan. Most commercial preparations of chitosan are characterized by dda values between 70 and 99%. Native chitosan molecules, as isolated from natural organisms or obtained after alkaline N-deacetylation of chitin, are of high molecular weight (in the range of millions of daltons) with degrees of polymerization reaching several thousand units. While various applications were described for such high molecular weight chitosans (HMWC), for most applications a narrower, optimal range of molecular weight is under consideration. Chitosan polymers with shorter than native chains are often divided into low molecular weight chitosans (LMWC), with a range of molecular weight roughly between 5 kDa and 100 kDa and chitooligosaccharides (or chitosan oligosaccharides; CHOS) with a lower limit of 0.4 kDa (glucosamine dimer) while the higher limit is less defined (5 to 10 kDa). The CHOS are fully soluble in water and are essentially prepared as undefined mixtures of oligomeric molecules of various molecular weights and degrees of N-acetylation. Chitosan is a cationic polymer due to the presence of amine groups at the C6 position of its pyranose ring and, in its native unmodified state, is only soluble in mild acidic conditions.

Crosslinker. The crosslinker is a compound that promotes or regulates the cross-linking between different groups of the cationic polymer chains, linking them together to create an internal core. In an embodiment, the crosslinker is sodium tripolyphosphate (TPP).

Hydrophilic linear polymer. This polymer is linear in nature (it lacks any branching and only possesses two opposite terminal ends). The hydrophilic linear polymer has at least two distinct and different end, each covalently associated with either the cationic polymer or the targeting/penetrating peptide. It also acts as a linker to camouflage the cross-linked cationic polymer internal core. It also serves to present the targeting/penetrating peptide to the cell. This polymer is preferably hydrophilic to facilitate cellular membrane translocation of the non-viral nanoparticle. This polymer can be biophobic (does not allow on its own, the association to a cell). This polymer is preferably biologically inert.

Internal core. This section of the nanoparticle is formed once the cationic polymer has been cross-linked. The internal core is camouflaged under a layer of hydrophilic linear polymer and contains the anionic agent.

Non-viral nanoparticles. As used in the context of this invention, the term "non-viral nanoparticles" refer to particles in the nanometer range. These particles are considered to be "non-viral" because, even though in some embodiments they are can contain nucleic acid molecules, the particles are not capable of replicating once they have entered a host cell. These nanoparticles are generally of a spherical shape. In some embodiments, the average diameter of the non-viral nanoparticle can be between about 5 to about 100 nm or to about 200 nm. In other embodiments, the average diameter of the non-viral diameter can between about 50 to about 300 nm. In an embodiment, the non-viral nanoparticles have a diameter of less than 5 nm. In another embodiment, the non-viral nanoparticles have a diameter between 5 and 10 nm. In a further embodiment, the non-viral nanoparticles have a diameter between 100 and 200 nm.

Pharmaceutical composition. As used herein, "pharmaceutical composition" means therapeutically effective amounts (dose) of the non-viral nanoparticles together with pharmaceutically acceptable diluents, preservatives, solubilizers, emulsifiers, adjuvants and/or carriers. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, and detergents (e.g. Tween 20™, Tween 80™, Pluronic F68™, bile acid salts). The pharmaceutical composition can comprise pharmaceutically acceptable solubilizing agents (e.g. glycerol, polyethylene glycol), anti-oxidants (e.g. ascorbic acid, sodium metabisulfite), preservatives (e.g. thimerosal, benzyl alcohol, parabens), bulking substances or tonicity modifiers (e.g. lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Polyethylene Glycol. Polyethylene glycol has the formula $H(OCH_2CH_2)_nOH$, wherein n is greater than or equal to 4, with a molecular weight of up to about 20 000 Daltons. Various derivatives of polyethylene glycol may substitute for the H or OH end groups, forming, for example, polyethylene glycol ethers (e.g. PEG-O-R; PEG-O-CHs; CHs-PEG-OH); 2,4-dinitrophenyl ethers of PEG), polyethylene glycol esters (e.g. $PEG-O_2C(CH_2)_{14}CH_3$; $PEG-O_2CCH_2CH_2CO_2$-atropine), polyethylene glycol amides (e.g. $PEG-O_2C(CH_2)_7CONHR$; $mPEG-O_2CCH_2CH_2CONH(CH_3)CHCH_2C_6H_5$; $PEG-O_2CCH_2CH_2CONHCH_2CH_2$-NAD+), polyethylene glycol amines (e.g. $PEG-NH_2$; $PEG-NH(CH_2)_6NH_2$; $PEG-OCH_2CH_2NH_2$; $mPEG-NH_2$), polyethylene glycol acids (e.g. $PEG-O_2C(CH_2)_2CO_2H$; $PEG-O-CH_2CO_2H$; $PEG-O_2C-(CH_2)_7-CO_2H$), polyethylene glycol aldehydes (e.g. $PEG-O-CH_2-CHO$), and electrophilic derivatives (e.g. PEG-Br; $PEG-OSO_2CH_3$; PEG-O). Various phenyl moieties can also be substituted for the H or OH of PEG, such as the 2,4-dinitrophenyl ether of PEG mentioned above. The particular polyethylene glycol derivatives listed above are exemplary only, and the invention is not intended to be limited to those particular examples.

Prevention, treatment and alleviation of symptoms. These expressions refer to the ability of a method or an agent to limit the development, progression and/or symptomology of a specific disorder or pathology. The prevention, treatment and/or alleviations of symptoms associated with a neurodegenerative disease can encompass the limitation of neurodegeneration (e.g. by reducing the apoptosis of neuronal cells). The prevention, treatment and/or alleviation of symptoms of proliferative disease can encompass the reduction of proliferation of the cells (e.g. by reducing the total number of cells in an hyperproliferative state and/or by reducing the pace of proliferation of cells). Symptoms associated with proliferation-associated disorder include, but are not limited to: local symptoms which are associated with the site of the primary cancer (such as lumps or swelling (tumor), hemorrhage, ulceration and pain), metastatic symptoms which are associated to the spread of cancer to other locations in the body (such as enlarged lymph nodes, hepatomegaly, splenomegaly, pain, fracture of affected bones, and neurological symptoms), and systemic symptoms (such as weight loss, fatigue, excessive sweating, anemia and paraneoplastic phenomena).

Proliferation-associated disorders. These disorders form a class of diseases where cells proliferate more rapidly, and usually not in an ordered fashion. The proliferation of cells cause a hyper-proliferative state that may lead to biological dysfunctions, such as the formation of tumors (malignant or benign). One of the proliferation-associated disorder is cancer. Also known medically as a malignant neoplasm, cancer is a term for a large group of different diseases, all involving unregulated cell growth. In cancer, cells divide and grow uncontrollably, forming malignant tumors, and invade nearby parts of the body. The cancer may also spread to more distant parts of the body through the lymphatic system or bloodstream. In an embodiment, the cancer is a carcinoma (such as a colon carcinoma or a breast carcinoma). In another embodiment, the cancer is a glioma (such as a brain glioma). In another embodiment, the cancer is a colon cancer, a breast cancer and/or a brain cancer.

Targeting/penetrating peptide. This peptide is covalently associated with the hydrophilic linear polymer and serves to provide specificity for the delivery of the anionic agent. In some embodiments, the targeting/penetrating peptide is hydrophilic in nature. For example, a targeting/penetrating peptide can have both polar and apolar ends or it can have an alternating pattern of hydrophilic and hydrophobic amino acids. The targeting/penetrating peptide is preferably at least 3 amino acid-long and less than 40 amino-acids long. In one embodiment, the targeting/penetrating peptide preferably and specifically binds to a cellular structure (such as a cellular receptor having at least one portion either embedded in the cellular membrane or protruding from the cellular membrane). When the anionic agent is to be administered to a specific type of cells, the targeting/penetrating peptide specifically binds to this specific type of cells. Alternatively or complementarily, the peptide may also possess a biological characteristic that enables it to penetrate a certain cellular structure. Specific targeting/penetrating peptides are known in the art and can be, for example, capable of penetrating a cellular membrane (such as the cytoplasmic membrane or the nuclear membrane). Some targeting/penetrating peptide can be specific or derived from a protein transduction domain. Other targeting/penetrating peptide can be specific or derived from a growth factor or a hormone. An exemplary targeting/penetrating peptide can be a blood-brain-barrier (BBB)-permeant, amyloid-targeting/penetrating peptide such as KKLVFFAEKGC (SEQ ID NO:16) (as presented in US Patent Serial Number 7,803,351). Other exemplary targeting/penetrating peptides include, but are not limited to TAT, MGF, CP15 and P160 as well as combinations derived therefrom (for example a TAT/MGF combination).

Therapeutically effective amount. A "therapeutically effective amount" as used herein refers to that amount which provides a therapeutic effect for a given condition and administration regimen.

BRIEF DESCRIPTION OF THE DRAWINGS

FIG. 8 shows cytotoxicity study on mouse neuroblastoma cells (Neuro2a) with various treatment using the MTS assay. The results indicate that nanoparticles with chitosan-PEG-TAT and chitosan-PEG formulation showed minimal toxicity to cells as compared to unmodified chitosan nanoparticles. The absorbance was measured at 490 nm using a multiplate cell counter. Control:, Chitosan:, TPP:, siGLO: scrambled siRNA alone, Chitosan-TPP-siGLO:, Chitosan-PEG-TPP-siGLO:, Chitosan-PEG-TAT-TPP-siGLO:.

FIG. 9 shows western blot analysis of ataxin protein performed 24 and 48 hours post-transfection. Samples A and C are positive controls with nanoparticles containing no siRNA and scrambled siRNA (siGLO) respectively. Sample B contains nanoparticles with Ataxin1-siRNA. Silencing is observed after 48 hours for sample B. Actin is used as a protein loading control. The lower panel in this figure provides control results for actin.

FIG. 10B graphically illustrates Quantitative analysis of the stained areas of FIG. 10A in tissues using the Image J software. Results are shown for the cerebral cortex (dark gray) and the cerebellum (light gray) as percentage of area positive for DAB staining in function of siRNA dose. The graph shows a representative result of independent readings from two animals in each group (n=2) mean±s.d. ***P<0.01 was considered highly significant based on Tukey's post-hoc analysis, when compared with other groups.

FIG. 11B graphically illustrates Quantitative analysis of the stained areas in tissues of FIG. 11A using the Image J software. Results are shown for the cerebral cortex (dark grey) and the cerebellum (light gray) as percentage of area positive for DAB staining in function of time elapsed since the administration of the biotin-siRNA. The graph shows a representative result of independent readings from two animals in each group (n=2) mean±s.d. ***P<0.01 was considered highly significant based on Tukey's post-hoc analysis, when compared with other groups.

In FIG. 12A, results are shown for treated animals (first two columns) and control animals (treated with saline, last two columns) in the cerebral cortex, the cerebellum, the lungs, the heart, the kidney the liver and the stomach. The results show a maximum delivery of biotin-siRNA in the brain (cerebral cortex and cerebellum), with a lesser extent in the heart, kidney, liver lungs and stomach. Magnification 400×. FIG. 12B shows quantitative analysis of the stained areas of FIG. 12A in tissues using the Image J software. Results are shown as percentage of area positive for DAB staining in function of organ (cerebral cortex, the cerebellum, the lungs, the heart, the kidney the liver and the stomach) at various doses (from left to right for each organ 0.25 mg/kg, 0.5 mg/kg, 1 mg/kg and 2 mg/kg), compared to the untreated control receiving 0.85% w/v NaCl. The graph shows a representative result of independent readings from two animals in each group (n=2) mean±s.d. ***P<0.01 was considered highly significant based on Tukey's post-hoc analysis, when compared with other groups.

FIGS. 21A-21E represent results of nanoparticles accumulation in the tumor tissue after 4 hrs of dose administration. FIGS. 21A-D show images of SW480 colon cancer indicate the presence of scrambled biotinylated siRNA (0.5 mg/kg) in the tumor tissue after intraperitoneal administration of the treatment nanoparticle formulation. Animals were sacrificed after 4 hrs. Results are shown for the following nanoparticle formulations: chitosan-PEG-CP15 (FIG. 21A), unmodified chitosan nanoparticles (FIG. 21B), non-targeted biotin siRNA alone (FIG. 21C) and untreated control cells (FIG. 21D). FIG. 21E shows image analysis of the mean percent area stained in the tumor tissues of FIGS. 21A-21D. Results are shown as a percentage of biotin-NT siRNA expression in function of treatment (chitosan-PEG-CP15: black bar, unmodified chitosan nanoparticles: light gray bar, non-targeted biotin siRNA alone: dark gray bar and untreated control cells. The graph shows a representative result of the average of three random sections measured per animal tissue, mean±s.d. *p<0.05, **p<0.01 were considered significant based on Tukey's post-hoc analysis, when compared with other groups.

FIG. 22A shows histopathological staining of heart, lungs, kidney, liver and spleen obtained from a mouse xenografted with colon cancer and treated with various nanoparticle formulations (administered at a dose of 0.5 mg/kg) CS-P-CP15-NT siRNA: chitosan-PEG-CP15, CS-NT siRNA: unmodified chitosan nanoparticles, NT-siRNA: non-targeting biotin-siRNA alone and control as untreated. FIG. 22B shows image analysis of the mean percent area stained in the tumor tissues shown in FIG. 22A. Results are shown as mean percentage area stained for the presence of the siRNA in function of the tissue studied and the nanoparticle formulations administered (from left to right for each organs, CS-P-CP15 NT siRNA, CS-NT siRNA, NT siRNA and control). The graphs presents representative results of the average of two random sections measured per animal tissue, mean±s.d. *p<0.05, **p<0.01 were considered significant based on Tukey's post-hoc analysis, when compared with other groups.

In FIG. 25A, AST/ALT ratios (U/L) are shown for mouse treated with CS-PEG-CP15 with siRNA against PLK1 gene (●), CS-PEG-CP15 with non-targeting biotin-siRNA (■), PLK1 siRNA alone (▲) and saline (control ▼). In FIG. 25B, C-reactive protein levels (mg/dl) are shown for mouse treated with CS-PEG-CP15 with siRNA against PLK1 gene (●), CS-PEG-CP15 with non-targeting biotin-siRNA (■), PLK1 siRNA alone (▲) and saline (control ▼). No significant differences between the treatment group and untreated controls were observed. The graph shows a scatter dot plot with n=5 and mean±SE.

FIG. 27A represents the state of tumor, prior to therapy. FIG. 27B represents, reduction in the size of tumor within first 3 weeks of the therapy. FIG. 27C represents, complete reduction in the size of the tumor with presence of only scar tissue. FIG. 27D represents, complete disappearance of tumor mass and scarring tissue from the neck.

FIG. 28A represents the tomogram from the Chest CT from Sep. 27, 2014 and FIG. 28B represents the Chest x-ray from Nov. 26, 2014. As observed, a tumor mass is seen on the upper part of the lower lobe of the right lung in FIG. 28A (white-dotted circle) that is not present on the X-ray of FIG. 28B.

DETAILED DESCRIPTION

Figure 1:
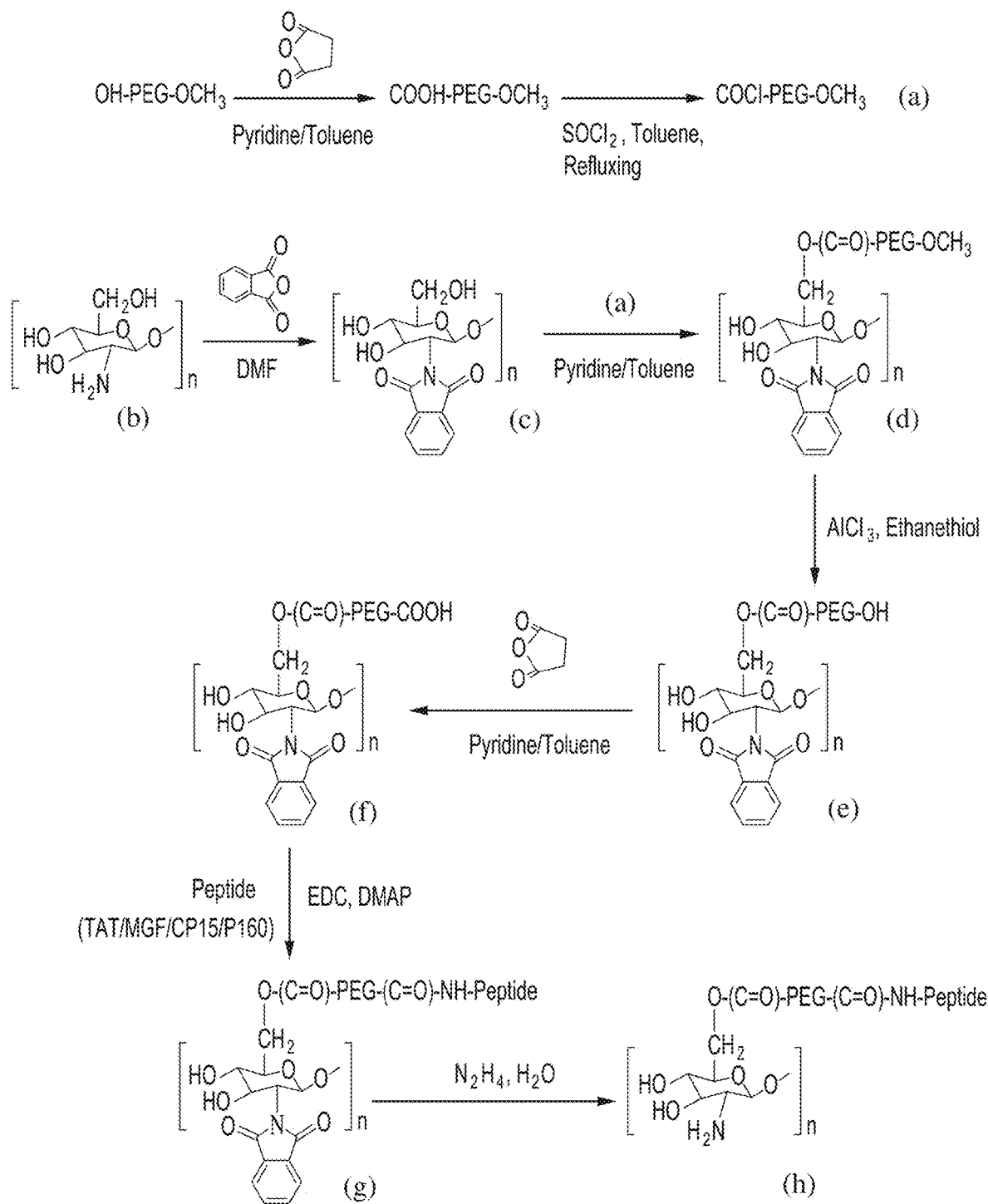
FIG. 1 shows a possible synthetic scheme for preparing peptide-tagged PEGylated chitosan polymer.

The present invention provides a delivery system for specifically delivering agents to a tissue (or a group of tissues), an organ (or a group of organs) or a cell type (or a group of cell types). The delivery system is referred to as a non-viral nanoparticles composed of a plurality of polymeric materials, each comprising a hydrophilic linear polymer (such as PEG) covalently associated at one end with a cross-linkable cationic polymer and at the other end with a targeting/penetrating peptide. The nanoparticles are not based on a viral system for delivering agents. The cellular specificity of the delivery system can be used to lower the dose of the agent used and, consequently, limit, if any, the undesirable effects associated with the agent. The nanoparticles can be used in vitro for research purposes, ex vivo for cellular therapy applications as well as in vivo for therapy or diagnostics. In some embodiments, the nanoparticles can be designed to be more efficient at translocating across a biological membrane and/or a cellular membrane (such as, for example, the cytoplasmic membrane or the nuclear membrane).

Polymeric Material for Non-Viral Nanoparticles

The present invention provides a polymeric material that can be used for the production of non-viral nanoparticles. The polymeric material comprises at least three components, a linear hydrophilic polymer (preferably a linear polyethylene glycol polymer), a cross-linkable cationic polymer (preferably a chitosan polymer) and a targeting/penetrating peptide. In the polymeric material, the linear hydrophilic polymer is covalently associated, at one end, to the cross-linkable cationic polymer and, at the other end, to the targeting/penetrating peptide. The targeting/penetrating peptide is indirectly covalently associated with the cationic cross-linkable polymer (through the linear hydrophilic polymer) but is not directly covalently associated with the cross-linkable cationic polymer.

The components of the polymeric material can be directly and covalently associated with one another. In such embodiment, there is no linker between the cross-linkable cationic polymer and the linear hydrophilic polymer nor between the linear hydrophilic polymer and the targeting/penetrating peptide. However, in an alternative embodiment, in some applications, a linker (either between the cross-linkable cationic polymer and the linear hydrophilic polymer and/or between the linear hydrophilic polymer and the targeting/penetrating peptide) can be present. In some instances, the linker can only be present between the cross-linkable cationic polymer and the linear hydrophilic polymer or between the linear hydrophilic polymer and the targeting/penetrating peptide. In other instances, the linker can be present between the cross-linkable cationic polymer and the linear hydrophilic polymer and between the linear hydrophilic polymer and the targeting/penetrating peptide. The linker between the cross-linkable cationic polymer and the linear hydrophilic polymer can be the same or can differ from the linker between the linear hydrophilic polymer and the targeting/penetrating peptide.

The cross-linkable cationic polymer of the polymer biomaterial can be cross-linked to provide an internal core of cross-linked cationic polymer. In addition, because of the positive charge of the cross-linkable polymer, the internal core provided upon cross-linking provides a micro-environment for a non-covalent association with an anionic agent. In some embodiments, the cross-linking between different polymeric material only occurs between the cationic polymer moieties of from at least two polymeric material. Otherwise stated, no or very little cross-linking occurs between the cationic polymer and the linear hydrophilic polymer or the targeting/penetrating peptide, no or very little cross-linking occurs between the linear hydrophilic polymer moieties of at least two distinct polymeric material, no or very little cross-linking occurs between the linear hydrophilic polymer and the targeting/penetrating peptide, and/or no or very little cross-linking occurs between the targeting/penetrating peptide moieties of at least two distinct polymeric material.

In a preferred embodiment, the cross-linkable cationic polymer is chitosan. In some embodiments, chitosan can be modified through its amine groups. However conjugating other compounds through amines of chitosan can lead to the loss of its cationic nature. The presence of free amine groups (e.g. a net positive charge) on chitosan can help in complexing with negatively charged agents (due to ionic interactions), can help in cellular uptake and, once inside the endosomal cavity, can create a "proton sponge effect" (e.g. a swelling behavior of chitosan observed when encountering an acidic pH inside the cell's endosome). However, it was observed that these free amine groups can be responsible for a mild cellular toxicity. In the polymeric material described herein, chitosan was chemically modified in order to preserve some of its inherent cationic nature. In some embodiments, the amine groups of the chitosan cause a surface charge (of the resulting nanoparticle preferably having a size of less than about 100 nm) between 15 to 25 mV. In order to do so, the amine groups can be first be protected then the chitosan can be conjugated the other functional groups on chitosan with the hydrophilic linear polymer. The expression "protecting amine groups" refer to the protection an amine moiety with any suitable protecting groups. Examples of amine protecting group can be found in Green et al., "Protective Groups in Organic Chemistry", (Wiley, 4$^{th}$ ed. 2007) and Harrison et al. "Compendium of Synthetic Organic Methods" (John Wiley and Sons, 1996).

In the polymeric material described herein, the degree of deacetylation of the chitosan used can be 70%, 75%, 80%, 85% or 90%. In some embodiment, the degree of deacetylation of chitosan can be 80%. In addition, in some embodiments, the chitosan used can be a low (10-50 KDa), medium (50-200 KDa) or high (200-500 KDa) molecular weight chitosan. In preferred embodiments, the chitosan has an average molecular weight of the chitosan can be, for example, about 100 000 Da.

Chitosan is unique among polysaccharides because it carries amino groups which are positively charged in mildly acidic aqueous solution (pH≤5.5). As indicated above, the amine groups can also be coupled to various chemical groups. In the polymeric material described herein, the chitosan is modified (e.g. covalently modified) to be attached (e.g. directly attached) through a hydroxyl group to the linear hydrophilic polymer. In some embodiments, various chitosan molecules also can be cross-linked together via their amino groups.

In some embodiments, chitosan is not a water soluble variety of chitosan. Water soluble chitosan are usually polymeric oligomers, which are not efficient in complexing nucleic acid molecules, such as siRNA. Due to the small size of the water-soluble polymeric oligomers and the siRNA, the complexes formed were shown not to be stable and were readily degraded by the serum proteins. As such, if a water soluble chitosan is used, it must be able to form a stable complex with the anionic agent, such complex being capable of resisting degradation from serum proteins.

In another preferred embodiment of the polymeric material, the linear hydrophilic polymer can be a linear polyethylene glycol (PEG) polymer. Throughout this application, the action of attaching a linear PEG polymer to another entity is referred to as "PEGylation" or "PEGylating" and a material having been attached to a linear PEG can be qualified as "PEGylated". Once covalently associated with the chitosan molecule, the PEG can reduce the steric-hindrance of the nano-particle formed with the polymeric material as well as reduce the inherent mild cellular cytotoxicity associated with non-PEGylated chitosan. In preferred embodiments, the PEG has an average molecular weight between about 2000 Da. In some other specific embodiments, the PEG can also have an average molecular weight of about 1 000 to 5 000 Da.

The third component of the polymeric material is a targeting/penetrating peptide. As indicated herein, the targeting/penetrating peptide has the ability to specifically bind to a cell surface or to a cellular components. It thus provides cell specificity and can also increase cellular uptake of the polymeric material (as well as the non-viral particle produced from the polymeric material). It can, for example, facilitate the crossing of a cellular membrane (such as, for example, the nuclear membrane). Alternatively, the targeting/penetrating peptide can be to a cell surface or cell-associated surface receptor. In such embodiments, the targeting/penetrating peptide can be a fragment or derivative of a protein transduction domain or a fragment or derivative of a growth factor. In this application, a single targeting/penetrating peptide is covalently associated per linear hydrophilic polymer. However, this does not limit the use single peptide per nanoparticle formulation. For example, combination of peptides can be used during the synthesis of the polymeric material for making a population of different polymeric material, each bearing a single peptide that can differ amongst the members of the population. The use of a population of polymeric material can further be used for the production of a multifunctional non-viral nanoparticle.

In some embodiments, the targeting/penetrating peptide can facilitate the translocation through a biological membrane. Such targeting/penetrating peptide can be a TAT oligopeptide covalently conjugated to the PEG polymer. TAT is a transcriptional activator protein encoded by human immunodeficiency virus type 1 (HIV-1) and is involved in the replication of the HIV virus. The basic domain of TAT peptide comprises mainly of arginine and lysine amino acid residues that have shown to play an important role in translocation across biological membrane due to its strong cell-adherence and is independent of receptors, temperature. The TAT peptide can be used for facilitating the translocation of the nanoparticles across any biological membrane. Nanoparticles comprising polymeric material bearing the TAT peptide can also contain other polymeric material bearing other targeting/penetrating peptides.

In other embodiments, the targeting/penetrating peptide can be specific for neuronal cell. Such target peptide include, but are not limited to MGF. MGF is a mechano growth factor. It is a splice variant of IGF-1 (Insulin Growth Factor-1), whose receptors are abundantly present on the surface of Purkinje cells in the cerebellum. IGF-1 is a growth-promoting factor for Purkinje cell development, particularly post-natal survival and dendritic growth. IGF-1 is majorly involved in motor learning process and purkinje cell synaptic plasticity. MGF has shown to promote motor neuron survival but its neuroprotective action is independent of IGF-1. MGF has been identified to have an affinity for myocardial and neurological tissues and can be used as an effective targeting/penetrating peptide for these tissues.

As also indicated herein, in some embodiments, the targeting/penetrating peptide can be CP15. CP15 was identified by the phage display technology. CP15 peptide has shown to be the most effective peptide targeting colon tumor cells but not the normal human intestinal epithelial human cells. CP15 peptide is used as a ligand that will guide the nanoparticles to selectively target the tumor tissue expressing receptors for CP15 peptide (colon cancer).

In some embodiments, the targeting/penetrating peptide can be P160. P160 was identified by phage display technology. P160 peptide has shown high affinity towards breast cancer and neuroblastoma cells without affecting the normal endothelial cells. P160 can be used as a ligand that will guide the nanoparticles to selectively target the tumor tissue expressing receptors for P160 peptide (breast cancer).

Process for Producing the Polymeric Material

In order to produce the polymeric material, the hydrophilic linear polymer can be first covalently associated with the cross-linkable cationic polymer. Such covalent binding can be a direct binding in which no linker is placed between the cross-linkable cationic polymer and the hydrophilic linear polymer. Alternatively, such covalent binding can be an indirect binding where a linker is placed between the cross-linkable cationic polymer and the hydrophilic linear polymer. Once the hydrophilic linear polymer is covalently associated with the cross-linkable cationic polymer, then the hydrophilic polymer is covalently associated with the targeting/penetrating peptide. Such covalent binding can be a direct binding in which no linker is placed between the targeting/penetrating peptide and the hydrophilic linear polymer. Alternatively, such covalent binding can be an indirect binding where a linker is placed between the targeting/penetrating peptide and the hydrophilic linear polymer. As indicated above, there is no direct covalent association or binding between the targeting/penetrating peptide and the cross-linkable cationic polymer (even though some non-covalent association may nevertheless be observed between the targeting/penetrating peptide and the cross-linkable cationic polymer).

In embodiments where the cross-linkable cationic polymer is chitosan, some of (in some embodiments, the majority of) the amine groups of the chitosan molecule can be protected prior to its covalent association with the linear hydrophilic polymer. Such protection can be conferred, for example, by phthaloylation. In such embodiment, the amine groups of the chitosan molecule can be de-protected after the covalent association of between the hydrophilic linear polymer and the targeting/penetrating peptide.

In some embodiments, a derivative of the linear hydrophilic polymer can be used in the process. When the linear hydrophilic polymer is PEG, one of the derivatives that can be used is monomethyl ether polyethylene glycol (mPEG-OH). In such embodiment, the mPEG can first be reacted (with succinic anhydride for example) to form mPEG-COOH and then reacted (with thionyl chloride for example) to form a mPEG-COCl. The mPEG-COCl (having a reactive first end) can then be reacted with the cross-linkable cationic polymer to form a PEGylated cross-linkable cationic polymer. Once the PEGylated cross-linkable cationic polymer has been formed, the other end of PEG containing methy-lether group ($-OCH_3$) can also be reacted to convert it to a hydroxyl group (with aluminium chloride in ethanethiol for example) and then reacted to form an activated PEG-COOH (with succinic anhydride for example). The activated PEG-COOH (having a reactive second end) can then be reacted with the at least one targeting/penetrating peptide to form the complete polymeric material.

In an alternate embodiment to produce the polymeric material, the PEG can be first covalently associated with the targeting/penetrating peptide and then with the cross-linkable cationic polymer. In such embodiment, the mPEG can first be reacted (with succinic anhydride for example) to form mPEG-COOH and then reacted (with thionyl chloride for example) to form a mPEG-COCl. The mPEG-COCl (having a reactive first end) can then be reacted with the targeting/penetrating peptide to form a PEGylated targeting/penetrating peptide. Once the PEGylated targeting/penetrating peptide has been formed, in an additional embodiment, monomethyl ether polyethylene glycol (mPEG-OH) can also be reacted to convert one of its methyl ether group to a hydroxyl group (with aluminium chloride in ethanethiol for example) and then reacted to form an activated PEG-COOH (with succinic anhydride for example). The activated PEG-COOH (having a reactive second end) can then be reacted with the cross-linkable cationic polymer to form the polymeric material.

The person of ordinary skill in the art will understand that the process described herein can be optimized and modified to accommodate the various applications of the polymeric material and should not be intended to be use to limit the scope of the invention.

Non-Viral Nanoparticles

Due to the nature of the polymeric material used, the nanoparticles described herein can be formed by simply admixing an anionic agent with the positively charged cross-linkable polymer. Through ionic interactions, the anionic agent complexes with the cationic cross-linkable polymer. Upon the addition of a cross-linker, the anionic agent becomes entrapped in the cross-linked internal core formed by the cationic polymer. In the non-viral nanoparticles, the anionic agent does not form a distinct structure but is within the cross-linked mesh of the cationic polymer. In some embodiments, the non-viral nanoparticles are shown to exhibit low in vitro cytotoxicity. In embodiments, the nanoparticles have been shown to cross physiological barrier such as the blood-brain barrier (for example, when they have been administered intra-nasally). In other embodiments, the nanoparticles have been shown to be specifically delivered to a tissue (for example, a solid tumor). In some embodiments, the nanoparticles which comprise nucleic acid molecules as the entrapped anionic agent have efficiently released the nucleic acid into the cell's cytoplasm. In additional embodiments, the nanoparticles can be designed for being targeted to the cell nucleus (by using, for example, as one of the targeting/penetrating peptide, a peptide that can facilitate the transfer through the nuclear membrane).

Figure 15:
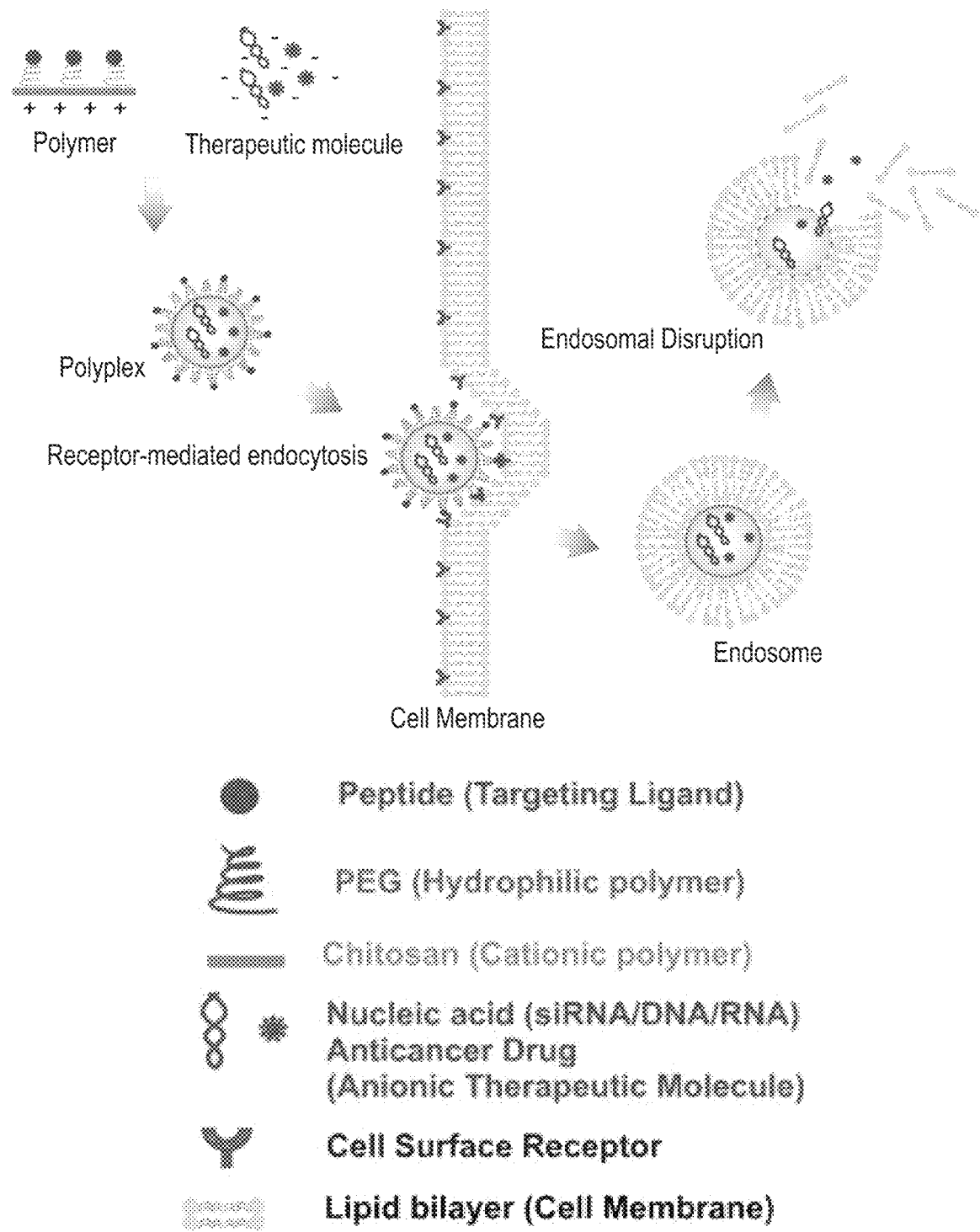
FIG. 15 shows a schematic diagram of a proposed mechanism of cellular uptake of a nanoparticle device comprising peptide tagged PEGylated chitosan nanoparticles carrying either nucleic acid (siRNA/DNA/RNA) or an anticancer drug as a therapeutic molecule.

As disclosed herein, a surface functionalized biocompatible and biodegradable chitosan nanoparticles was developed and can be used to increase the efficacy and stability of the nucleic acid-based therapeutics and/or other therapeutic molecules. In embodiments, the nanoparticles have been shown to provide sustained targeted delivery. Without wishing to be bound to theory, FIG. 15 shows a schematic diagram of a proposed cellular uptake mechanism of the non-viral nanoparticles. In this figure, the nanoparticles are able to release the anionic agent at its targeted site. A targeting ligand can be a specific peptide targeting, for example, a cell-specific receptor. The use of a targeting/penetrating peptide avoids the invasive delivery strategies such as implantation of catheters, intracarotid infusions for therapeutic delivery, surgeries and chemotherapies.

The nanoparticles-based drug-delivery system provided herein is relatively inert and has low integration with physiological system before reaching its targeted cell, organ or tissue. Some of the nanoparticles can handle more payload, be modified with appropriate ligands for specific cell targeting and be administrated repeatedly without fretting about delivery induced toxicity or immunogenicity. Some of the nanoparticles can be designed for being less than about 100 nm in diameter and have a positive surface charge. Some of the nanoparticles can overcome anatomical, biophysical and physiological barriers, such as the blood brain barrier. Some of the nanoparticles are able to safe-guard the anionic agent against degradative enzymes before reaching the targeted site. Some of the nanoparticles can be designed to be target specific and/or can be administered non-invasively.

In order to design the non-viral nanoparticles, various properties of its constituents have been exploited. As indicated above, one embodiment of the cross-linkable cationic polymer is chitosan. Chitosan is a polycationic polymer that has been regarded as a non-toxic, biodegradable and a biocompatible polysaccharide. Due to the presence of primary amine groups, it is only soluble in dilute acids. However, the solubility can be controlled by specifically modifying the primary amine groups thereby making it soluble in solvents like DMSO, DMF, pyridine, THF, etc. Chitosan of low molecular weight has been shown to complex nucleic acids like DNA at acidic pH and exhibit complex stability and integrity.

In addition, chitosan is also considered to be a mucoadhesive agent which can reduce the clearance rate from the nasal cavity. As such, in instances where the nanoparticles are formulated for intranasal delivery (for example in intranasal drops), it is believed that the nanoparticles are absorbed across the nasal epithelia tissue, i.e. olfactory epithelium, and follow olfactory/trigeminal neural pathways. In such embodiment, the pH at which the nanoparticles can be formulated is 6.0, which is in accordance with the pH range maintained in nasal cavity (pH 5.0 to 6.5). Chitosan has also been shown to interact with sialic acid residues in the mucus to open the tight endothelial junctions. It has further been shown to be used for intranasal delivery of proteins.

As also indicated above, in some embodiments, the linear hydrophilic polymer is polyethylene glycol (PEG). This polymer has been extensively used in biomedical and pharmaceutical applications because of its hydrophilic, non-toxic, non-antigenic and non-immunogenic features. It is also a polymer which can be chemically modified easily. In particularly, the use of monofunctional PEG avoids nanoparticles to agglomerate and provides resistance against enzyme degradation. In the context of the present invention, the use of a bifunctional PEG (such as mPEG-COOH) serves as a linker for conjugating two different entities (a cross-linkable cationic polymer and a targeting/penetrating peptide). Because it is neutral in charge and reduces the steric-hindrance of the charged polymers, PEG enables efficient conjugation of the two entities linked on its either side.

The non-viral nanoparticles can comprise a single type of polymeric material bearing the same linear hydrophilic polymer, the same cross-linkable cationic polymer and the same targeting/penetrating peptide. Alternatively, the non-viral nanoparticles can also be made up of different polymeric materials. For example, the non-viral nanoparticles can be made up of polymeric material having the same linear hydrophilic polymer but different cross-linkable cationic polymers and different targeting/penetrating peptides. In another example, the non-viral nanoparticles can be made up of polymeric material having the same linear hydrophilic polymer and the same cross-linkable cationic polymer but different targeting/penetrating peptides. In yet another example, the non-viral nanoparticles can be made up of polymeric material having different linear hydrophilic polymers but the same cross-linkable cationic polymer and the same targeting/penetrating peptide. In still another example, the non-viral nanoparticles can be made up of polymeric material having the same linear hydrophilic polymer and the same different targeting/penetrating peptide but different cross-linkable cationic polymers. In yet another example, the non-viral nanoparticles can be made up of polymeric material having the same cross-linkable cationic polymer but different linear hydrophilic polymers and different targeting/penetrating peptides. In still another example, the non-viral nanoparticles can be made up of polymeric material having the same targeting/penetrating peptide, but different linear hydrophilic polymers and different cross-linkable cationic polymers.

In a specific embodiment, the non-viral nanoparticle is composed of a plurality of polymeric materials. One of the polymeric material can comprise a first polymeric material having a first targeting/penetrating peptide that can bind to a cell surface or cell-associated receptor (for example, the MGF, CP15 or P160 targeting/penetrating peptide). Another polymeric material can comprise a second polymeric material having a second peptide that can facilitate the translocation of the non-viral particle across a cellular membrane (for example the TAT penetrating peptide). Such nanoparticles is thus composed of at least two different targeting/penetrating peptides, one for facilitating the translocation across a biological membrane and another one for providing cellular or tissue-specificity.

The non-viral nanoparticles comprise an anionic agent. The agent should bear a net negative charge in order to complex easily with the cationic polymer. The agent can be used for research purposes, therapeutic purposes and/or diagnostic purposes.

In some embodiment, the anionic agent is a nucleotide-based agent for lowering or inhibiting gene expression and/or protein expression. Such agents include, but are not limited to antisense oligonucleotide, triplex oligonucleotide, miRNA, siRNA, shRNA and ribozyme. In some embodiments, a single type of anionic agent is present in the non-viral nanoparticles. In other embodiments, more than one types of anionic agent is present in the non-viral nanoparticles.

An antisense oligonucleotide is wholly or partially complementary to, and can hybridize with, a target nucleic acid (either DNA or RNA). For example, an antisense nucleic acid or oligonucleotide comprising about 15 to 35 nucleotides spanning the coding/non-coding sequence of a gene or its corresponding transcript whose expression is to be inhibited. In another embodiment, the antisense nucleic acid is wholly or partially complementary to, and can hybridize with, a target nucleic acid. As non-limiting examples, antisense oligonucleotides may be targeted to hybridize to the following regions: mRNA cap region, translation initiation site, translational termination site, transcription initiation site, transcription termination site, polyadenylation signal, 3' untranslated region, 5' untranslated region, 5' coding region, mid-coding region, 3' coding region, DNA replication initiation and elongation sites.

Triplex oligonucleotides, much like antisense oligonucleotides can inhibit transcription and/or expression of a target gene or its transcripts. Triplex oligonucleotides are constructed using the base-pairing rules of triple helix formation and the nucleotide sequence of the target genes. They are usually between 10 and 40 or between 15 to 25 nucleotideslong.

RNA interference (RNAi) is a post-transcriptional gene silencing process that is induced by a miRNA or a dsRNA (a small interfering RNA (siRNA) or small hairpin RNA (shRNA)) and has been used to modulate gene expression. While the invention is not limited to a particular mode of action, RNAi may involve degradation of messenger RNA by an RNA induced silencing complex (RISC), preventing translation of the transcribed targeted mRNA. Oligonucleotides that can mediate RNAi are generally at least 10 nucleotides long. Because manipulation of RNA may be complex, RNAi can be provided with a deoxyribonucleic acid (DNA) compositions encoding small interfering RNA (siRNA) molecules, or intermediate siRNA molecules (such as shRNA), comprising one strand of an siRNA.

Small interfering RNA or siRNA includes any nucleic acid molecule capable of mediating RNA interference "RNAi" or gene silencing. For example, siRNA of the present invention can be double stranded RNA molecules from about 10 to about 30 nucleotides long that are named for their ability to specifically interfere with protein expression. In one embodiment, siRNAs of the present invention are 12 to 28 nucleotides long, more preferably 15 to 25 nucleotides long, even more preferably 19 to 23 nucleotides long and most preferably 21 to 23 nucleotides long. Therefore preferred siRNA of the present invention are 12, 13, 14, 15, 16, 17, 18, 19, 20, 21, 22, 23, 24, 25, 26, 27, 28 nucleotides in length. As used herein, siRNA molecules need not to be limited to those molecules containing only RNA, but further encompass chemically modified nucleotides and non-nucleotides. An siRNA molecule can be assembled from two nucleic acid fragments wherein one fragment comprises the sense region and the second fragment comprises the antisense region of siRNA molecule. The sense region and antisense region can also be covalently connected via a linker molecule. The linker molecule can be a polynucleotide linker or a non-polynucleotide linker. In an embodiment, the siRNA can target the PSN1 gene or the PLK1 gene.

A ribozyme (from ribonucleic acid enzyme, also called RNA enzyme or catalytic RNA) is an RNA molecule that catalyzes a chemical reaction. Some ribozymes may play an important role as therapeutic agents, as enzymes which target defined RNA sequences. Ribozymes can be genetically engineered to specifically cleave a transcript of a gene from a candidate region that is being upregulated with the disease.

The oligonucleotides described herein can be naturally-occurring species or synthetic species formed from naturally-occurring subunits or their close homologs. The term may also refer to moieties that function similarly to oligonucleotides, but have non-naturally-occurring portions. Thus, oligonucleotides may have altered sugar moieties or inter-sugar linkages. Exemplary among these are phosphorothioate and other sulfur containing species which are known in the art. In some embodiments, at least one of the phosphodiester bonds of the oligonucleotide has been substituted with a structure that functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention. Oligonucleotides may also include species that include at least some modified base forms. Thus, purines and pyrimidines other than those normally found in nature may be so employed. Similarly, modifications on the furanosyl portions of the nucleotide subunits may also be affected, as long as the essential tenets of this invention are adhered to. Examples of such modifications are 2'-O-alkyl- and 2'-halogen-substituted nucleotides. Some non-limiting examples of modifications at the 2' position of sugar moieties which are useful in the present invention include OH, SH, $SCH_3$, F, $OCH_3$, OCN, $O(CH_2)$, $NH_2$ and $O(CH_2)_nCH_3$, where n is from 1 to about 10. Such oligonucleotides are functionally interchangeable with natural oligonucleotides or synthesized oligonucleotides, which have one or more differences from the natural structure.

In other embodiments, the anionic agent is a nucleotide-based agent for promoting or increasing gene expression and/or protein expression. Such agents include, but are not limited to expression vectors. In some embodiments, a single type of anionic agent is present in the non-viral nanoparticles. In other embodiments, more than one types of anionic agent is present in the non-viral nanoparticles.

Expression vectors can be derived from viruses (retroviruses, adenovirus, adeno-associated viruses, herpes, lentiviruses and/or vaccinia viruses) or from various bacterial plasmids may be used for delivery of nucleotide sequences to the targeted organ, tissue or cell population. Methods which are well known to those skilled in the art can be used to construct recombinant vectors which will express nucleic acid sequence that is complementary to a specific (or a combination) of nucleic acid sequence. Viral vector delivery systems include DNA and RNA viruses, which have either episomal or integrated genomes after delivery to the cell.

The non-viral nanoparticles of the invention are small enough to translocate across a biological membrane. In some embodiment the diameter of the nanoparticles is between about 5 to about 100 nm. In other embodiments, the diameter of the nanoparticles are between about 50 to about 300 nm. In an embodiment, the non-viral nanoparticles have a diameter of less than 5 nm. In another embodiment, the non-viral nanoparticles have a diameter between 5 and 10 nm. In a further embodiment, the non-viral nanoparticles have a diameter between 100 and 200 nm.

Process for the Production of the Non-Viral Nanoparticles

In some embodiments, the non-viral nanoparticles can be obtained in a one-step fashion. A solution comprising both the anionic agent and the cross-linker is added to a plurality of polymeric materials (identical or different). In an embodiment, when the anionic agent is a siRNA, the ratio between the siRNA and the polymeric materials is at least 2 µg/ml, at least 4 µg/ml, at least 6 µg/ml, at least 8 µg/ml or at least 10 µg/ml of the siRNA for each 0.5 mg/ml of the polymeric material solution. In a preferred embodiment, the ratio between the siRNA and the polymeric materials is about 2 µg/ml of siRNA to be complexed 0.5 mg/ml of polymeric material solution (with average molecular weight of chitosan of 10 KDa) to form nanoparticles in range 5 to 100 nm. In another preferred embodiment, the ratio between the siRNA and the polymeric material is about 8 µg/ml of the siRNA for each 0.5 mg/ml of the polymeric material solution (with average molecular weight of chitosan 50 to 190 KDa) to form nanoparticles in range 50 to 300 nm. The process for making a non-viral nanoparticle includes an anionic cross linker, that can be sodium tripolyphosphate (TPP). The anionic agent (siRNA) along with the anionic cross-linker (TPP) are admixed and then added drop-wise to a cationic polymeric solution in conditions favoring the formation of nanoparticles through ionic interactions. As indicated herein, cross-linking is limited to the cross-linkable cationic polymer moiety of the polymeric material. Cross-linking is not observed between the other components of the polymeric material or the anionic agent. The resulting nanoparticles will have an internal core (in which the anionic agent is entrapped in the cross-linked cationic polymer) having protrusions of hydrophilic linear polymers being covalently associated with the targeting/penetrating peptide. The size of the resulting nanoparticles are in the nanometers range. The shape of the resulting nanoparticles is spherical. In some embodiments, the relative diameter of the non-viral nanoparticle is between about 5 to about 100 nm. In other embodiments, the relative diameter of the non-viral nanoparticle is between about 50 to about 300 nm.

Exemplary cross-linkers include, but are not limited to small chemical entities having either amine reactive groups, carboxyl reactive groups, aldehyde reactive groups, ketone reactive groups, hydroxyl reactive groups, thiol reactive groups and hydrazide reactive groups. Examples of linkers can be found in Greg T. Hermanson, "Bioconjugate techniques" (Elsevier Inc. 2008). More specifically, the cross-linkers include, but are not limited to zero-length cross-linkers (such as, for example, carbodiimides (EDC, EDC and sulfo-NHS, CMC, DCC, DIC), Woodward's Reagent K, N, N-carbonyldiimidazole and Schiff Base Formation and Reductive Amination), homobifunctional crosslinkers (such as, for example, homobifunctional NHS esters (DSP and DTSSP, DSS and BS, DST and Sulfo-DST, BSOCOES and Sulfo-BSOCOES, EGS and Sulfo-EGS, DSG, DSC), homobifunctional imidoesters (such as, for example DMA, DMP, DMS, DTBP), homobifunctional sulfhydryl-reactive cross-linkers (DPDPB, BMH, difluorobenzene derivatives, DFDNB, DFDNPS), homobifunctional photoreactive cross-linkers (such as, for example, BASED), homobifunctional aldehydes (such as, for example, formaldehyde, glutaraldehyde), bis-epoxides (such as, for example, 1,4-butanediol diglycidyl ether), homobifunctional hydrazides (such as, for example, adipic acid dihydrazide), carbohydrazide (such as, for example, bis-diazonium derivatives, o-Tolidine, diazotized, bis-diazotized benzidine) and bis-alkyl halides), heterobifunctional crosslinkers (amine-reactive and sulfhydryl-reactive crosslinkers (such as, for example, SPDP, LC-SPDP, and Sulfo-LC-SPDP; SMPT and Sulfo-LC-SMPT; SMCC and Sulfo-SMCC; MBS and Sulfo-MBS; SIAB and Sulfo-SIAB; SMPB and Sulfo-SMPB; GMBS and Sulfo-GMBS; SIAX and SIAXX; SIAC and SIACX; NPIA), carbonyl-reactive and sulfhydryl-reactive cross-linkers (such as, for example, MPBH, M 2 C 2 H, PDPH), amine-reactive and photoreactive crosslinkers (such as, for example, NHS-ASA, sulfo-NHS-ASA, and sulfo-NHS-LC-ASA; SASD; HSAB and Sulfo-HSAB; SANPAH and Sulfo-SANPAH; ANB-NOS; SAND; SADP and Sulfo-SADP; Sulfo-SAPB; SAED; Sulfo-SAMCA; p-Nitrophenyl Diazopyruvate; PNP-DTP), sulfhydryl-reactive and photoreactive crosslinkers (such as, for example, ASIB, APDP, Benzophenone-4-iodoacetamide, Benzophenone-4-maleimide), carbonyl-Reactive and Photoreactive Crosslinkers (such as, for example, ABH), carboxylate-reactive and photoreactive crosslinkers (such as, for example, ASBA), arginine-reactive and photoreactive crosslinkers (such as, for example, APG)), or trifunctional crosslinkers (4-Azido-2-nitrophenylbiocytin-4-nitrophenyl ester, Sulfo-SBED, MTS-ATF-Biotin and MTS-ATF-LC-Biotin, Hydroxymethyl Phosphine Derivatives).

In some specific applications, it is sufficient (and sometimes even necessary) to provide identical polymeric material for making the nanoparticles. However, in other applications, it is preferably to have different polymeric material in the nanoparticle. In one specific example, it is contemplated that two different polymeric material be provided, each one only differing in the type of peptide that they bear. For example, the two different polymeric material can each bear either a targeting/penetrating peptide that can bind to a cell surface or cell-associated receptor (such as MGF, CP-15 or P160 for example) or a targeting/penetrating peptide that can facilitate the translocation of the non-viral particle across a cellular membrane (such as TAT for example).

Use of the Non-Viral Nanoparticles

The non-viral nanoparticles described herein can be used to specifically deliver an anionic agent to a cell. In order to do so, an appropriate amount of the non-viral nanoparticle is contacted with the cell and incubated in conditions appropriated to allow the entry of the nanoparticles into the cell. In some embodiments, such contact between the nanoparticles and the cell occurs in vitro.

In other embodiments, the cell remains in vitro after the contact (and following the entry of the nanoparticles). However, in some embodiments, the contacted cell can be introduced into an individual in need thereof. Such embodiments may be useful for providing ex vivo gene therapy to the individual. For example, cells explanted from an individual patient (e.g., lymphocytes, bone marrow aspirates, and tissue biopsy) or universal donor hematopoietic stem cells, followed by re-implantation of the cells into the individual, usually after selection for cells which have incorporated the nanoparticles. In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft at an appropriate location (such as in the bone marrow).

In alternative embodiments, the non-viral nanoparticle is formulated for administration prior to being administered to the individual. Such formulation can provide a systemic administration (intravenous, intraperitoneal, intramuscular, subdermal, or intracranial infusion) or a topical administration (cutaneous, intranasal, mucosal, etc.). Although more than one route can be used to administer the nanoparticles, a particular route can often provide a more immediate and more effective reaction than another route. The nanoparticles of the present invention may be administered, either orally or parenterally, systemically or locally. For example, intravenous injection such as drip infusion, intramuscular injection, intraperitoneal injection, subcutaneous injection, suppositories, intestinal lavage, oral enteric coated tablets, and the like can be selected, and the method of administration may be chosen, as appropriate, depending on the age and the conditions of the patient. Since some of the nanoparticles are designed to cross efficiently biological barrier (such as the BBB, the mucosa or/and the skin), the nanoparticles can be formulated for contacting such biological barrier.

In some embodiments, the nanoparticles are used for delivering a therapeutically effective amount of the anionic agent to the brain of an individual in need thereof. The nanoparticles can be formulated as nasal drops for intranasal administration. Such embodiments includes the prevention, treatment and/or alleviation of symptoms associated to a neurodegenerative disease or a brain cancer. Exemplary embodiments of the neurodegenerative diseases include but are not limited to spinocerebellar ataxia, Huntington's disease, Parkinson's disease, Alzheimer's disease, dementia and/or amyotrophic lateral sclerosis. Also contemplated herein are non-viral nanoparticles for the delivery of agents to the brain that can also be used for the prevention, treatment and/or alleviation of symptoms associated to a neurodegenerative disease or a brain cancer In other embodiments, the nanoparticles can be used for delivering a therapeutically effective amount of an anionic agent to a cancer cell (such as a carcinoma cell). The nanoparticles can be formulated for intravenous/intraperitoneal/intratumor administration prior to being administered to the individual. The nanoparticles can be used for the prevention, treatment and/or alleviations of symptoms associated with a proliferative disease, such as cancer (e.g., a colon cancer).

Also contemplated herein are non-viral nanoparticles for the delivery of agents to the brain that can also be used for the prevention, treatment and/or alleviation of symptoms associated to a cancer. The nanoparticles can be administered alone or in conjunction with other anti-neoplastic compounds. The use of the nanoparticles can also be combined with radiation therapy.

The present invention will be more readily understood by referring to the following examples which are given to illustrate the invention rather than to limit its scope.

Example I—Production and Characterization of the Nanoparticles

Material and methods. Low Molecular weight (LMW) chitosan (M.W. 10 KDa) was obtained from Wako (Richmond, Va., USA), having a viscosity of 5~20 cP (at room temperature) and degree of deacetylation of 80.0%. Polyethylene glycol monomethyl ether (mPEG): medium molecular weight (2 000 Da), phthalic anhydride, pyridine, toluene, hydrazine monohydrate, succinic anhydride, ethanethiol, aluminium chloride, sodium tripolyphosphate (TPP), agarose, ethidium bromide (10 mg/ml) and glacial acetic acid of analytical grade were obtained from Sigma (Oakville, ON, Canada). Anhydrous N,N-Dimethylformamide (DMF), 1-ethyl-3-[3-dimethylaminopropyl]carbodiimide hydrochloride) (EDC), 4-(Dimethylamino) pyridine (DMAP), sodium hydroxide (NaOH), methanol, diethyl ether, chloroform and concentrated hydrochloric acid were obtained from Thermo Fisher Scientific (Ottawa, ON, Canada). Thionyl chloride ($SOCl_2$) was obtained from VWR (Mississauga, ON, Canada). The peptides, TAT peptide ($NH_2$-RKKRRQRRR-$NH_2$) (SEQ ID NO: 4) M.W. 1339.40, and MGF peptide ($NH_2$-YQPPSTNKNTKSQRRKGST-FEEHK-$NH_2$) (SEQ ID NO: 1) M.W. 2848.14, were synthesized by Sheldon Biotech, McGill University. Mouse Neuro2a cells and EMEM media were obtained from Cedarlane laboratories (Burlington, Ontario, Canada). MTS cytotoxicity assay kit was obtained from Promega (Madison, Wis., USA). Subcloning DH5-alpha competent cells and Lipofectamine 2000, TrackIt 10-bp DNA ladder (0.5 µg/µl), Pre-cast Nupage 4-12% Bis-Tris gels, Nupage MES running buffer, Nupage transfer buffer, Nupage LDS sample buffer (4×), nitrocellulose membrane 0.45 µm, blotting filter paper and magic mark (1 Kb) protein ladder were obtained from Invitrogen (Burlington, ON, Canada). Orange dye solution (6×) was obtained from Fermentas (Burlington, ON, Canada). pEGFP$^{ataxin1}$ (E3-82Q) plasmid was obtained from Dr. Zoghbi Huda from Baylor College of Medicine, Houston, USA. Plasmid purification Maxi kit is from Qiagen (Mississauga, Ontario, Canada). Primary antibodies: Ataxin-1 (L-19) goat polyclonal antibody, Actin (1-19) goat polyclonal antibody and (HRP)-conjugated donkey anti-goat IgG antibody were procured from Santacruz Biotechnology (Santa Cruz, Calif., USA). Ataxin-1 siRNA (h) was procured from Santacruz Biotechnology (Santa Cruz, Calif., USA). SiGLO red (tagged with Cy3), was obtained from Thermo Fisher Scientific (Ottawa, ON, Canada). Scrambled/Non targeting (NT) siRNA tagged with biotin was obtained from Dharmacon (Lafayette, Colo., USA).

Commercially available low molecular weight chitosan (CS) with an average molecular weight of 10 000 Da and with degree of deacetylation (DA) of 80% (1.00 g) was added to a solution of phthalic anhydride (PH) (2.76 g) in 20 ml of N,N-Dimethylformamide (DMF) in order to protect the amine groups of chitosan. The mixture was stirred for 8 hours at 110° C. under nitrogen atmosphere (Kurita et al., 2002). The resultant product (c) in FIG. 1 was cooled to room temperature and precipitated in ice cold water. The precipitate was filtered, washed with methanol overnight and vacuum dried. This is an important step in carrying forward any further chemical reactions with chitosan, as chitosan being soluble only in acidic conditions becomes soluble in most organic solvents such as DMSO, DMF, THF, pyridine etc. after protection with phthalic anhydride.

Figure 2A:
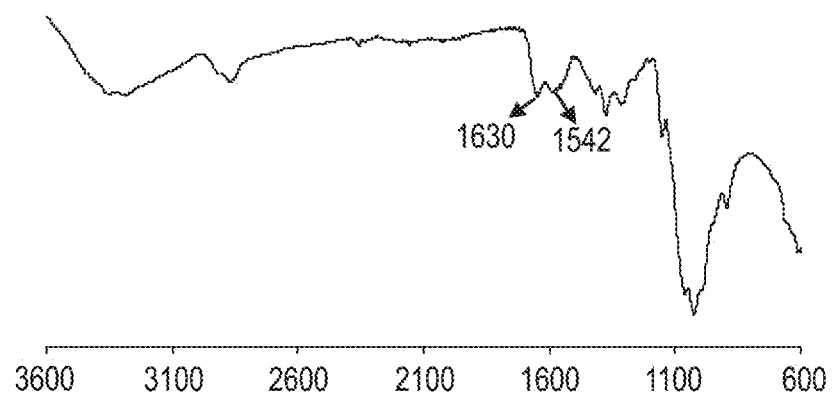
FIGS. 2A-2B shows FTIR spectra of commercially available chitosan (CS) (plot a) and 2-N-phthaloylated chitosan: $v_{max}/cm^{-1}$ 3200-3400 (OH), 1774, 1710 (carbonyl anhydride), 1150-1000 (pyranose), and 720 (arom) (plot b).
Figure 2B:
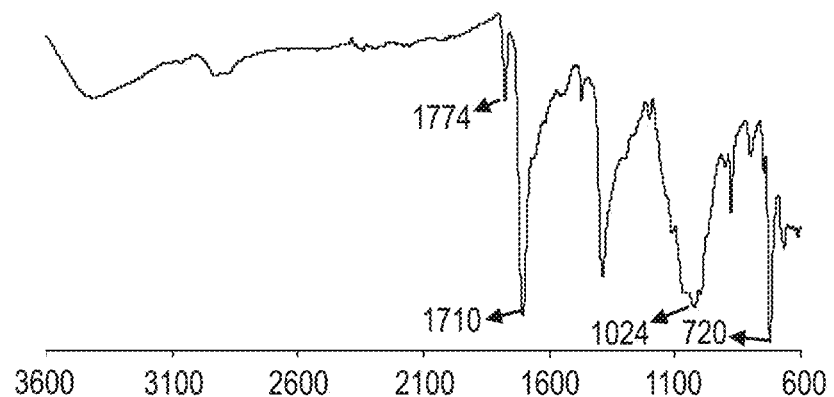

Phthaloylation of the chitosan polymer. $^{13}$C NMR data confirms successful N-phthaloylation of the product. Product (c) in FIG. 1 shows the schematic representation of the N-phthaloyl chitosan. The Total Suppression of Side bands (TOSS) mode exhibit peaks at 124.62 ppm, 131.70 ppm, 134.42 ppm corresponding to phenylene, and 169.66 ppm and carbonyl group of phthaloyl group and the TOSS-dipolar dephasing (TOSDL) mode confirms the absence of CH and $CH_2$ peaks due to their short relaxation time and presence of only two peaks 131.63 ppm and 169.89 ppm assigned to C 1, 2 and carbonyl of phthaloyl group respectively. The IR data shows distinct sharp peaks at 1774 cm$^{-1}$ and 1702 cm$^{-1}$ corresponding to imide of phthaloyl group in FIG. 2. The phthaloyl chitosan prepared by this method becomes gel-like when precipitated in water, which supports the data shown by Kurita, of formation of a uniform structure of phthaloylated chitosan (Kurita et al., 2002).

Pegylation of chitosan: Synthesis of mPEG-COCl. To 10% solution of monomethyl ether PEG (OH-PEG-$OCH_3$) (M.W. 2 000) in toluene was converted to carboxylate-terminated PEG (COOH-PEG-$OCH_3$) by reacting it with four molar excess of succinic anhydride (dissolved in pyridine). The above reaction was set up under anhydrous conditions and refluxed for 6 hours. The product was precipitated with ether, filtered and again re-precipitated twice with chloroform and diethyl ether and finally vacuum dried. The final product obtained (a), is shown in FIG. 1.

Figure 3A:
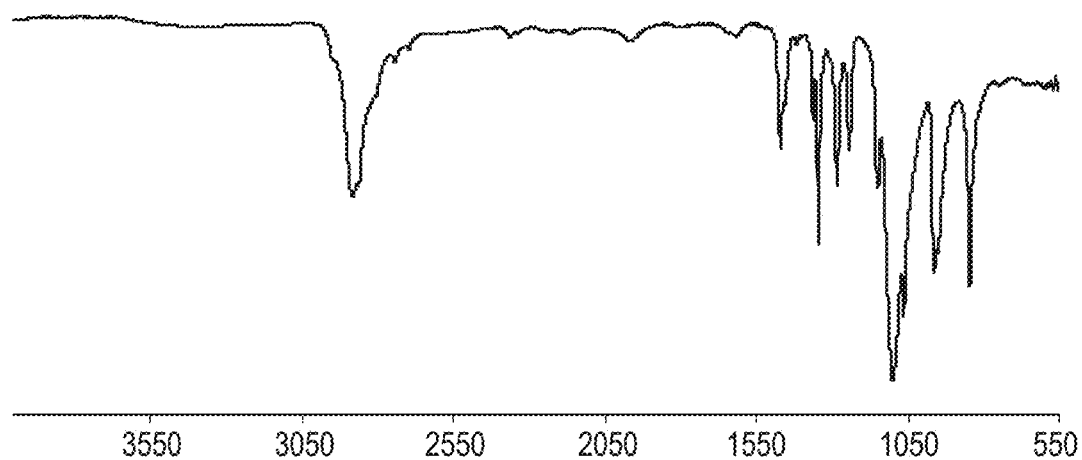
FIGS. 3A-3B shows FTIR spectra of polyethylene glycol monomethyl ether (mPEG-OH) (plot a) and carboxylated mPEG (mPEG-COOH): $v_{max}/cm^{-1}$ 1732 (C=O), 2878 (C—H stretching), 1100 (C—O stretching) (plot b).
Figure 3B:
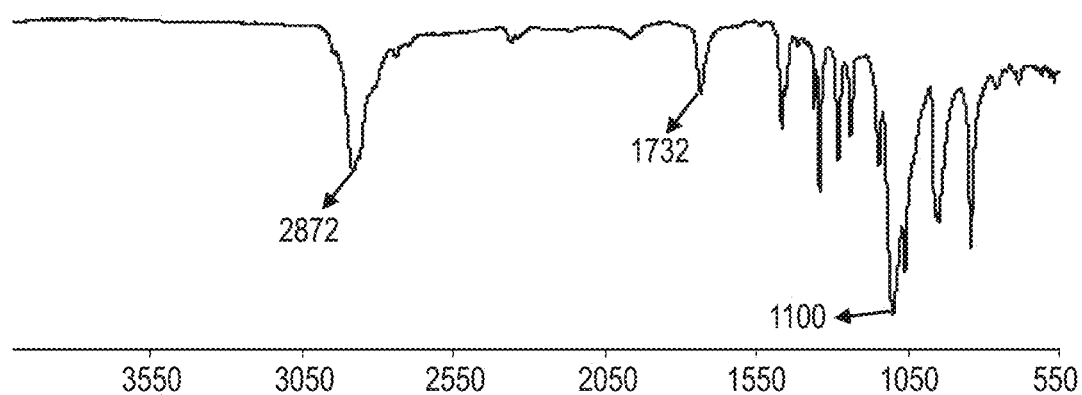

FIG. 3 represents the IR spectra that shows the presence of carboxylic peak at 1732 cm$^{-1}$, confirming the presence of (—C=O) carbonyl groups on PEG. To mPEG-COOH obtained in the previous reaction, 2 fold molar excess of SOCl$_2$ was added under N$_2$ atmosphere to form PEG acyl chloride (COCl-PEG-OCH$_3$) (product b in FIG. 1). The reaction was refluxed to boil for 6 hours, followed by degassing to remove excess SO$_2$ and thionyl chloride.

Pegylation of chitosan: Synthesis of CSPH-O-mPEG (PEGylating phthaloyl chitosan). This product (b) PEG acyl chloride (COCl-PEG-OCH$_3$) obtained in previous reaction is used as an active intermediate to be further conjugated to hydroxyls of 2-N-phthaloyl chitosan (Product c). For this reaction, phthaloyl chitosan (CSPH) (300 mg), product (c), was soaked in pyridine solution overnight and added to mPEG acylchloride (10 g), product (b), in toluene. The reaction was stirred for 2 hours at room temperature and then refluxed to boil for 24 hours (Lin et al., 2007). The resultant product was allowed to cool at room temperature, precipitated in methanol and vacuum dried to yield product (d) in FIG. 1.

Figure 4A:
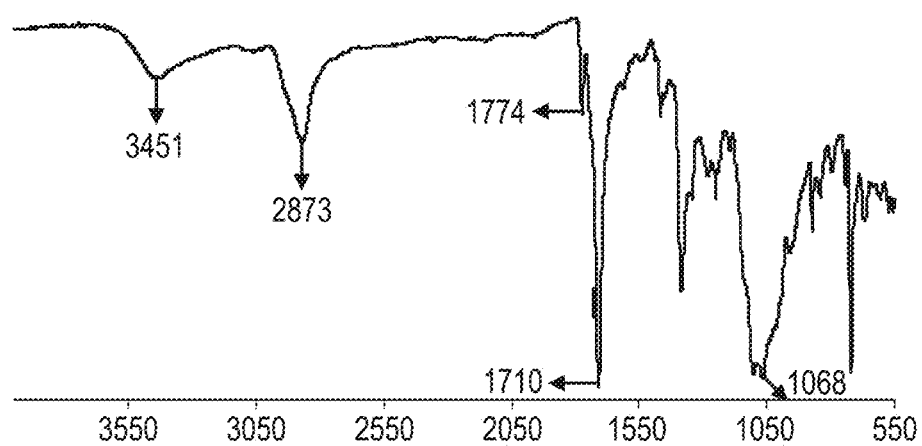
FIGS. 4A-4C shows FTIR spectra of 2-N-phthaloyl chitosan-O-PEG: $v_{max}/cm^{-1}$ 2873 (C—H stretching), 1068 (C—O stretching) of PEG, 1774, 1710 (carbonyl anhydride) and 720 (arom) of phthalimido group on chitosan (plot a); TAT tagged PEGylated phthaloyl chitosan (2-N-phthaloyl chitosan-O-PEG-CONH-TAT): $v_{max}/cm^{-1}$ 2919 (C—H stretching), 1067 (C—O stretching) of PEG, 1774, 1710 (carbonyl anhydride) and 720 (arom) of phthalimido group on chitosan, 1659 (amides) in TAT peptide (plot b); deprotected TAT tagged PEGylated chitosan (chitosan-O-PEG-CONH-TAT): $v_{max}/cm^{-1}$ 2918 (C—H stretching), 1061 (C—O stretching) of PEG, 1644 amides of TAT peptide, and 1543 (amides) in chitosan (plot c).

The FTIR spectra in FIG. 4A shows PEG grafted phthaloylated chitosan with characteristic peaks at 2873 cm$^{-1}$ (C—H stretching), 1068 cm$^{-1}$ (C—O stretching), 1491 cm$^{-1}$, 1451 cm$^{-1}$ and 1254 cm$^{-1}$ belong to PEG. Also the reduction in hydroxyl peaks of chitosan at 3200-3500 cm$^{-1}$, indicates the grafting of PEG onto chitosan forming 2-N-phthaloyl chitosan-O-mPEG, product (d) in FIG. 1.

Tagging a peptide to a pegylated chitosan polymer. To conjugate peptide onto PEGylated phthaloyl chitosan, the methoxy group of PEG was converted to hydroxyl group by following the procedure as mentioned in Lin et al. (2007). In brief equi-molar ratios of CS-mPEG and aluminium chloride were reacted together for 12 hours at room temperature in 20 ml of ethanethiol. The reaction mix was diluted with water, acidified with 10% HCl, filtered and extracted thrice with dichloromethane to yield product (e) in FIG. 1.

The hydroxyl groups formed (CSPH-PEG-OH) were further converted to carboxyl groups by reacting it with 4 molar excess of succinic anhydride in toluene at 100° C. for 12 hours. The product obtained as (f) in FIG. 1 was cooled at room temperature, precipitated with methanol, filtered and vacuum dried. The carboxylic terminal groups of this product (f) i.e. CS-PEG-COOH (12 mM) was conjugated to the equimolar ratio of peptide-NH$_2$ (12 mM) in the presence of EDC (15.5 mM) and DMAP (1.2 mM) in 1 ml of DMF for 24 hrs. This reaction mix was dialyzed against deionized water for 2 days, using a dialysis tube with molecular weight cut-off of 3 500 Da. The resultant product (g) was obtained as shown in FIG. 1.

Figure 4B:
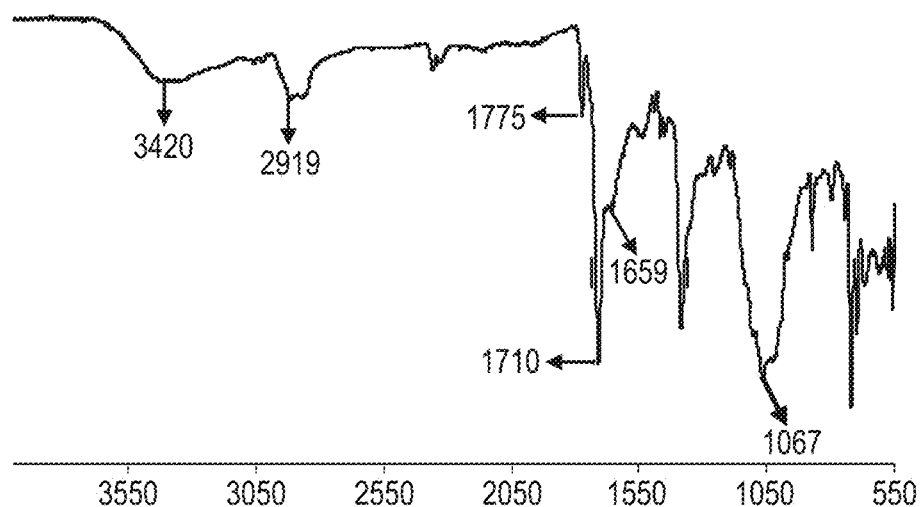

The IR spectra in FIG. 4B shows the appearance of a new peak at 1659 cm$^{-1}$ that shows the presence of amide bonds and confirms the conjugation of peptide onto the polymer forming 2-N-phthaloyl chitosan-O-PEG-CONH-peptide, product (g) in FIG. 4.

Deprotection of chitosan polymer-CS-PEG-peptide (TAT/MGF). As a last step of the synthesis, the amine groups of chitosan were deprotected using 5% hydrazine monohydrate in DMF. The reaction was carried out at 100° C. for an hour under inert conditions. The mixture was allowed to cool at room temperature and was dialyzed against deionized water for 2 days, using a dialysis tube with molecular weight cut-off of 3 500 Da. The sample obtained after dialysis was vacuum dried and marked as product (h) in FIG. 1. Hydrazine monohydrate being basic in nature causes destabilization of the phthaloyl moiety by creating an excess alkaline condition of pH>12.

Figure 4C:
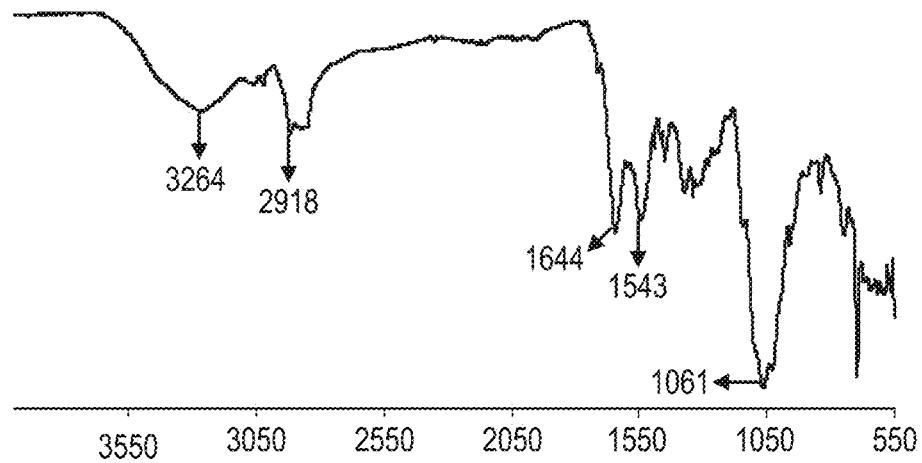

The removal of phthaloyl group from the polymer was confirmed by FTIR, where the absence of peaks at 1775 cm$^{-1}$ and 1710 cm$^{-1}$ confirmed the complete dissociation of phthalimido group from chitosan (FIG. 4C). It was observed that the reaction conditions followed in the scheme at certain steps had no deleterious effects on any of the previous bonds formed. The peak representing the presence of amides due to the peptide shifts from 1659 cm$^{-1}$ to 1644 cm$^{-1}$ and the peak at 1582 cm$^1$ (amide II) belongs to the chitosan. The peaks at 2918 cm$^{-1}$ and 1061 cm$^{-1}$ refers to the presence of (CH$_2$) groups and (C—O stretch) of PEG respectively as observed in FIG. 4c. The final product was dialyzed for 2 days against deionized water in order to get rid of any impurity or byproduct left during the reaction.

Polymer characterization. The polymer CS-PEG-peptide was characterized and analyzed at every step of its derivation through FTIR (Perkin Elmer Spectrum BX), $^{13}$C (Varian 300 MHz broadband NMR) and $^1$H (Mercury 400 and 500 MHz NMR) and Transmission Electron Microscopy (Philips EM410 TEM).

Figure 5A:
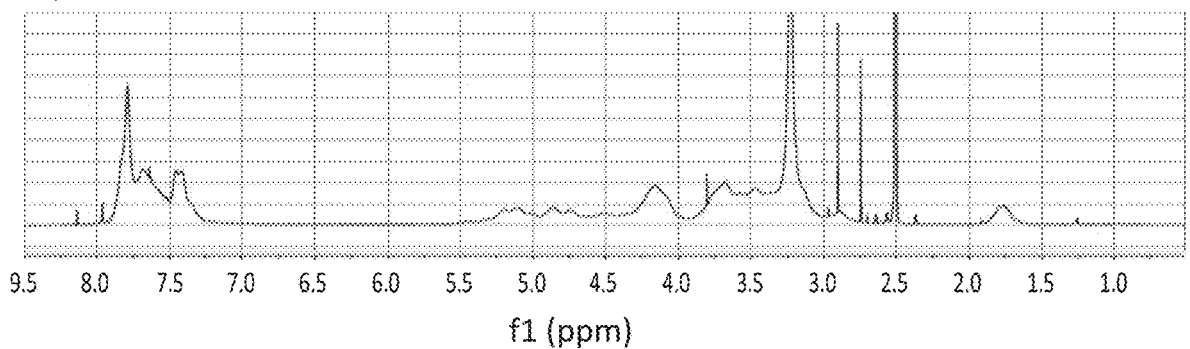
FIGS. 5A-5E shows $^1$H NMR spectra of TAT peptide (plot a); deprotected TAT tagged PEGylated chitosan (CS-O-PEG-CONH-TAT) (plot b); TAT tagged PEGylated phthaloyl chitosan (PHCS-O-PEG-CONH-TAT) (plot c); PEGylated phthaloyl chitosan (PHCS-O-PEG) (plot d); and phthaloylated chitosan (PHCS) (plot e).
Figure 5B:
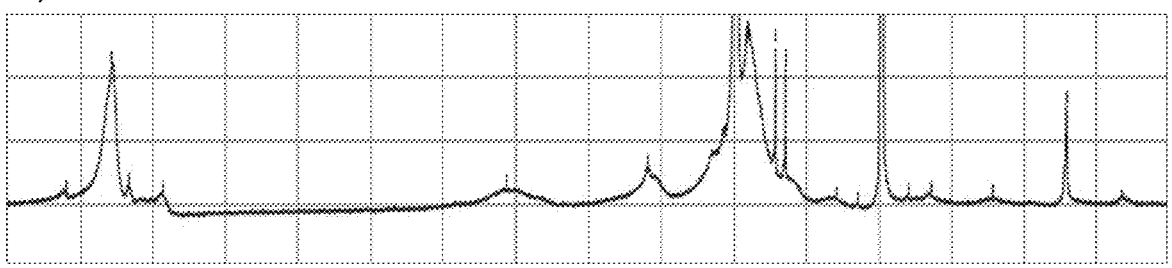
Figure 5C:
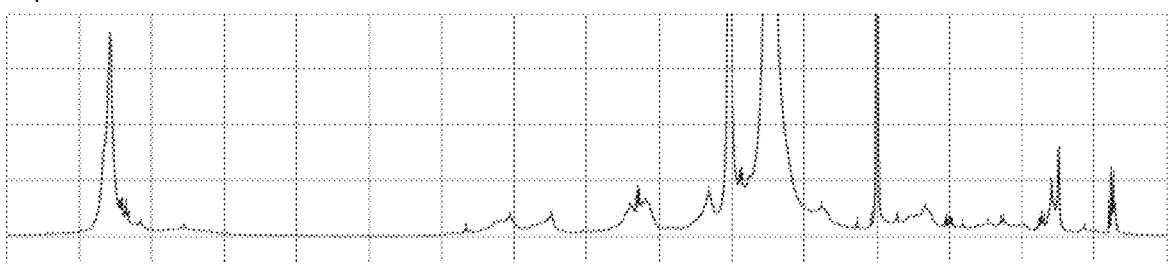
Figure 5D:
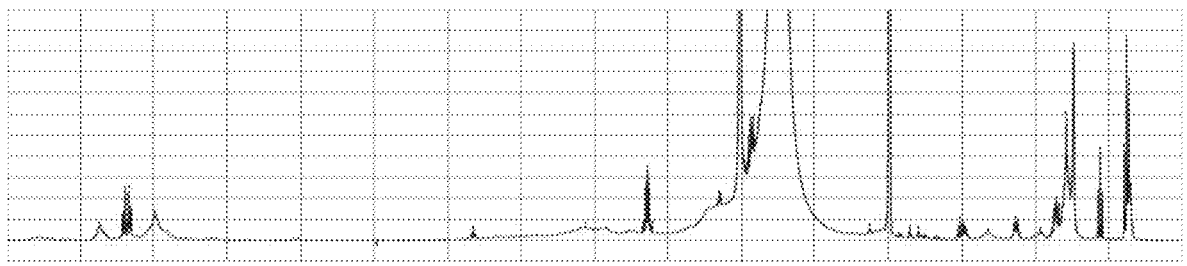
Figure 5E:
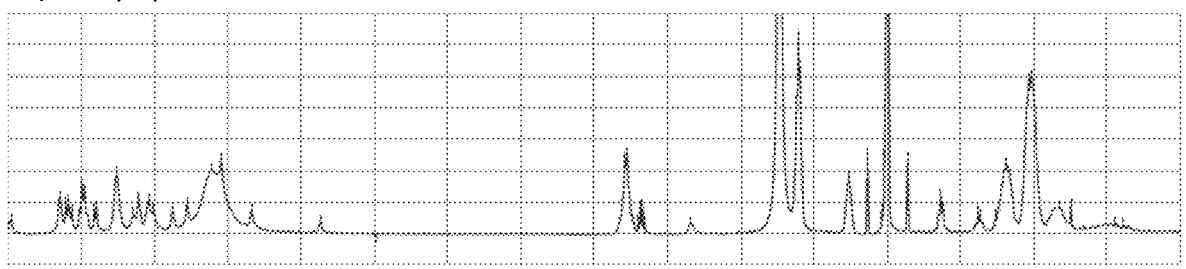

FIG. 5 represents the $^1$H NMR spectra of 2-N-phthaloyl chitosan (FIG. 5A), 2-N-phthaloyl chitosan-O-mPEG (FIG. 5B), 2-N-phthaloyl chitosan-O-PEG-CONH-TAT (FIG. 5C) and chitosan-O-PEG-CONH-TAT (FIG. 5D). The chemical shift at δ 7.78 belongs to the aromatic protons of the phthaloyl moiety, which is present in the spectra of 2-N-Phthaloyl chitosan-O-mPEG, 2-N-phthaloyl chitosan-O-PEG-CONH-TAT but disappeared in chitosan-O-PEG-CONH-TAT spectrum. The multiple peaks of oxymethyl groups in PEG at δ 3.3 to 3.7 cover over the signals of pyranose ring of chitosan in all the three spectras. The weak and broad peak at δ 4.3-4.5 were from the protons of —NH—CH(CH$_2$)—CO— in TAT peptide as observed in spectrum 2-N-phthaloyl chitosan-O-PEG-CONH-TAT. The peak at δ 2.7-2.8 came from the protons of —CH$_2$—NH—NH—NH$_2$ in arginine and the weak and multiple peaks at δ 1.3-1.7 came from the —CH$_2$—CH$_2$—CH$_2$—NH—NH—NH$_2$ in arginine as observed in spectra 2-N-phthaloyl chitosan-O-PEG-CONH-TAT and chitosan-O-PEG-CONH-TAT. The multiple peaks at δ 7.0-8.0 belong to the amines in TAT peptide sequence (FIG. 5E).

Figure 6A:
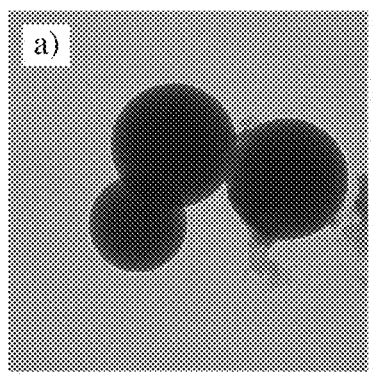
FIGS. 6A-6F show transmission electron microscopy (TEM) image of PEGylated chitosan polymer, magnification: 53 800×, scale bar: 500 nm (FIG. 6A); TAT/MGF tagged PEGylated chitosan polymer, magnification: 53 800×, scale bar: 500 nm (FIG. 6B); acid treated (pH 5.5) TAT/MGF tagged PEGylated chitosan polymer, magnification: 70 700×, scale bar: 500 nm (FIG. 6C); empty TAT/MGF tagged PEGylated chitosan nanoparticles, magnification: 162 000×, scale bar: 100 nm (FIG. 6D); unmodified chitosan-siRNA nanoparticles, magnification: 122 000×, scale bar: 100 nm (FIG. 6E); and chitosan-PEG-TAT/MGF-siRNA nanoparticles, magnification: 302 000×, scale bar: 100 nm (FIG. 6F).
Figure 6B:
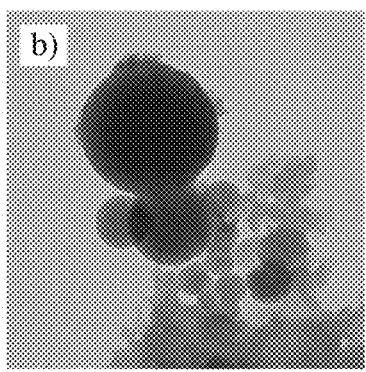
Figure 6C:
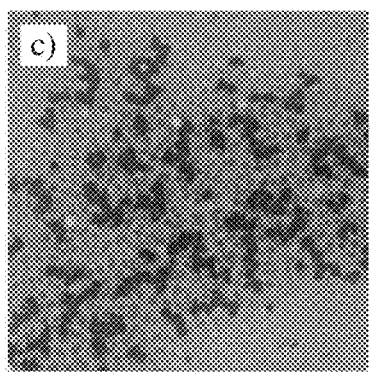

Preparation of siRNA complexes with CS-PEG-PEPTIDE (TAT/MGF) nanoparticles. FIG. 6 represents TEM images of the polymer chitosan-O-PEG-CONH-peptide dissolved in dilute acetic acid at pH 6 at a concentration of 0.5 mg/ml, which was sonicated for 10 minutes before being observed under the transmission electron microscope (TEM). FIG. 6A shows the TEM image of the polymer PEGylated chitosan polymer at magnification 53 800× and FIG. 6B is the peptide tagged PEGylated chitosan polymer at magnification 53 800×. The spherical shape of the particles formed is attributed to the conjugation of PEG on chitosan. FIG. 6C shows effect of acidic pH (5.5) on peptide tagged PEGylated chitosan polymer at magnification 70 700× formed before complexing siRNA. The polymer appeared to disperse and disintegrate at acidic pH.

To form siRNA complexed nanoparticles, scrambled/non-targeting (NT) siRNA (siGLO-red) was mixed with TPP at pH 3, as described previously (Malhotra et al., 2009) and then added drop-wise to the polymer solution of chitosan-PEG-peptide at a concentration 0.5 mg/ml. Final concentration of siRNA used was 2 µg/ml. The solution was stirred for an hour at room temperature. The nanoparticles obtained were viewed under TEM.

Figure 6D:
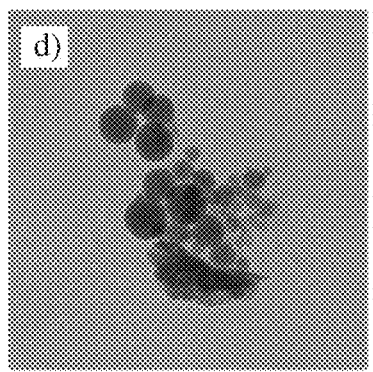
Figure 6E:
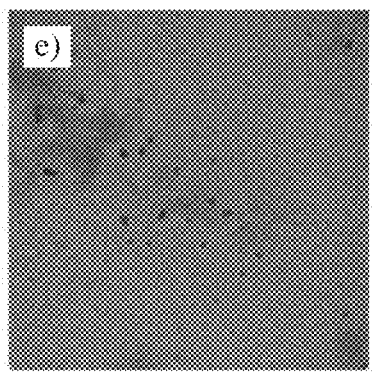
Figure 6F:
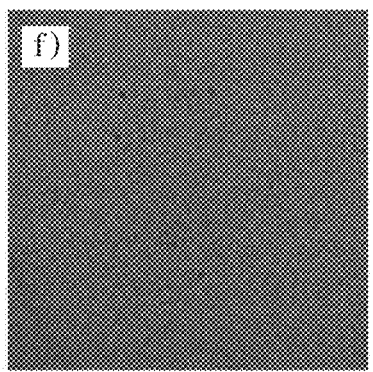

FIG. 6D shows nanoparticles formed with the modified Chitosan-PEG-peptide polymer, without siRNA, using TPP as a crosslinker. The nanoparticles range in the size of 50-100 nm. FIGS. 6E and 6F represent nanoparticles formed with unmodified chitosan complexing siRNA and Chitosan-PEG-peptide polymer complexing siRNA respectively. On encapsulating siRNA, the nanoparticles obtained from chitosan-PEG-peptide polymer were smaller than 20 nm and appeared more spherical and monodispersed, (FIG. 6F) as compared to the particles obtained by unmodified chitosan polymer which were 50-80 nm and non-spherical (FIG. 6E). The reduction in size is because of the increase in amine groups due to the peptides, which interacts more efficiently with negatively charged siRNA and thus the amount of siRNA complexed increases as well. The increased encapsulation efficiency yields smaller particles.

Example II—In Vitro Transfection with the Nanoparticles

Figure 7:
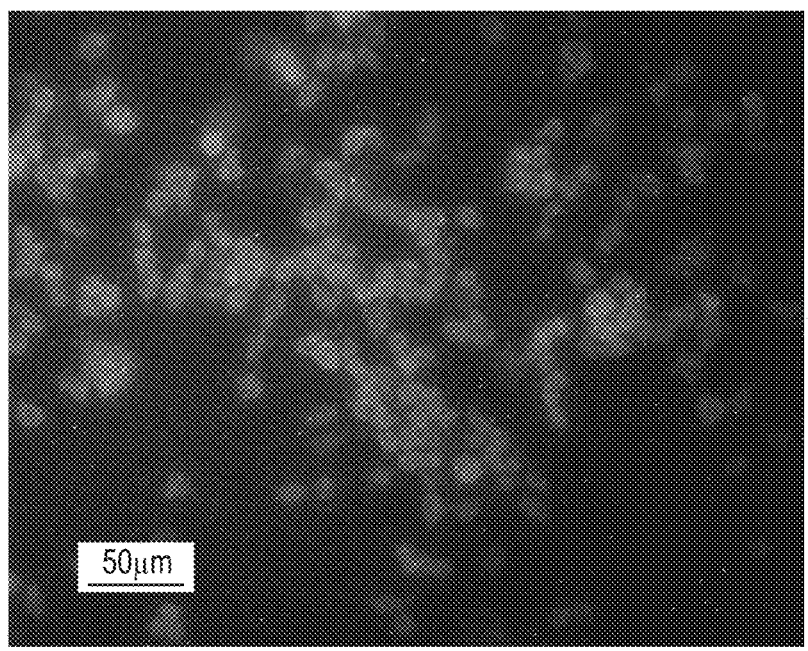
FIG. 7 shows mouse neuroblastoma (Neuro2a) cells transfected with modified chitosan-PEG TAT-siGLO nanoparticles. siGLO (red) is a scrambled siRNA, which is tagged with a Cy3 dye, which upon transfection indicates the delivery of siRNA.

Transfection efficiency of the nanoparticles complexing siGLO red (Cy3-labelled transfection indicator) was performed on mouse neuroblastoma cells (Neuro 2a). 100% transfection efficiency was achieved with chitosan-PEG-TAT nanoparticles encapsulating siGLO-red in mouse neuroblastoma cells seeded at a density of 20 000 cells per well in a 96 well plate, supplemented with Eagles minimum essential medium (EMEM) with 10% FBS (FIG. 7). The fluorescence was achieved after 4 hours of transfection and was observed under fluorescence microscope (Nikon Eclipse TE2000-U) at a wavelength of 660 nm.

The cytotoxicity assay was performed using MTS assay on cells seeded in 96 well plate after 4 hours of transfection with different treatment groups (FIG. 8). The results indicate minimal toxicity with chitosan nanoparticles modified with PEG alone and with chitosan nanoparticles modified with PEG and peptide both as compared to the unmodified chitosan nanoparticles. Without wishing to be bound to theory, it is believed that the presence of PEG and peptide which are hydrophilic in nature and pose no adverse or toxic effect on the cells. It is also believed that PEG reduces the steric-hindrance and TAT is an excellent cell-penetrating peptide. It is also noted that chitosan polymer itself was observed to be toxic to the cells, whereas anionic agent siGLO and the cross linker TPP showed no/minimal adverse effects on the cells.

Plasmid purification: Ataxin-1 cDNA. The plasmid DNA containing ataxin-1 cDNA, purified and resuspended in Tris-EDTA buffered solution [pGFP-ataxin (Q82)] was a kind gift from Dr. Zoghbi Huda, which was used for the transformation experiment in DH5-alpha competent cells by means of chemical transformation also known as heat shock transformation method. The procedure for chemical transformation was followed according to the manufacturer's protocol (Invitrogen). The colony selective antibiotic for pGFP-ataxin was kanamycin (30 µg/ml). Stock cultures of transformed plasmid in DH5-alpha cells were made in sterilized 80% glycerol and were stored at −80° C. Plasmid purification was performed following the protocol of Qiagen's maxi kit. The purified plasmid obtained was quantified for its concentration and purity. The percentage purity of the plasmid was quantified using UV spectrophotometer. The ratio of Abs 260/280 obtained was 1.8 which signifies that the plasmid was purified and the concentration obtained was 266 µg/ml for pEGFP.ataxin1.

Overexpression/Suppression of ataxic proteins in Neuro2A cells. Transfection studies were performed using a functional siRNA against ataxin gene. 100 000 cells were seeded in a 12-well plate, supplemented with EMEM containing 10% FBS. The cells were incubated for 24 hours at 37° C., 5% $CO_2$. After 24 hours, the media was replaced with FBS free EMEM medium and the cells were transfected with pEGFP-ataxin1 at a concentration of 250 ng/µl using Lipofectamine 2000™ (Invitrogen) according to manufacturer's protocol. Optimal transfection efficiency with lipofectamine was determined experimentally. After 6 hours of transfection, the media was replaced with complete growth EMEM medium containing 10% FBS. Ataxin1-siRNA (Santacruz Biotechnology) was complexed with chitosan-PEG-peptide nanoparticles as previously described. The Ataxin1-siRNA transfection with nanoparticles was performed on cells over-expressing ataxin protein. After 24 hours of overexpression, 40 µM of Ataxin1-siRNA complexed with nanoparticles was used to transfect neuronal cells per well (12 well plate) containing FBS free EMEM medium. Further to nanoparticles transfection after 6 hours, the media was again replaced with complete growth EMEM medium containing 10% FBS. Empty nanoparticles and nanoparticles containing scrambled siRNA (siGLO) were used as positive controls. The cells were harvested for ataxin protein estimation after 24 and 48 hours.

Protein extraction and Western Blot. To estimate the amount of silencing by functional siRNA delivered through Chitosan-PEG-peptide nanoparticles, cultured cells were washed twice with cold PBS and lysed using 2× Laemmli Buffer (4% SDS, 20% glycerol, 10% 2-β-mercaptoethanol, 0.004% bromophenol blue, 0.125 M Tris HCl, pH 6.8) at 4° C. on an orbital shaker. The cells were scrapped after 20 minutes (on ice). The extracted protein samples were heated at 70 to 100° C. for 10 minutes, before loading on gels. Procedure of western blot was performed according to the manufacturer's protocol (Invitrogen). Pre-cast Nupage Bis-Tris (4-12%) gels were used for running the protein samples. Magic mark 1 Kb protein ladder was used as a standard. The gel was electrophoretically transferred to nitrocellulose membrane using SemiDry blot apparatus (Invitrogen).

The membrane was incubated for 1 hr in 5% non-fat powdered milk in 0.2% TBST. The membrane was then incubated overnight with goat ataxin-1 IgG polyclonal antibody (1:5 000 dilution; Santacruz Biotechnology). After three washes in TBST, the membrane was incubated with horseradish peroxidase (HRP)-conjugated donkey anti-goat IgG antibody (1:2 000 dilution; Santacruz Biotechnology). The membranes were then washed three times in TBST followed by detection of signal with a chemiluminescence detection kit (Roche) (FIG. 9).

To control the protein loading, the membrane was reprobed with antibody a-Actin (1:10 000; Santa Cruz Biotechnology). As observed in FIG. 9, samples were run after 24 and 48 hours of transfection. Sample A and C were positive controls with empty and scrambled siRNA (siGLO) containing CS-PEG-TAT nanoparticles respectively and sample B had Ataxin1-siRNA. The silencing was observed after 48 hours in sample B. These results indicate that nanoparticles prepared using the proposed synthetic scheme successfully and efficiently delivered siRNA, leading to gene silencing against ataxin 1 in neuronal cells in vitro.

Example III—In Vivo Use of the Nanoparticles for Brain Delivery

Four weeks old C57BL/6J male mice weighing 10 to 15 g were purchased from Jackson laboratories (Bar Harbor, Me., USA) and housed in an environment with controlled temperature (22° C.), humidity, and a 12 h light/dark cycle at McGill's Animal care facility. The animal experiment was conducted as per the protocol approved by the Animal care committee at McGill University (Montreal, QC, Canada). Standard mouse chow pellets and water were supplied ad libitum. Animals were acclimatized for a week before the start of the experiment.

Animal Study, tissue processing and staining. Animals were randomized into 4 groups to receive treatment formulation consisting of biotin tagged scrambled siRNA, complexed with CS-PEG-peptide (TAT/MGF) nanoparticles (two animals/group). One animal in each group received PBS and was treated as control. CS-PEG-peptide (TAT/MGF) nanoparticle formulations complexing biotin-siRNA were concentrated to 4 different doses at: (a) 0.25 mg/kg, (b) 0.5 mg/kg, (c) 1 mg/kg and (d) 2 mg/kg siRNA using Am icon Ultra-15 centrifugal filters (MW cut-off 3 000 Daltons, Millipore) prior to dosing. The animals were anesthetized with 75-100 µl of cocktail comprising ketamine (100 mg/kg), xylazine (10 mg/kg) and acepromazine (3 mg/kg) via intraperitoneal administration. A total of 30 µl of the nanoparticle formulation was administered intranasally (2 µl/drop) over 15-20 minutes period, once a day. The experimental end points were 4, 16, 24 and 48 hrs. Before each end point the animals were anesthetized using the above mentioned anesthetic cocktail and perfusion fixed with 4% paraformaldehyde (PFA) (Sigma Aldrich, Canada). Brain, Lungs, Heart, Stomach, Kidney and Liver were harvested and kept at 4° C. in 4% PFA for 48 hrs. After which the tissues were trimmed to 3 mm thick sections and stored at 70% ethanol in histology cassettes. The tissues were paraffin embedded and processed into 4 µm thick section on slides at the histology core facility (The Rosalind and Morris Goodman Cancer Research Centre, McGill University). The tissue section on slides were stained with Vectastain elite ABC kit (Vector laboratories; Burlingame, Calif., USA) as per the manufacturer's protocol and Diaminobenzidine (DAB) was used as a substrate to assess the presence of biotin (brown staining). Hematoxylin was used as a counterstain and slides were mounted with permount (Vector laboratories; Burlingame, Calif., USA) and observed under compound microscope (Leica DM500; Ontario, Canada) at ×400 magnification.

Figure 10A:
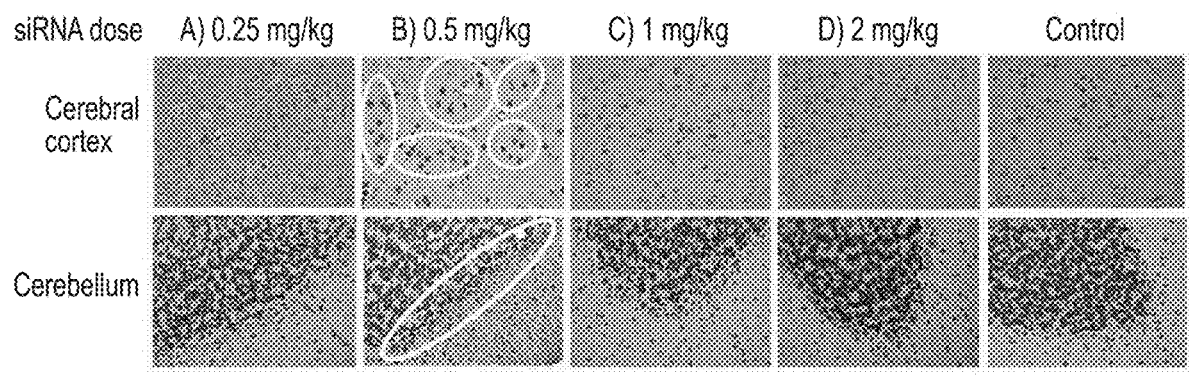
FIGS. 10A-10B represent histopathological images of brain tissues (cerebral cortex (first row) and cerebellum (second row)) four hours after receiving the nanoparticle formulation of biotin-siRNA at various doses: 0.25 mg/kg, 0.5 mg/kg, 1 mg/kg, 2 mg/kg and PBS only (control) (FIG. 10A). The circled regions in column (B), identified with DAB staining, indicate the presence of biotin-tagged scrambled siRNA in neurons observed. Magnification 400×.
Figure 10B:
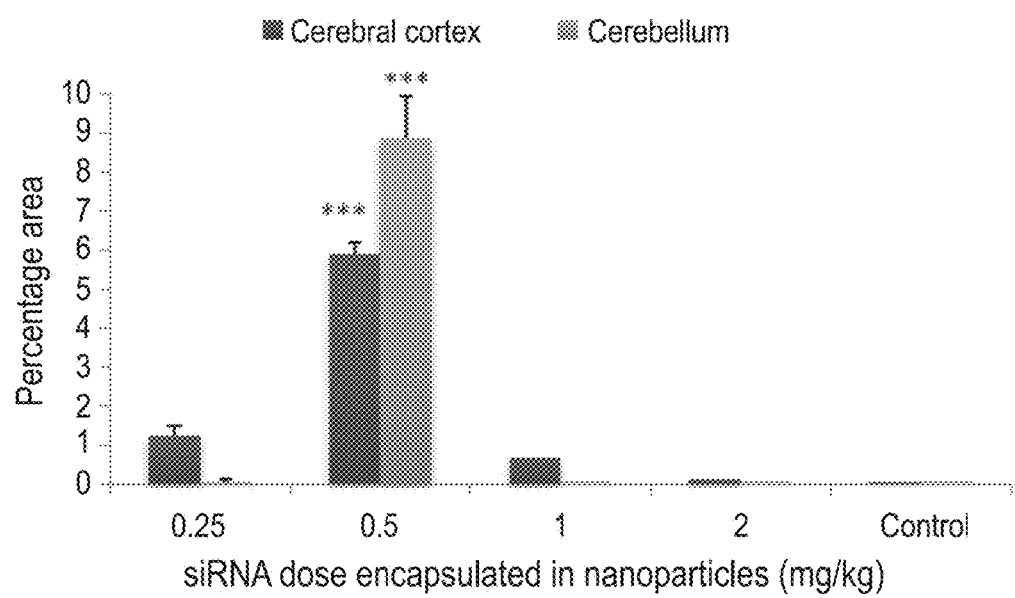

FIG. 10 (I) represents histopathological sections of brain tissue (cerebral cortex) at 4 hrs time point with different doses, containing (A) 0.25 mg/kg, (B) 0.5 mg/kg, (C) 1 mg/kg, (D) 2 mg/kg and (E) PBS (control). The dark brown stained pyramidal neuronal cells obtained with 0.5 mg/kg of scrambled biotin-siRNA complexed nanoparticles, ensured the delivery of siRNA in the neuronal cells of cerebral cortex ($p=0.0001$) and in the Purkinje cells of the cerebellum ($p=0.0001$) as compared to the untreated control. Other animals that received 0.25 mg/kg of scrambled biotin-siRNA showed faint staining in the neuronal cells of cerebral cortex ($p=0.006$), this is justified by the fact that dose A (0.25 mg/kg) was half the concentration of dose B (0.5 mg/kg). Whereas, animals that received 1 and 2 mg/kg of scrambled biotin-siRNA dose, did not show any staining in the tissue. The reason was interpreted, as while concentrating the nanoparticle formulation from a range of 10-20 ml solution to 30 µl before dosing, the process of concentrating led to clumping and aggregation of the nanoparticles, which resulted in increase in nanoparticles size and it could not penetrate the neurons. FIG. 10(II) represents the quantitative analysis of the tissues using ImageJ, which calculates the mean percentage area of the dark brown stained cells using image J software. Thus, this study determined that, under these experimental conditions, the optimal dose for the developed nanoparticles formulation administered intranasally was dose B at 0.5 mg/kg. In addition, these results indicated that the nanoparticle formulation can be used for the successful delivery of the biotin-siRNA with high efficiency and high target selectivity.

Figure 11A:
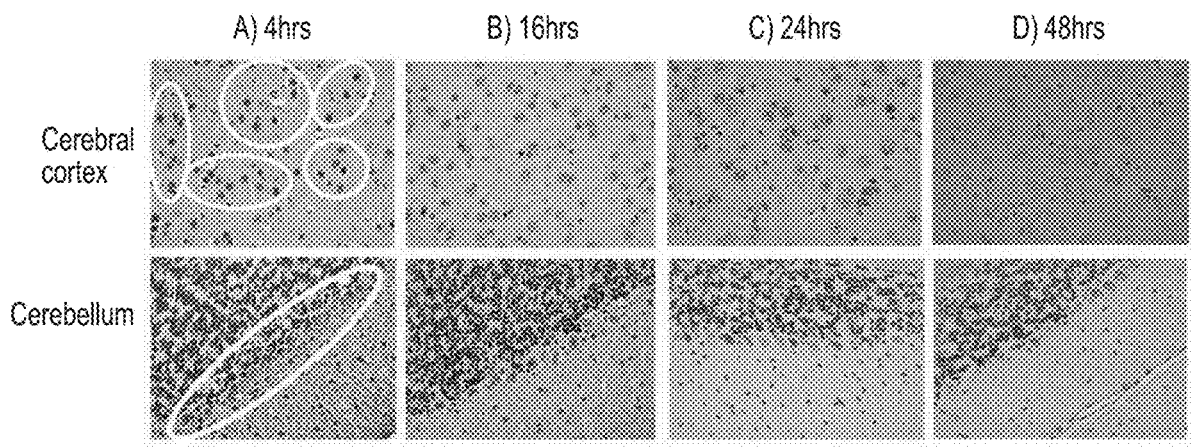
FIGS. 11A-11B represent histopathological images (cerebral cortex (first row) and cerebellum (second row)) with nanoparticles carrying 0.5 mg/kg of biotin-siRNA at different time points: 4 hrs, 16 hrs, 24 hrs and 48 hrs after the administration of the biotin-siRNA (FIG. 11A). The circled regions in column A, identified with DAB staining, indicate the presence of biotin-tagged scrambled siRNA in neurons delivered by nanoparticles. Magnification 400×.
Figure 11B:
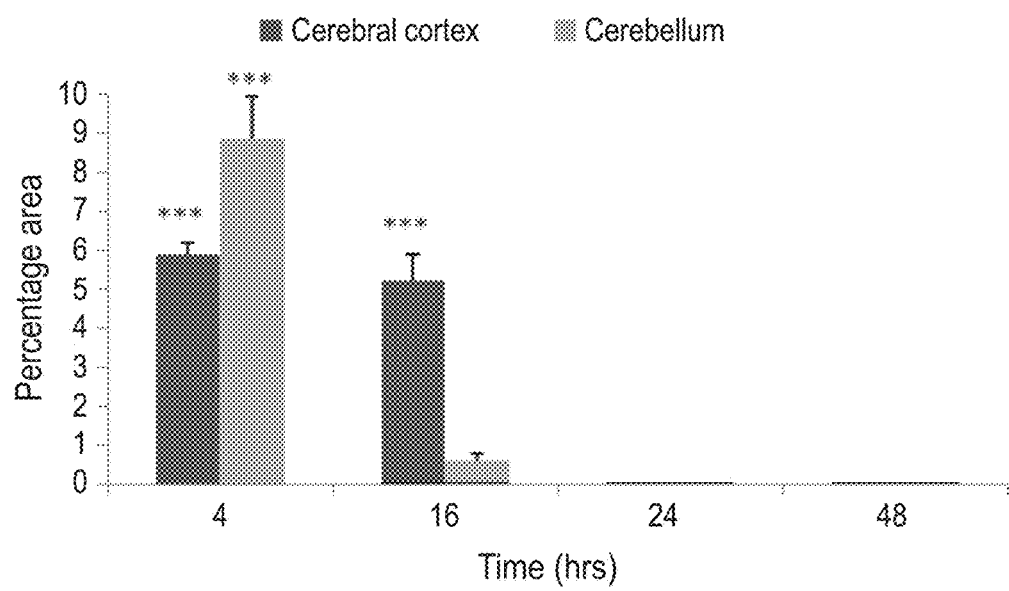

FIG. 11 (I) represents histopathological sections of brain tissue (cerebral cortex) of mouse having received dose B (as described in FIG. 10) at 0.5 mg/kg at different time points, (A) 4 hrs, (B) 16 hrs, (C) 24 hrs and (D) 48 hrs. As observed in the figure, the staining with dose 0.5 mg/kg shows significant dark brown staining in the pyramidal neurons of the cerebral cortex and Purkinje cells of the cerebellum ($p=0.0001$) at 4 hrs (A). The staining was observed only until 16 h in the cerebral cortex ($p=0.0001$) and faded thereof, with no staining observed at 24 and 48 h. The result was quantified using Image J as represented in FIG. 11 (II). The time dependent study was conducted to determine and monitor the expression of siRNA after being delivered by nanoparticle formulation via intranasal route of administration. These results indicate that, in these experimental conditions, the nanoparticle formulation containing 0.5 mg/kg siRNA was successfully delivered to neuronal cells within 4 hours. These results also indicate that the intranasally administered nanoparticle formulation is, under these experimental conditions, cleared after 16 hrs.

Figure 12A:
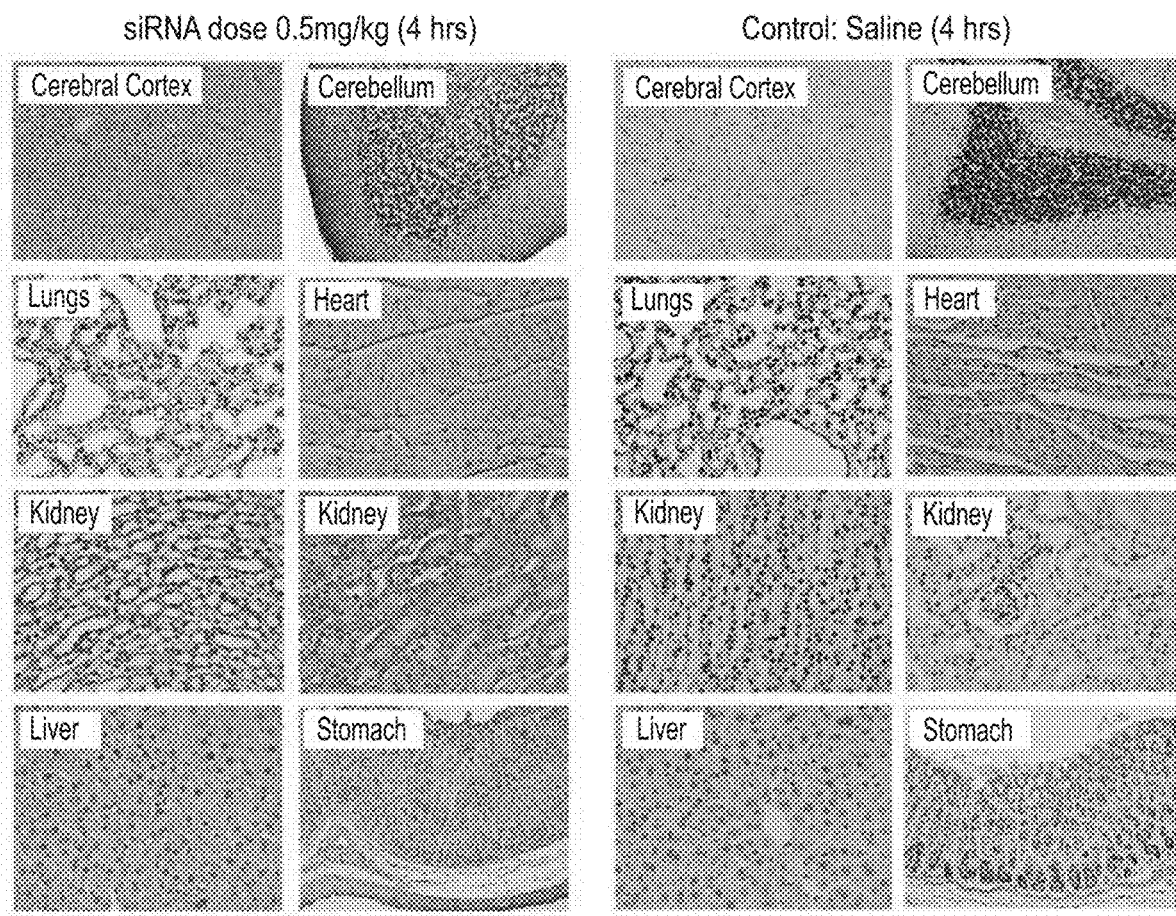
FIGS. 12A-12B represent biodistribution (through histopathological staining) of various organs collected 4 hrs following administration of the nanoparticle formulation containing biotin-siRNA dose at 0.5 mg/kg in animals.
Figure 12B:
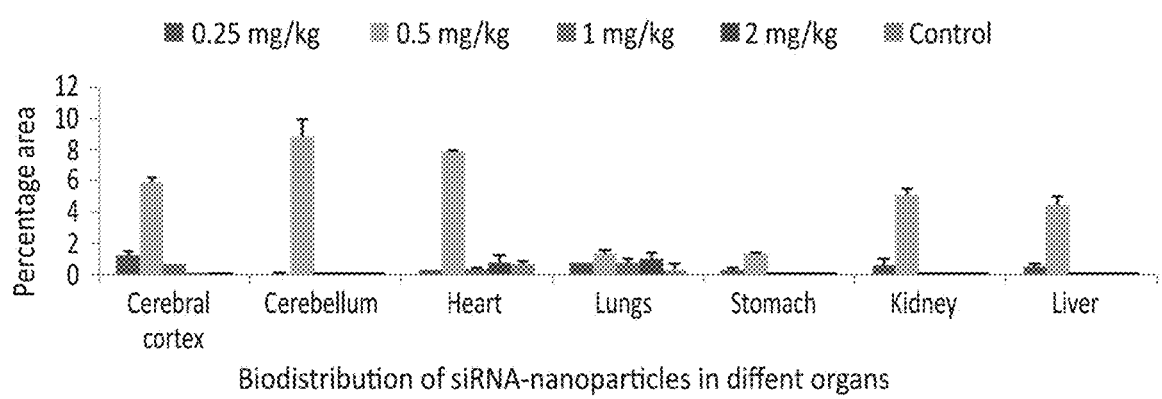
Figure 13A:
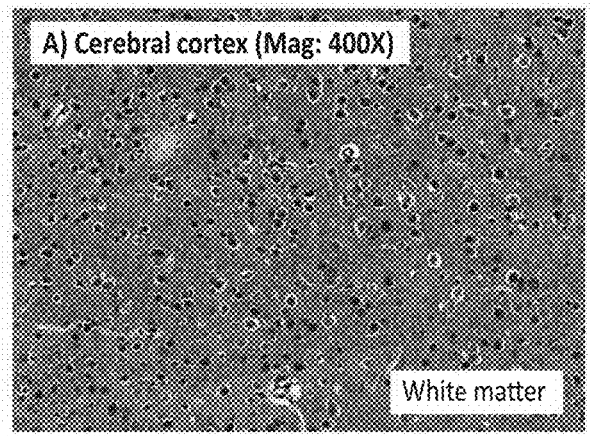
FIGS. 13A-13B represent enlarged DAB stained histopathological sections of cerebral cortex (FIG. 13A) and cerebellum (FIG. 13B) with nanoparticle formulation complexing biotin tagged scrambled siRNA at dose 0.5 mg/kg. The cerebral neurons in FIG. 13A and Purkinje cells in cerebellum in FIG. 13B show a clear brown staining indicating the presence and successful delivery of biotin tagged scrambled siRNA in these cells by nanoparticles administered via intranasal route. The brown color obtained by DAB staining in FIGS. 13A and 13B represents presence of biotin-tagged scrambled siRNA in neuronal cells of cerebral cortex and Purkinje cells of cerebellum respectively, as delivered by nanoparticles. Magnification 400×.
Figure 13B:
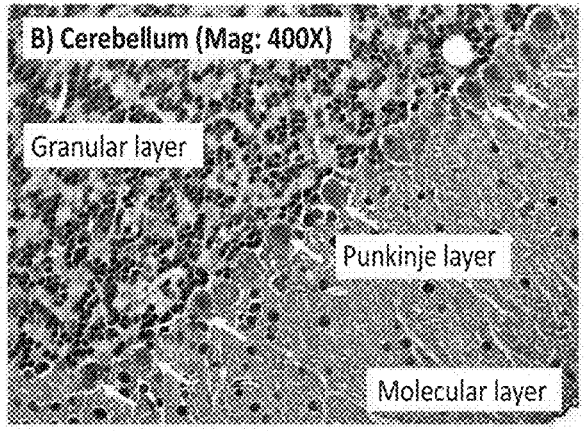
Figure 14A:
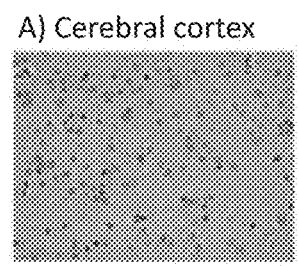
FIGS. 14A-14F represent histopathological images of various organ tissues collected 4 hrs following intranasal administration of multifunctional siRNA/nanoparticle formulation containing biotin-siRNA at a dose of 0.5 mg/kg. The tissues were stained with the TUNEL apoptosis assay. Results are shown for the cerebral cortex (FIG. 14A), cerebellum (FIG. 14B), heart (FIG. 14C), lungs (FIG. 14D), kidneys (FIG. 14E), liver (FIG. 14F) and stomach (FIG. 14G). As indicated in these images, the absence of TUNEL-specific staining represents no apparent cell toxicity/apoptosis in any of the tissues. Magnification 400×.
Figure 14B:
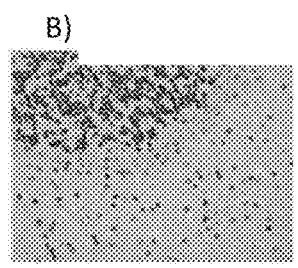
Figure 14C:
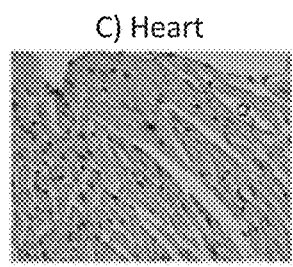
Figure 14D:
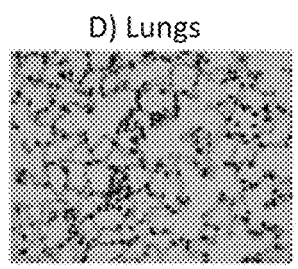
Figure 14E:
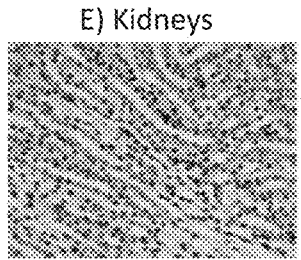
Figure 14F:
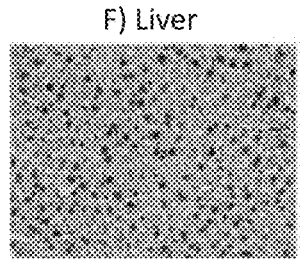
Figure 14G:
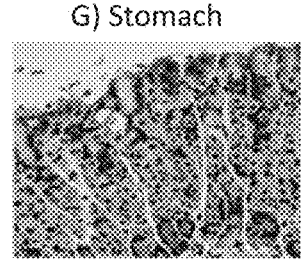

FIG. 12A represents histopathological sections of different organs with treatment dose B (as described in FIG. 10) comprising nanoparticle formulation at siRNA dose 0.5 mg/kg (left column) and control group with PBS (right column) after 4 hours. As observed in the figure, the staining in the brain tissue was highly significant with 0.5 mg/kg scrambled biotin-siRNA/nanoparticle dose in both cerebral cortex and cerebellum ($p=0.0001$) and also with 0.25 mg/kg but only in the cerebral cortex ($p=0.006$), as represented in FIG. 4B. The staining with biotin-siRNA/nanoparticle dose at 0.5 mg/kg was also observed to target heart sarcomeres ($p<0.01$), with significance as compared to other dose concentrations; 0.25 mg/kg ($p=0.403$), 1 mg/kg ($p=0.562$), 2 mg/kg ($p=0.999$) (FIG. 12 B). Renal cells in the medulla region of the kidney and hepatic cells also showed brown-colored staining in the cells, with 0.5 mg/kg of scrambled biotin-siRNA/nanoparticle formulation ($p=0.0001$) as compared to the untreated control (FIG. 4B). The glandular cells of the stomach and alveoli in lungs showed no significant difference as compared with the untreated control. Among all the concentrations of different treatment doses tested, the highest staining was observed with 0.5 mg/kg of scrambled biotin-siRNA/nanoparticle formulation in the cerebral cortex and cerebellum ($p<0.01$), when compared with staining in other organs, except the heart. FIG. 13 represents the enlarged view of cerebral cortex and purkinje cells. However, in the cerebral cortex, the anterior olfactory bulb, hippocampus, thalamus, hypothalamus were also found to be well stained.

As per the nanoparticle formulation of CS-PEG-TAT/MGF, the MGF peptide was used as targeting ligand for purkinje cells. The MGF peptide is a splice variant of IGF and has been shown to have affinity towards neuronal cells and myocardial tissues. Thus the staining in the heart could be the due to the affinity of MGF peptide targeting the heart sarcomeres. Following the intranasal route of administration, a fair amount of nanoparticles was expected to target lungs through the airway pathway. Renal, hepatic cells have been shown to have stained as compared to the control sections. It is to be noted that no staining was observed in any tissue sections at 24 hrs and 48 hrs time point. This could be due to the degradation of the biotin—siRNA molecule by that time and at 16 h, except brain tissues (cerebral cortex) no other tissue section was observed to have staining in the cells.

Cytotoxicity—TUNEL assay on animal tissues. Analysis of apoptotic cells in tissues was performed using Terminal deoxynucleotidyl transferase-mediated dUTP nick-end labeling (TUNEL) staining (Promega, Madison, Wis., USA) as per the manufacturer's protocol after a pretreatment procedure performed to block biotin-siRNA. In brief, the tissue sections in paraffin block were dewaxed in xylene and rehydrated in decreasing concentrations of ethanol and washed with PBS. The tissue sections were then incubated with Streptavidin-HRP reagent (Roche Diagnostics) for 10 minutes, washed in PBS. After which the sections were incubated with 3% $H_2O_2$ for another 10 minutes and again washed in PBS. This step was included to block biotin-siRNA already present in the neuronal cells and to avoid any false positive results. After this step, the protocol of TUNEL assay was performed as per the manufacturer's instructions. The tissue sections were counterstained with hematoxylin, washed in distilled water, dehydrated and mounted with permount (Vector laboratories; Burlingame, Calif., USA) to be observed under compound microscope (Leica DM500; Ontario, Canada) at ×400 magnification.

FIG. 14 represents histopathological sections of different organ tissues from animal receiving nanoparticle formulation containing biotin tagged scrambled siRNA as a dose at 0.5 mg/kg of animal weight, euthanized after 4 hrs. The tissues did not show any apparent staining in the cells, which confirms no toxicity/apoptosis of cells due to the administration or presence of the nanoparticle formulation.

Without wishing to be bound to theory, FIG. 15 represents a potential mechanism of cellular uptake of surface functionalized, nanoparticle through a targeted receptor-mediated endocytosis pathway, with endocytotic release from the endosome due to "proton sponge" effect. Following the endosomal disruption, the delivered therapeutic molecule gets released intra-cellularly.

Example IV—In Vivo Use of the Nanoparticles for the Treatment of Alzheimer's Disease Neurodegenerative diseases are characterized by progressive, age-related loss of specific subsets of neural cells, which lead to diverse clinical phenotypes depending on the underlying anatomical involvement. The etiology of neurodegenerative diseases is most often multifactorial, likely a result of gene—environmental interaction, which may lead diseases like Parkinson's, Alzheimer's, Huntington's, Amyotrophic lateral sclerosis (ALS) and Spinocerebellar Ataxia (SCA). These diseases tend to progress slowly over the time and generally target older population. Alzheimer's is the most common form of dementia, which is incurable and degenerative. It is predicted to affect 1 in 85 people globally by 2050. As per the 2008 clinical trial report, it is uncertain if any of the intervention strategies tested among 500 clinical trials, are likely to show promise for the identification and treatment of Alzheimer's disease (AD). The mean life expectancy of an individual is drastically reduced to 7 years after the onset of the disease. Currently, there is no cure available that can halt the progression of the disease. However, therapies and drugs are available in the markets that merely mitigate the symptoms of the disease.

Alzheimer's disease is characterized by the presence of misfolded protein in the form of senile plaques and neurofibrillary tangles in the brain. The senile plaques are composed of dense, insoluble deposits of amyloid-beta peptide in and around the neuron. These peptides are the fragment of a larger transmembrane protein called amyloid precursor protein (APP). APP is essential for neurons growth survival and post injury repair. The formation of amyloid-beta peptides is initiated by a sequential cleavage of APP by an enzyme, protease beta-secretase, also known as BACE1 (beta site APP cleaving enzyme) and then by a gamma-secretase, an aspartyl protease complex, which generates toxic C-terminal fragments inside the cell and releases a fragment called amyloid-beta peptide extra cellularly. Neurofibrillary tangles are aggregates of the microtubule-associated tau protein which has become hyperphosphorylated and accumulate inside the cells. The underlying pathological mechanism of AD is still unknown but the accumulation of amyloid-beta peptides is thought to be the central triggering event of the disease, which is believed to disrupt the cell's calcium ion homeostatis, leading to apoptosis. Amyloid-beta is also known to accumulate in the mitochondria of affected cells and inhibit certain enzyme functions that further inhibit the utilization of glucose by neurons. Moreover, alteration in the distribution and expression of brain derived neurotrophic factors (BDNF) has also been observed to be associated with AD.

The identification of these biological and pathological abnormalities triggered the studies on recognizing the genes responsible for causing inherited forms of AD. On such form is autosomal dominant familial Alzheimer's disease, which is caused due to the mutations in the APP and components of gamma-secretase (Presenilins 1 and 2) that lead to increased production of amyloid-beta 2 protein, the main component of senile plaques. Several transgenic animal models have been developed based on various genetic mutations to understand the aetiology and possible pathological mechanism of the disease and to investigate various therapeutic options.

Advancement in RNAi therapy has facilitated the understanding of pathobiological mechanisms of the disease with most of the researches focusing on phenotype rescue due to dominantly acting mutant genes and loss-of function analysis. Based on the aetiology of the AD, the key targets for RNAi therapy are assumed to be APP, BACE and gamma-secretase and tau, which can eliminate the production of toxic C-terminal fragments and amyloid-beta peptides. siRNAs has been delivered to the central nervous system both naked or with the help of some transfection reagents in-vivo, targeting different molecular targets in different parts of the nervous system, showing effective gene silencing. Direct doses of siRNAs administered intrathecally or intracerebroventricularly pose a widespread inhibition of molecular targets that are broadly expressed in different parts of the brain but may also lead to off-targeting. A significant limitation is the inability of the therapeutic molecules to cross the blood-brain barrier and other physiological barriers. Thus the application of a novel therapeutic modality also depends on the development of an efficient and clinically feasible means of administration. Though, various siRNA delivery strategies have been explored, but they have not proved to be as effective and have created concerns with safety issues, thus a polymeric approach of delivering siRNA molecules, which is target specific, multifunctional, biodegradable and biocompatible is more appealing. We have developed a self-assembled, functionalized receptor targeting nanoparticles from chitosan that are biodegradable and biocompatible in nature and perform target specific delivery of siRNA, when delivered intranasally to the cerebral cortex of the brain.

Materials. Chitosan (M.W. 7 to 10 KDa) with a viscosity of 5 to 20 cP (at room temperature) and a degree of deacetylation of 80.0% was purchased from Wako (Richmond, Va., USA). Polyethylene glycol monomethyl ether (mPEG): medium molecular weight (2 000 Da), phthalic anhydride, pyridine, toluene, hydrazine monohydrate, succinic anhydride, ethanethiol, aluminium chloride, sodium tripolyphosphate (TPP), and glacial acetic acid of analytical grade are obtained from Sigma (Oakville, ON, Canada). Anhydrous N,N-Dimethylformamide (DMF), 1-ethyl-3-[3-dimethylaminopropyl]carbodiimide hydrochloride) (EDC), 4-(Dimethylamino) pyridine (DMAP), sodium hydroxide (NaOH), methanol, diethyl ether, chloroform, concentrated hydrochloric acid were obtained from Thermo Fisher Scientific (Ottawa, ON, Canada). Thionyl chloride ($SOCl_2$) is obtained from VWR (Mississauga, ON, Canada). TAT peptide ($NH_2$-RKKRRQRRR-$NH_2$) (SEQ ID NO: 4) M.W. 1339.63 and MGF peptide ($NH_2$-YQPP-STKNTKSQRRKGSTFEEHK-$NH_2$) (SEQ ID NO: 1) M.W. 2848.14, were synthesized by Sheldon Biotech, McGill University. siRNA targeting PSN1 (Accession #: NM_000021.3) targeting sequence: 5' AAG GUC CAC UUC GUA UGC UGG (SEQ ID NO: 5) was synthesized from Dharmacon (Lafayette, Colo., USA).

Synthesis of peptide tagged PEGylated chitosan polymer and nanoparticles preparation. The polymer CS-PEG-TAT/MGF was synthesized as described in Example I. The nanoparticles were prepared from the chemically modified polymer (CS-PEG-TAT/MGF). The formation of nanoparticles involved ionic-gelation method, as previously described by Calvo et al. (1997). The optimization of nanoparticles on the basis of size and surface charge has been previously performed and is published elsewhere (Malhotra et al., 1999). In brief, 0.5 mg/ml of chemically modified polymer was crosslinked with 0.7 mg/ml of sodium tripolyphosphate (TPP), complexing 2 µg/ml of siRNA.

Animal model. Four weeks old Alzheimer's transgenic mice model Tg(APPSwFILon, PSEN1*M146L*L286V) 6799Vas were purchased from MMRC facility in Jackson Laboratory (Bar Harbor, Me., USA). These transgenic mice over-express both mutant human APP(695) with the Swedish (K670N, M671L), Florida (I716V), and London (V717I) Familial Alzheimer's Disease (FAD) mutations and human PS1 harboring two FAD mutations, M146L and L286V. This transgenic mice model was chosen as it over expresses amyloid-beta 42 protein in cerebral cortex and hippocampus, resulting in amyloid plaque pathology as early as 2 months of age. Other characteristic features include; reduced synaptic markers, increased p25 levels and neuron loss.

The animals were housed in an environment with controlled temperature (22° C.), humidity, and a 12 h light/dark cycle at McGill's Animal care facility. The animal experiment was conducted as per the protocol approved by the Animal care committee at McGill University (Montreal, QC, Canada). Standard mouse chow pellets and water were supplied ad libitum. Animals were acclimatized for two weeks before the start of the experiment. The animals were divided in two groups. The first group (n=4) received siRNA against PSN1 gene and the control group (n=4) received no treatment at all. The treatment began at 6 weeks of animal age. The siRNA dose administered through nanoparticles was 0.5 mg/kg of animal weight. Prior to the dose administration the animals were anesthetized with isoflurane, gas anesthesia, as per the animal use protocol of McGill University. The treatment dose was administered daily, intranasally, for a total of 3 weeks. All the animals were sacrificed at the end of 3 weeks. Brain was harvested for PSN1 mRNA quantification.

Percentage mRNA knockdown by siRNA delivered through the nanoparticles. To further validate the knockdown results of the endogenous PS1 expression in the treatment group, when compared to the control, a quantitative real time PCR was performed. Briefly, the brain tissue excised at the end point was preserved in RNAlater® or RNALATER® RNA stabilization reagent from Qiagen and stored at −20° C., until use. The total RNA was extracted using RNAeasy® or RNAEASY® Lipid tissue mini kit from Qiagen and the total RNA will be quantified using Nanodrop 2000 spectrophotometer. The reverse transcription on total RNA was performed to obtain cDNA using a QuantiTect™ Reverse Transcription kit or QUANTITECT™ REVERSE TRANSCRIPTION KIT™ from Qiagen. A quantitative real time PCR was performed using MBI Evolution Evagreen™ Master Mix or EVOLUTION EVAGREEN MASTER MIX™ following the manufacturer's protocol (MBI, Montreal, Canada) on ECO RT PCR machine from Illumina. The relative expression levels of the targeted gene were compared with the housekeeping gene GAPDH. The primer sequences used were as follows:

```
PSN1:
F
                                    (SEQ ID NO: 6)
5'-CCGAAATCACAGCCAAGA-3';

R:
                                    (SEQ ID NO: 7)
5'-CATTCACAGAAGATACCAAGAC-3'.

GAPDH,
F:
                                    (SEQ ID NO: 8)
5'-TAAAGGGCATCCTGGGCTACACT-3';

R:
5'-
                                    (SEQ ID NO: 9)
TTACTCCTTGGAGGCCATGTAGG-3'.
```

The PCR was run for 40 cycles with a 95° C. denaturing step (15 s), a 56° C. annealing step (1 min), and a 72° C. extension step (15 s), plus final incubation at 72° C. for 10 min.

Figure 16:
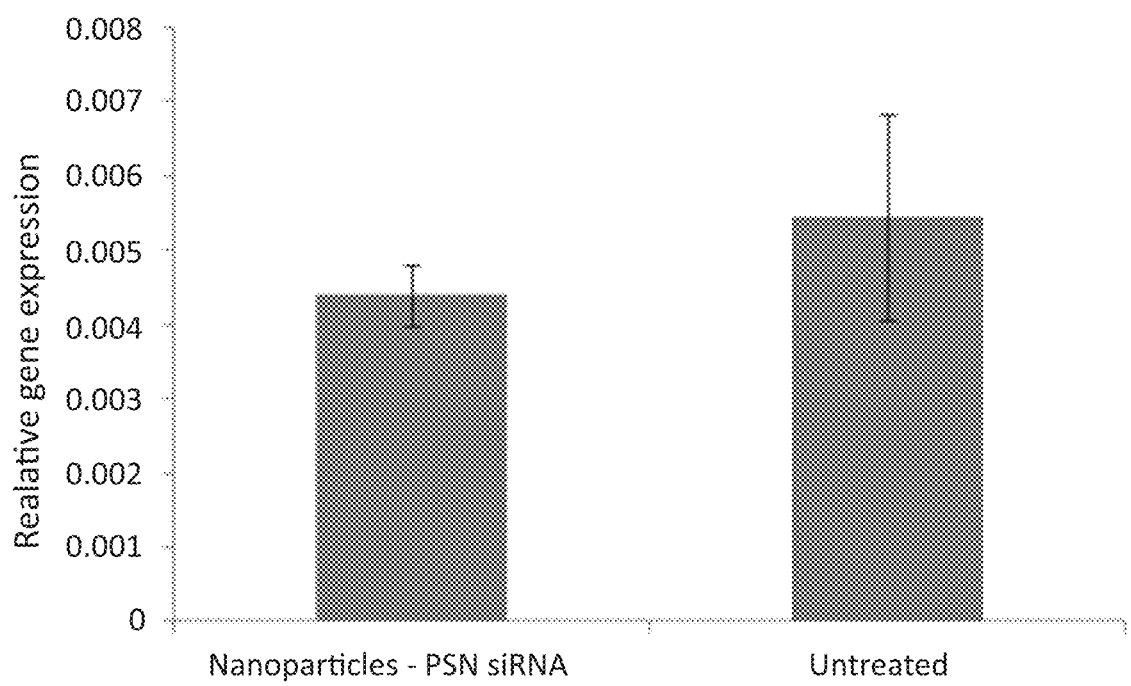
FIG. 16 shows the results associated with the percentage PSN1 gene knockdown upon administration of the nanoparticle composition. Results are shown as relative expression (in function of GADPH) of PSN1 for animals treated with the nanoparticles bearing a PSN1 siRNA (left column) and for control (untreated) animals (right column). The results indicate a 21.34% reduction in PSN1 gene expression with nanoparticles carrying siRNA against PSN1 gene, when compared with untreated control. The graph shows a representative result (average of n=4±S.E.).
Figure 17A:
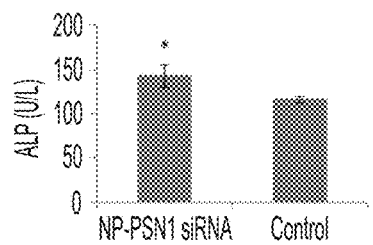
FIGS. 17A-17E show the result of serum analysis performed on animals treated with the nanoparticles bearing the PSN1 siRNA or a control. Results are shown for ALP levels (U/L) (FIG. 17A), AST/ALT levels (U/L) (FIG. 17B), CRP-5 (mg/L) (FIG. 17C), urea (mmol/L) (FIG. 17D), CRE (μmol/L) (FIG. 17E) and UA (μmol/L) (FIG. 17F) in function of treatment. The graphs show representative results (average of n=4±S.E.). *P<0.05 was considered significant based on student t-test.
Figure 17B:
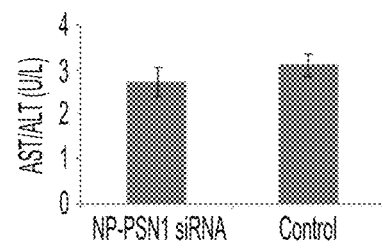
Figure 17C:
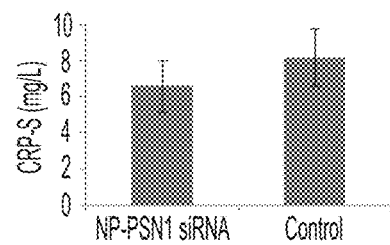
Figure 17D:
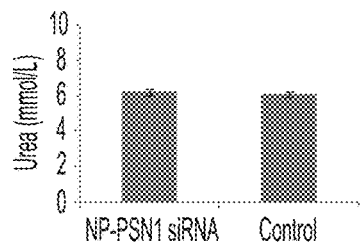
Figure 17E:
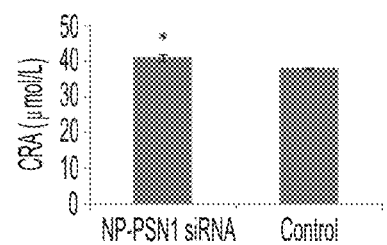
Figure 17F:
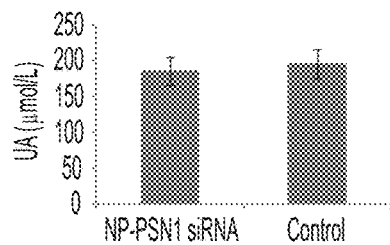

Evaluation of percentage gene knockdown of PSN1 gene, silenced by siRNA delivered intranasally via novel receptor-targeted nanoparticles. The PSN1 gene knockdown was evaluated by extracting total RNA form the brain tissues, then reverse transcribing it to form a cDNA and then running a Real-Time PCR on cDNA using primers specific for PSN1 gene. The percentage gene knockdown of PSN1 gene was evaluated by comparing the treatment group with the untreated control. As represented in FIG. 16, a 21.34% of gene knockdown was achieved in the treatment group (n=4) that received siRNA against PSN1 gene, complexed with nanoparticles, as compared to the untreated control (n=4). Though not statistically significant (p=0.162), these results propose a promising approach of delivering siRNA using receptor-targeted nanoparticles via intra-nasal route for brain targeting.

Systemic safety and toxicity of novel siRNA-nanoparticle formulation. Safety markers were analyzed from the serum collected from the animals that received 0.5 mg/kg of PSN1-siRNA, complexed with peptide tagged PEGylated chitosan nanoparticles. The liver function and toxicity tests were performed using alkaline phosphatase (ALP) and aspartate aminotransferase/alkaline aminotransferase (AST/ALT) respectively. The results for ALP though show a significant difference between the treatment and control group (FIG. 17, p=0.036) but had values that fall in the normal range of 44 to 147 IU/L. For AST/ALT, the results indicate no significant difference between the treatment and the control group (FIG. 17, p=0.379). Another test performed was CRP, which is an indicative of systemic inflammation the results showed no significant difference between the treatment and the control (FIG. 17, p=0.472). Urea, CRE and UA tests were performed indicating the renal function in animals. The results indicate no significant difference in urea (FIG. 17, p=0.535) and UA (FIG. 17, p=0.737) levels, however the creatinine was found to be elevated in the treatment group as compared to the control (FIG. 17, p=0.025), but the values in both the groups were all found to be in the normal range i.e. 38.13 to 91.5 μmol/L.

Example V—In Vivo Use for Treating Cancer

Cancer is characterized by uncontrolled growth of group of cells that infest adjacent tissues and often metastasize to other organs via lymphatic system or blood stream. Cancer is primarily caused by environmental factors (90-95%) and few with genetic (5-10%). The uncontrolled growth of group of cells in the case of cancer is usually triggered by malfunctioning of the genes that manipulate cell's growth and differentiation. Typically the alteration in cell growth promoting, oncogenes and cell division inhibiting, tumor suppressive genes lead to the formation of cancer cells. The genetic causes of cancer are usually due to gain or loss of an entire chromosome due to errors in mitosis or changes in nucleotide leading to mutations in the genomic DNA. Depending on the stage of the cancer the treatment options available include surgical removal, chemotherapy with anticancer drugs, such as 5-fluorouracil, oxaliplatin and leucovorin, radiation therapy, immunotherapy and hormone block therapy with drugs like cetuximab and panitumumab. However, it has been shown that cancers with genetic origin are not benefited with these chemotherapies. Moreover, the toxicity and side effects has severely limited the safety and effectiveness of these methods. One of the target proteins in cancer therapy is PLK1, which is a serine/threonine kinase, a key regulator for mitosis in mammalian cells. It is required for centrosome maturation, bipolar spindle formation, and chromosomal segregation and is also associated with microtubules and centrosomes at various stages of mitosis. PLK1 is considered as a proto-oncogene, which over-expresses in a variety of human cancers. PLK1 is directly associated with p53, a tumor suppressor protein. PLK1 on interaction with p53 inhibits its transactivation activity and pro-apoptotic activity, leading to uncontrolled proliferation of cells. Lately, inhibition of PLK1 with antibodies, antisense oligonucleotides (ASO's), small interfering RNA (siRNA) or dominant negative mutants that suppress the tumor growth by causing increased apoptosis has gained much interest as a therapeutic option to treat tumor diseases. Although, antineoplastic drugs have shown great success as a treatment for cancer therapy, many carcinomas are resistant to these agents and thus, chemotherapy with these agents has become a major restriction at an advanced cancer stage. Therefore, siRNAs targeted against proliferation-associated signal transduction pathways, which can halt the tumor progression in animal models is emerging as an appealing approach. For cancer therapy, a receptor-targeted nanoparticles for in vivo delivery of siRNA has been developed. The target specificity of the nanoparticles is attributed to a peptide that guides the nanoparticle system carrying siRNA to specific tissue, when administered via systemic route. The advantage of using peptide based tumor targeting is their rapid clearance from the blood because of their small size and lack of immunogenicity. The identification of peptides for tumor-specific targeting has been facilitated by a technology called, phage display library, which takes into account the ability of filamentous bacteriophage to present large number of peptides and proteins on their surface, allowing these specific peptide sequences to bind to the target specific tumors or cell types. This method for identification of specific binding ligands has found wide application in isolating peptides that has high binding affinity towards cancer cells. The conjugation of these peptides to conventional chemotherapeutic drugs, diagnostic/imaging molecules and nanoparticles will enable their delivery in low dose with effective targeting. In this study, the peptide CP15 with a sequence $NH_2$-VHLGYAT-$NH_2$ (SEQ ID NO: 2), which was identified by the technology of phage displayed library was used. CP15 peptide has shown to be the most effective peptide targeting colon tumor cells but not the normal human intestinal epithelial human cells. The novel receptor-targeted nanoparticle formulation developed in this study were tagged with CP15 peptide as a ligand that will guide the nanoparticles to selectively target the tumor tissue expressing receptors for CP15 peptide in a mouse xenograft model of colon cancer developed from SW480 epithelial colon cancer cells. This illustrates the potential of using these novel receptor-targeted nanoparticles to be used in future for cancer therapy.

Materials. Chitosan (M.W. 50 KDa to 190 KDa) with viscosity 20 to 300 cP (at room temperature) and degree of deacetylation of 75 to 85% was obtained from Sigma (Oakville, ON, Canada). Polyethylene glycol monomethyl ether (mPEG): medium molecular weight (2 000 Da), phthalic anhydride, pyridine, toluene, hydrazine monohydrate, succinic anhydride, ethanethiol, aluminium chloride, sodium tripolyphosphate (TPP), agarose, ethidium bromide (10 mg/ml) and glacial acetic acid of analytical grade are obtained from Sigma (Oakville, ON, Canada). Anhydrous N,N-Dimethylformamide (DMF), 1-ethyl-3-[3-dimethylaminopropyl]carbodiimide hydrochloride) (EDC), 4-(Dimethylamino) pyridine (DMAP), sodium hydroxide (NaOH), methanol, diethyl ether, chloroform, concentrated hydrochloric acid were obtained from Thermo Fisher Scientific (Ottawa, ON, Canada). Thionyl chloride ($SOCl_2$) is obtained from VWR (Mississauga, ON, Canada). CP15 ($NH_2$-VHLGYAT-$NH_2$) (SEQ ID NO: 2) M.W. 758.3, were synthesized by Sheldon Biotech, McGill University. Pre-cast NUPAGE™ 4 to 12% Bis-Tris gels, Nupage MES running buffer, NUPAGE™ transfer buffer, NUPAGE™ LDS sample buffer (4×), nitrocellulose membrane 0.45 μm, blotting filter paper and Magic Mark™ or MAGIC MARK™ (1 Kb) protein ladder were obtained from Invitrogen (Burlington, ON, Canada). Scrambled/non-targeting (NT) siRNA tagged with biotin, and PLK siRNA (h) with sequence; PLK (sense strand)-5' AGAmUCACCCmUCCUmUAAAmUAUU 3' (SEQ ID NO: 10) and PLK (antisense strand)-5' UAUUUAAmGGAGGGUGAmUCUUU 3' (SEQ ID NO: 11) from Dharmacon (Lafayette, Colo., USA), where "m" represents 2'Omethylated nucleotide. Primary antibodies; PLK1 (F-8) mouse monoclonal antibody, β-Actin (C-4) mouse monoclonal antibody, probed with secondary antibodies; (HRP)-conjugated goat antimouse antibody. All the antibodies were procured from Santacruz Biotechnology (Santa Cruz, Calif., USA).

Synthesis of peptide (CP-15) tagged PEGylated chitosan polymer. The polymer CS-PEG-CP15 was synthesized as described in Example I. The modified polymer was characterized and analyzed using $^1$H (Mercury 400 and 500 MHz NMR) and Transmission Electron Microscopy (Philips EM410 TEM).

Preparation of novel polymeric nanoparticles from CP-15 tagged PEGylated chitosan polymer. Nanoparticles were prepared from the chemically modified polymer (CS-PEG-CP-15). The formation of nanoparticles involved ionic-gelation method, as previously described by Calvo et al. (1997). The optimization of nanoparticles on the basis of size and surface charge has been previously performed and is published elsewhere (Malhotra et al., 2009). In brief, 0.5 mg/ml of chemically modified polymer was crosslinked with 0.7 mg/ml of sodium tripolyphosphate (TPP), complexing 8 µg/ml of siRNA. The characterization of nanoparticles size and dispersivity was analyzed by transmission electron microscopy (TEM) and the siRNA loading efficiency was determined by gel retardation assay.

Animal study and in vivo tumor induction. Six weeks old mice Balb/c nude mice, weighing 15 to 20 g were purchased from Charles River Laboratories (Wilmington, Mass., USA) and housed in an environment with controlled temperature (22° C.), humidity, and a 12 h light/dark cycle at McGill's Animal care facility. The animal experiment was conducted as per the protocol approved by the Animal care committee at McGill University (Montreal, QC, Canada). Standard mouse chow pellets and water were supplied ad libitum. Animals were acclimatized for a week before the start of the experiment. For tumor induction, animals were subcutaneously inoculated with 100 µl of SW480 colon cancer cells ($2\times10^6$) mixed with an equal volume of MATRIGEL™ (BD). The treatment began after the tumor reached a volume of 100 mm$^3$. The animals were randomized into 4 treatment groups (n=7) to receive treatment formulations. The following treatment formulations: 1) CS-PEG-CP15 with PLK1 siRNA; 2) CS-PEG-CP15 with non-targeting (NT) siRNA, 3) PLK1 siRNA alone and 4) Untreated control. In each treatment group the animals received a total siRNA dose of 0.5 mg/kg. 100 µl of treatment formulations were administered thrice a week via intra-peritoneal injections for a period of 2 weeks.

Histopathological analysis to identify siRNA delivered via novel nanoparticles in tumor tissue. One animal from each treatment group was euthanized by $CO_2$ asphyxiation, after 4 hours of first dose administered via intra-peritoneal route. Brain, Lungs, Heart, Kidney, Spleen and Liver were harvested and kept at 4° C. in 10% phosphate buffered formalin for 48 h. After which the tissues were trimmed to 3 mm thick sections and stored at 70% ethanol in histology cassettes. The tissues were paraffin embedded and processed into 4 µm thick section on slides at the histology core facility (The Rosalind and Morris Goodman Cancer Research Centre, McGill University). The tissue section on slides were stained with Vectastain Elite ABC™ kit (Vector laboratories; Burlingame, Calif., USA) as per the manufacturer's protocol and Diaminobenzidine (DAB) was used as a substrate to assess the presence of biotin, which was used as a tag on siRNA for histology identification purposes. Hematoxylin was used as a counterstain and slides were mounted with PERMOUNT™ (Vector laboratories; Burlingame, Calif., USA) and observed under compound microscope (Leica DM500; Ontario, Canada) at ×400 magnification.

RNA extraction and QPCR to determine percentage gene knockdown by siRNA targeted against PLK1 gene delivered through novel nanoparticles. To further validate the knockdown effects of endogenous PLK1 expression after nanoparticles based siRNA delivery against PLK, a quantitative real time PCR was performed. Briefly, the tumor tissues excised at the end point were preserved in RNAlater® RNA stabilization reagent from Qiagen (Toronto, ON, Canada) and stored at −20° C. The total RNA was extracted using RNeasy® Plus mini kit from Qiagen, following the manufacturer's protocol. The total RNA was quantified using Nanodrop 2000 spectrophotometer from Thermo Scientific (Rockford, Ill., USA). Reverse transcription was performed to obtain cDNA from 1 µg of total RNA using a QuantiTect™ Reverse Transcription kit or QUANTITECT™ REVERSE TRANSCRIPTION KIT™ from Qiagen. Following that quantitative real time PCR was performed using MBI Evolution Evagreen Master Mix™ or EVOLUTION EVAGREEN MASTER MIX™ following the manufacturer's protocol (MBI, Montreal, Canada) on ECO RT™ PCR machine from Illumina (San Diego, Calif., USA). The relative expression levels of PLK1 gene were normalized with the housekeeping gene GAPDH. The primer sequences used were as follows:

```
PLK1
Plk1,
                                    (SEQ ID NO: 12)
5'-GGCAACCTTTTCCTGAATGA-3' and
                                    (SEQ ID NO: 13)
5'-AATGGACCACACATCCACCT-3';

GAPDH,
                                    (SEQ ID NO: 14)
5'-TAAAGGGCATCCTGGGCTACACT-3'
and
                                    (SEQ ID NO: 15)
5'-TTACTCCTTGGAGGCCATGTAGG-3'.
```

The PCR was run for 30 to 40 cycles with a 95° C. denaturing step (5 s), a 60° C. annealing step (15 s), and a 72° C. extension step (15 s), plus final incubation at 72° C. for 10 min.

Protein expression after siRNA delivered through novel nanoparticles. After 2 weeks of treatment, the animals were sacrificed as per the approved protocol by McGill University and the tumor tissues were harvested and preserved at −20° C. in ALL PROTECT TISSUE REAGENT™ from Qiagen (Toronto, ON, Canada). The tissue samples were sliced into small pieces and homogenized using POWERGEN MODEL 125™ Homogenizer from Fisher Scientific (Ottawa, Ontario, Canada) at 26 300 rpm in 2 mL of ice cold RIPA buffer (20 mM Tris pH 8, 150 mM NaCl, 5 mM EDTA, 1% Nonidet P-40, 0.1% SDS, 10.0% Glycerol, 10 mM $Na_2HPO_4 \cdot 7H_2O$, 1% Sodium deoxycholate) containing phenylmethylsulfonyl fluoride (PMSF) and protease inhibitor cocktail from Roche Diagnostics (Laval, QC, Canada). The crude extract was incubated on ice for 30 minutes and centrifuged at 10 000×g for 10 minutes at 4° C. to remove tissue debris. The supernatant was collected and the protein concentration was determined using Pierce® BCA Protein assay kit from Thermo Scientific (Rockford, Ill., USA). Briefly, aliquots containing 100 µg of protein were heated at 70° C. for 15 minutes with Nupage LDS sample buffer supplemented with 100 mM DTT. The proteins were fractionated on precast NuPAGE® 4 to 12% Bis-Tris Gel from Invitrogen (Ontario, Canada) at 200 V for 35 minutes in MES SDS running buffer. Magic Mark™ 1 Kb protein ladder was used as a standard. The gel was electrophoretically transferred to 0.45 µm pore size Novex® nitrocellulose membrane using Nupage transfer buffer on a Novex® Semi-Dry blotter (Invitrogen, ON, Canada). After transfer the nitrocellulose membrane was incubated for 1 hr in 5% non-fat powdered milk in Tris buffered saline (TBS) buffer supplemented with 0.2% Tween 20. The membrane was then incubated overnight at 4° C. with mouse PLK (F-8) monoclonal antibody (1:100 dilution). The next day the membrane was washed thrice with TBST for 15 minutes each, and then incubated with (HRP)-conjugated goat antimouse IgG secondary antibody (1:2,000 dilution). The membrane was again washed thrice with TBST followed by detection of signal with chemiluminescent agents (ECL, Amersham) from GE healthcare. The bound antibody was visualized using autoluminography. To control the protein loading, the membrane was reprobed with primary mouse monoclonal β-Actin (C-4) antibody (1:1 000) with an overnight incubation at 4° C., followed by subsequent three washes in TBST and detection with HRP-conjugated goat anti-mouse IgG secondary antibody (1:2 000) and development with chemiluminescent agents as described earlier. The protein band intensities were quantified using IMAGE J™ software.

Serum collection and analysis. Serum was collected through jugular vein just before the end-point using a sterile 23 G/25 mm needle and approximately 200 µl of blood was collected in Microtainer® serum separator tubes (Becton Dickinson, N.J., USA). The blood was allowed to clot at room temperature for 30 minutes and subsequently placed on ice until centrifugation. Serum was separated by low-speed centrifugation at 3600 rpm for 8 min at 4° C. The separated serum was frozen at −85° C. until analysis. Serum was used to test C-reactive protein (CRP) and liver function tests such as alanine aminotransferase (ALT) and aspartate transaminase (AST) using a conventional enzymatic method on Hitachi 911 automated clinical chemistry auto-analyzer (Roche Diagnostics, USA).

Statistical analysis. Statistical analysis was carried out using GRAPHPAD PRISM™ version 5.0 for windows (GraphPad software, San Diego, Calif.). Values are expressed as means±Standard Error. The statistical comparison between treatment groups was performed using ANOVA Tukey's test. P values<0.05 were considered significant.

Figure 18:
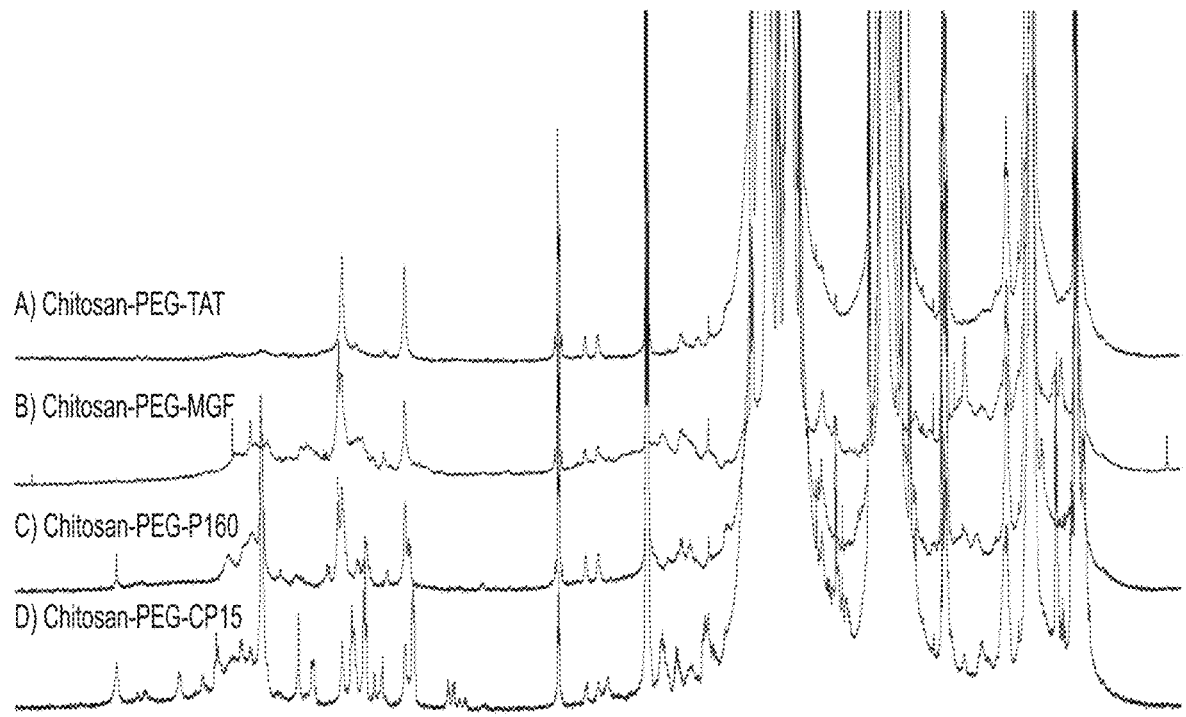
FIG. 18 shows $^1$H NMR spectra of Chitosan-PEG-TAT (CS-O-PEG-CONH-TAT) (plot A), Chitosan-PEG-MGF (CS-O-PEG-CONH-MGF) (plot B), Chitosan-PEG-P160 (CS-O-PEG-CONH-P160) (plot C) and Chitosan-PEG-CP15 (CS-O-PEG-CONH-CP15) (plot D). The multiple peaks of oxymethyl groups in PEG at δ 3.3 to 3.7 cover over the signals of pyranose ring of chitosan. The multiple peaks at δ 6.0-9.0 belong to the peptide sequences respectively.

Synthesis of CP-15 tagged PEGylated chitosan polymer and preparation of nanoparticles. The peptide-tagged PEGylated chitosan polymer was synthesized following a series of chemical reactions as represented in FIG. 1. Each intermediate step and the final product of the synthesis were characterized for the functional group modification and substitution by FTIR and $^1$H NMR as optimized in Malhotra et al. (2009). FIG. 18 illustrates the NMR spectra of the final product obtained (CS-PEG-CP15) after the synthesis. The multiple peaks of oxymethyl groups in PEG at δ 3.3 to 3.7 cover over the signals of pyranose ring of chitosan in the spectra. The weak and broad peak at δ 4.3-4.5 are from the protons of —NH—CH(CH$_2$)—CO— in CP-15 peptide. The multiple peaks at δ 6.0-9.0 belong to the CP-15 peptide sequence.

Figure 19:
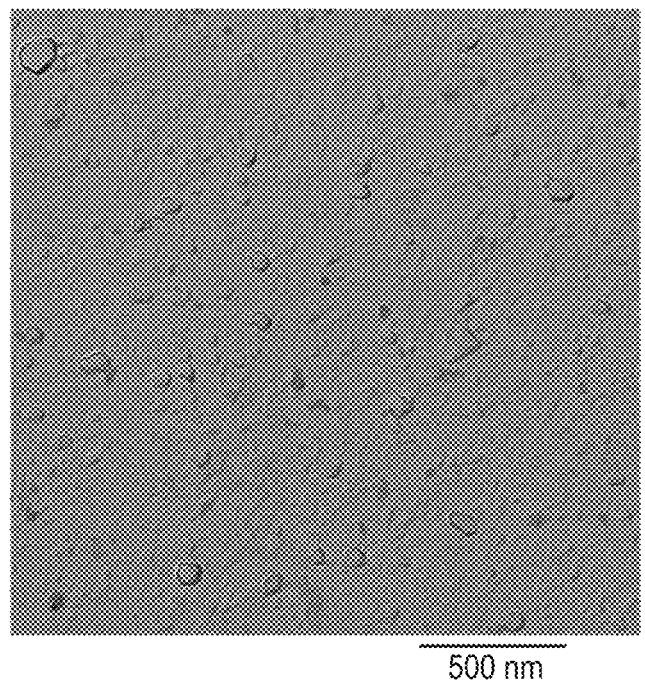
FIG. 19 shows transmission electron microscopy (TEM) image of peptide-tagged pegylated chitosan nanoparticles complexing siRNA. Magnification at 95 800×. Scale bar: 500 nm. The average size of the nanoparticles ranged from 100 to 200 nm.
Figure 20:
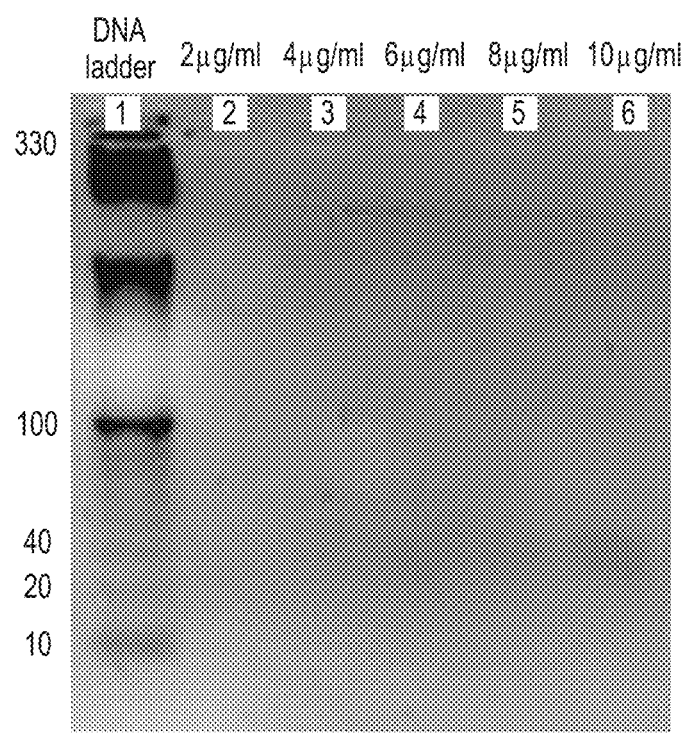
FIG. 20 shows gel retardation assay results to evaluate the maximum gene (siRNA) loading efficiency of nanoparticles. Lane 1 represents a 10 bp DNA ladder used as a reference. Lane 2 represents 2 μg/ml, lane 3 represents 4 μg/ml, lane 4 represents 6 μg/ml, lane 5 represents 8 μg/ml and lane 6 represents 10 μg/ml of siRNA dose complexed with the nanoparticles. The results suggest that 8 μg/ml is the optimal amount of siRNA to be complexed with the nanoparticles.

Characterization of nanoparticles. Nanoparticles were prepared following an ionic gelation scheme, wherein the cationic polymer complexes the anionic molecule due to electrostatic interaction. FIG. 19 represent nanoparticles as observed under TEM. The nanoparticles obtained were polydispersed and ranged from 100 to 200 nm in size. The polydispersivity observed in nanoparticles size depends on the average molecular weight of the polymer used. Molecular weight corresponds to the chain length of the polymer. In this example, chitosan of molecular weight 50 KDa to 190 KDa was used as a parent polymer on which further chemical modifications and substitution of a hydrophilic polymer, PEG and a cell targeting/penetrating peptide (CP15) was performed. Since, each monomer of a chitosan polymer comprises of an amine group, thus larger chain length contributes to more number of amine groups. The presence of amine groups adds a positive character to the polymer, which enables it to complex a negatively charged molecule, such as siRNA. Due to the increase in the polymer chain length of chitosan as compared to the other low molecular weight chitosan (M.W. 10 KDa) used for brain study (Example I to III), it was anticipated that the nanoparticle formulation will be able to complex more siRNA. To confirm this assumption, a gel retardation assay was performed (FIG. 20) and it was observed that the nanoparticle formulation was able to complex 4 times higher amount of siRNA (8 µg/ml) than the previous formulation (2 µg/ml).

Evaluation of the ability of the receptor-targeted nanoparticles to systemically deliver siRNA at the targeted tumor site. Novel receptor-targeted nanoparticles were evaluated for their ability to deliver siRNA at the targeted tumor site through systemic route. The animals were sacrificed after 4 hours of first dose administered intra-peritoneally. The treatment formulation prepared from a chemically modified polymer, CS-PEG-CP15 was complexed with scrambled biotinylated siRNA at 0.5 mg/kg and was evaluated for its efficiency in comparison to siRNA delivered without nanoparticles. FIG. 21 represents histopathological staining from a mouse xenograft model of SW480 colon cancer. The tumor tissue having the scrambled biotinylated siRNA stained dark brown in color with VECTA™ stain elite kit, using DAB as a substrate. The results shown on FIG. 21(I) indicate that the staining was found to be approximately equal for both (a) CS-PEG-CP15-siRNA nanoparticle formulation (p=0.00043) and (b) unmodified chitosan-siRNA nanoparticle formulation (p=0.0011). The expression of (c) scrambled biotin-siRNA, delivered alone was comparatively less and was not significant, when compared to the untreated control (p=0.062) FIG. 21 (II) represents the mean percentage area analysed for intensity in triplicates from an animal tissue in each treatment, using IMAGE J™ software.

Figure 22A:
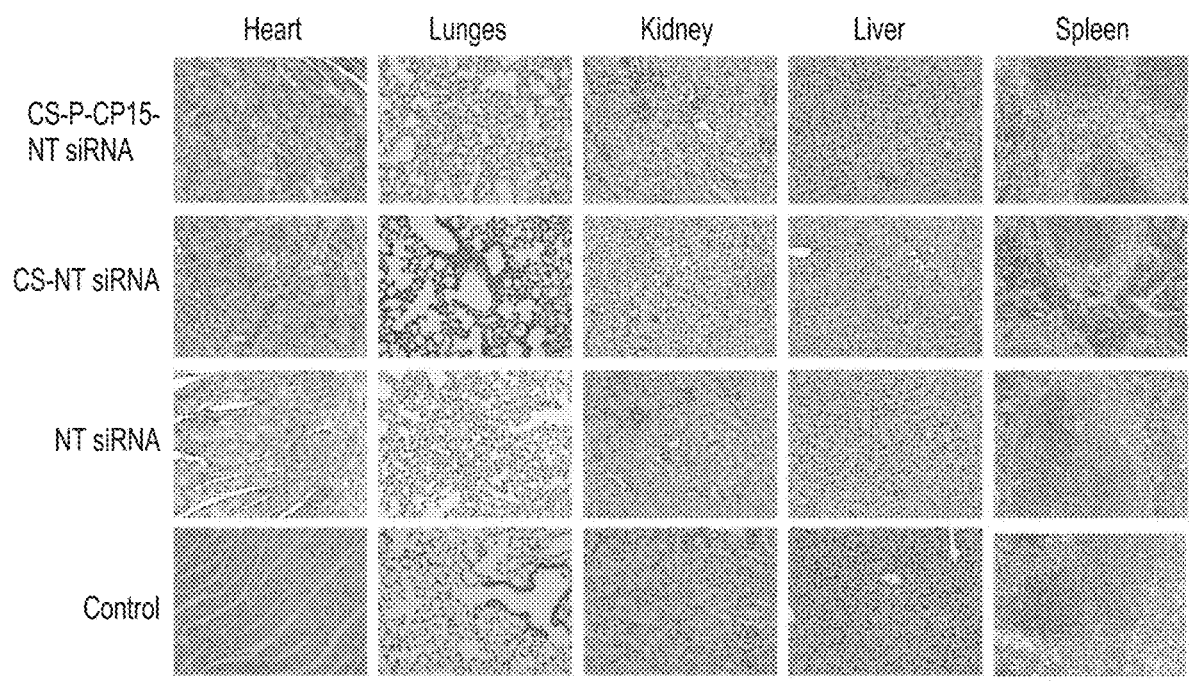
FIGS. 22A-22B represent analysis of biodistribution of siRNA in various tissues 4 hrs after the administration of various nanoparticles formulations.
Figure 22B:
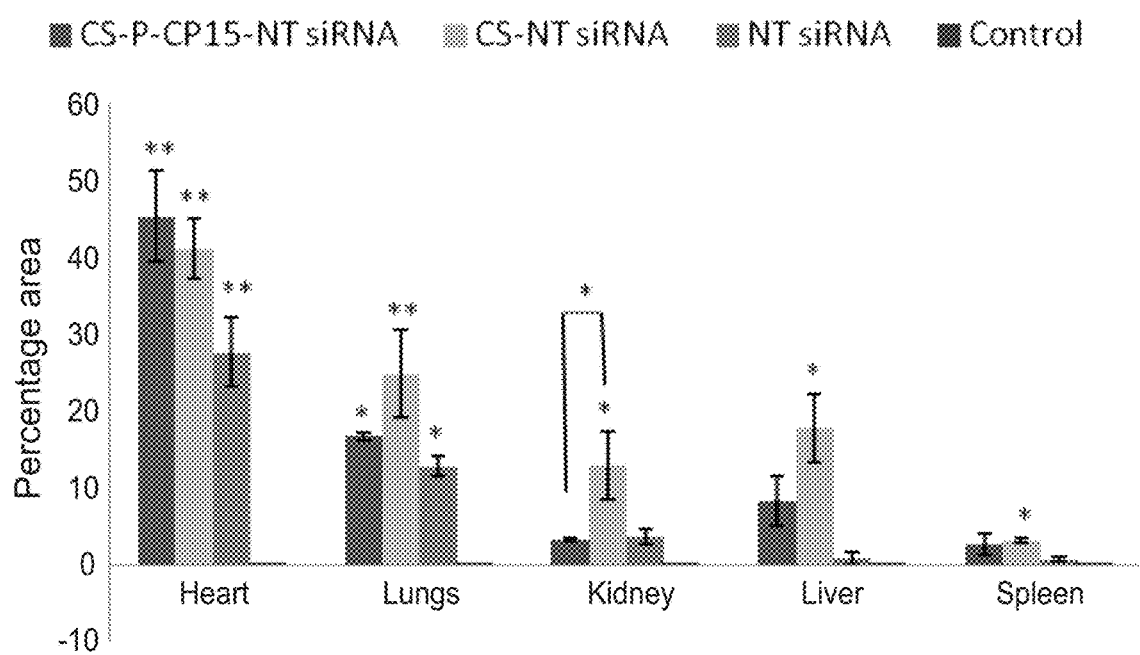

FIG. 22A represents the biodistribution analysis of the above mentioned 3 treatments in various other organs: heart, lungs, kidney, liver and spleen and were compared with the untreated control. The results indicate significant biodistribution of the unmodified chitosan nanoparticles in all the organs (p<0.05) when compared with the control. For CS-PEG-CP15 with siRNA nanoparticle formulation, the biodistribution was found to be significant only in heart (p=0.001) and lungs (p=0.017), as compared with the control. Likewise, siRNA delivered alone also showed significant expression in heart (p=0.009) and lungs (p=0.043). FIG. 22 (II) represents the mean percentage area analysed for intensity in duplicates from an animal tissue in each treatment, using IMAGE J™ software.

The tumor accumulation data as represented in FIG. 21, suggests that the derivatized chitosan nanoparticles were able to target the tumor tissue as effectively as the unmodified chitosan nanoparticles, when compared with the siRNA delivered alone and the untreated control. This data suggests that the importance and efficiency of chitosan polymer as a carrier to deliver the siRNA at the targeted site. Thus, it can be inferred that the systemic tumor targeting, could majorly be a size dependent phenomenon due to the EPR effect rather than receptor mediated targeting. However, the biodistribution study as presented in FIG. 22 showed that the CS-PEG-CP15 nanoparticles accumulated less in other organs, when compared to the unmodified chitosan nanoparticles (kidneys, p<0.046). Thus, it can be inferred that the presence of a targeting moiety on the nanoparticles restricted their uptake by other tissues [41]. The enhanced circulation and lack of accumulation in other organs of CS-PEG-CP15 nanoparticles is attributed to the incorporation of PEG, which caters to the increased stability of the nanoparticles in blood, without being degraded or filtered by kidneys. These results indicate that these nanoparticles have the ability to be administered via non-invasive routes and at the same time achieve effective tumor targeting, which in turn will reduce the off-target effects and unwanted immunological reactions and toxicity.

Figure 23:
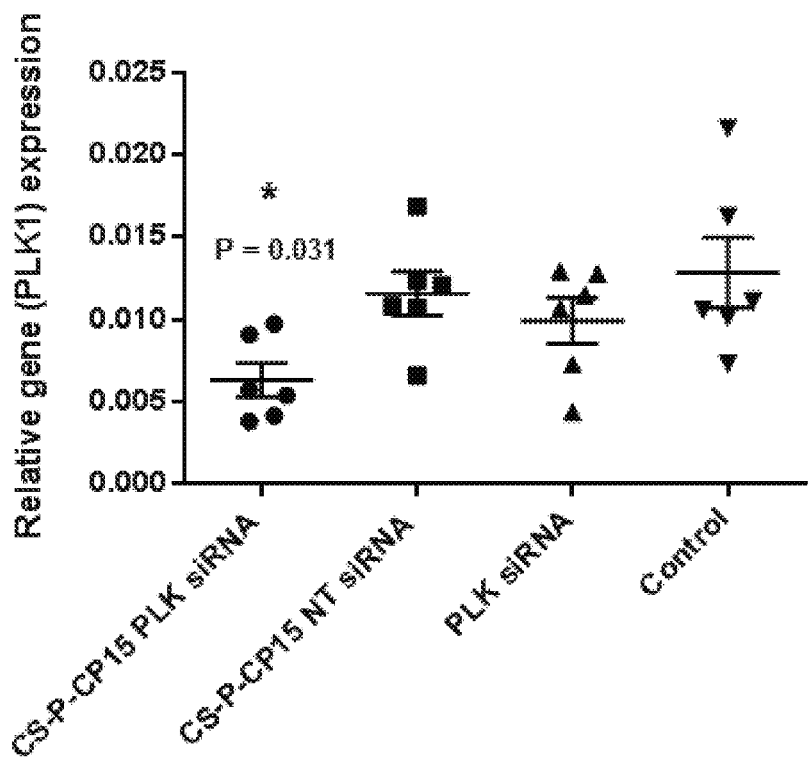
FIG. 23 shows PLK1 mRNA expression in the tumor tissue after intra-peritoneal administration with various nanoparticle formulations. Results are shown as relative gene expression of PLK1 in tumor tissues in function of nanoparticle formulation: CS-PEG-CP15-siRNA (●), CS-PEG-CP15 NT siRNA with non-targeting biotin-siRNA (■), PLK1 siRNA alone (▲) and saline (control ▼). The PLK1 gene expression was compared among different groups after normalizing the GAPDH levels among all the animals. A 50% PLK1 gene suppression was observed in treated animals (p=0.031) as compared with untreated controls. The graph shows a scatter dot plot with n=6 and mean±SE, *p<0.05 was considered significant based on Tukey's post-hoc analysis, when compared with other groups.

Evaluation of percentage gene knockdown of PLK1 gene, silenced by siRNA delivered systemically via novel receptor-targeted nanoparticles. The PLK1 gene knockdown was evaluated by extracting total RNA form the tumor tissues, then reverse transcribing it to form a cDNA and then running a Real timer PCR on cDNA using primers specific for PLK 1 gene. The percentage gene knockdown of PLK1 gene by siRNA delivered through novel receptor-targeted nanoparticles was evaluated by comparing the treatment group with other controls; mock transfections and untreated. As represented in FIG. 23, it was observed that the treatment group showed a significant reduction (P=0.031) in PLK1 gene knockdown of 50% as compared with the untreated control (n=6). There was no significant difference in the group of animals that received mock transfections i.e. nanoparticles with NT siRNA (P=0.933) and PLK1 siRNA alone (P=0.539), when compared with the untreated control. This result confirmed that the nanoparticles were able to safeguard the siRNA when administered via systemic route and delivered it specifically at the tumor site. Under these experimental conditions, the siRNA retained its functional ability of gene knockdown and was not degraded by the serum proteins.

Figure 24:
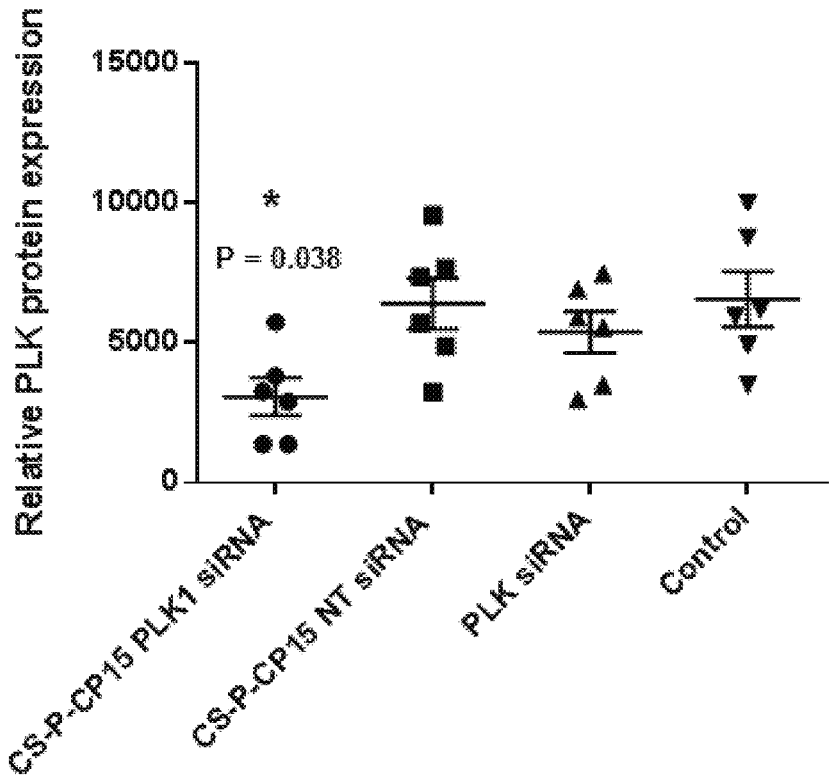
FIG. 24 shows PLK1 protein expression in the tumor tissue after intra-peritoneal administration with various nanoparticle formulations. Results are shown as relative PLK1 protein expression (obtained by western blot analysis from 100 μg of total protein extracted from tumor tissues of colon cancer and normalized against the β-actin protein levels) in function of nanoparticle formulations: CS-PEG-CP15 with siRNA against PLK1 gene (●), CS-PEG-CP15 with non-targeting biotin-siRNA (■), PLK1 siRNA alone (▲) and saline (control ▼). Reduction in PLK1 protein expression was observed with treatment formulation as compared with untreated and controls. The graph shows a scatter dot plot with n=6 and mean±SE, *P<0.05 was considered significant based on Tukey's post-hoc analysis, when compared with other groups.

Evaluation of protein suppression of PLK1 protein by siRNA, delivered systemically via novel receptor-targeted nanoparticles. To evaluate and compare the amount of protein expression in various treatment groups, the total protein was extracted from the tumor tissue, quantified using BCA assay and 100 µg of total protein was loaded onto NuPAGE® 4 to 12% Bis Tris gels for western blot analysis. The gel was electrophoretically transferred to a nitrocellulose membrane and probed with appropriate antibodies. The protein bands developed using autoluminiscence were quantified using an Image J software and plotted with animal numbers, n=6 in each group. The relative protein expression as observed in FIG. 24 shows that the animals receiving novel receptor-targeted nanoparticle formulation carrying siRNA against PLK1 gene has significantly lower protein expression (P=0.038) as compared to the control, untreated group. However, no difference was observed among the mock transfection groups i.e. nanoparticles with NT siRNA (P=0.999) and PLK1 siRNA alone (P=0.758) when compared with the control untreated group. These results suggest that the siRNA targeted against PLK1 was solely responsible for the decrease in the protein expression in the tumor tissue and there was no deleterious effect posed by the polymeric nanoparticle formulation on the tumor tissue.

Figure 25A:
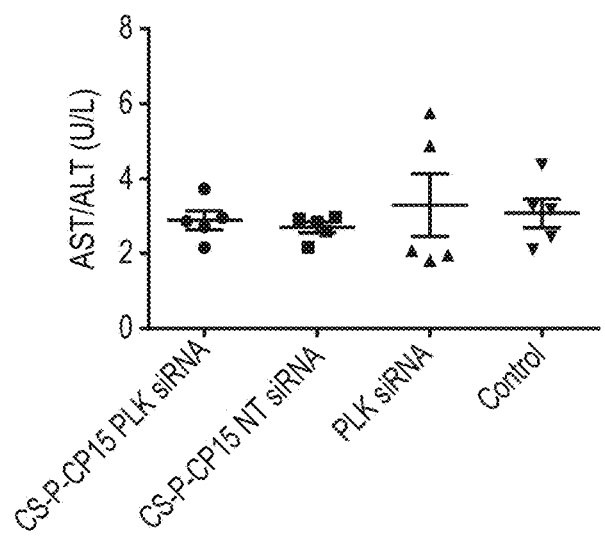
FIGS. 25A-25B show results of serum analysis of mouse treated with various nanoparticle formulations.
Figure 25B:
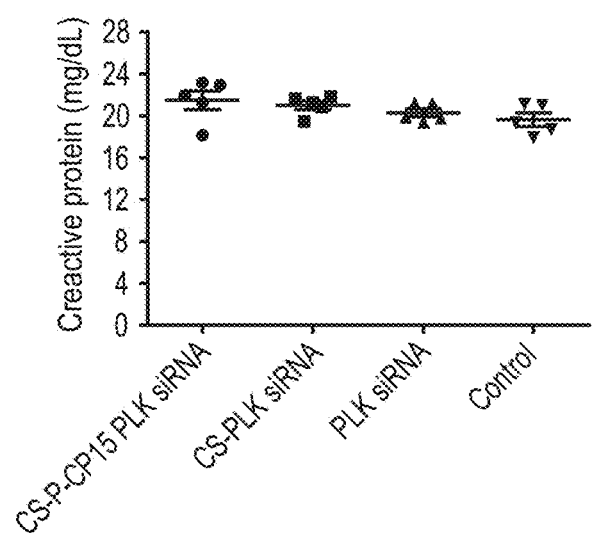

Serum analysis for safety and toxicity study. 200 µl of blood was collected in microtainer serum separating tubes just before the experimental end point, from jugular vein of all the animals in each group. The experimental end-point was at 2 weeks after the commencement of the treatment formulation. The serum was analyzed for safety tests especially for liver function tests (AST/ALT) and C-reactive proteins (CRP) as represented in FIGS. 25A and 25B respectively. No significant difference was observed among any treatment groups when compared to the untreated control for both CRP and AST/ALT ratios. Thus, these results indicate that the receptor-targeted nanoparticle formulation was not toxic and does not stimulate immunological reactions. It also shows that the percentage gene knockdown and protein suppression as observed in FIGS. 23 and 24 is the result of gene knockdown mediated by the siRNA targeted against PLK1 gene leading to cell apoptosis and was not due to any deleterious/toxic effects of the polymeric nanoparticle formulation used as a transfection reagent.

The results presented herein show the potential of novel receptor-targeted nanoparticle formulation to be used in vivo in a mouse xenograft model of colon cancer. These nanoparticles prepared from a chemically modified polymer have the ability to be modified by incorporation of a specific peptide or a cell targeting ligand/moiety, which can target a specific receptor on a cell. The nanoparticles prepared showed efficient siRNA complexation and delivery with approximately 100% transfection efficiency. The nanoparticles safe guarded the siRNA when administered systemically and specifically released it at the tumor site. 50% of gene knockdown of PLK1 was achieved as determined by qPCR analysis with siRNA delivered through novel receptor-targeted nanoparticles. These nanoparticles did not induce any immunological reactions and liver toxicity as determined by the serum analysis. This study proves that nanoparticles mediated gene therapy can be achieved and performed via non-invasive strategies. These nanoparticles as a delivery device can further be explored towards different applications such as cancer and neurological disorders. This study can further be improved by prolonging the treatment duration and increasing animal number per group in order to achieve a significant difference and refined interpretation of the data.

Example VI—Subject Study for Treating Cancer

Overexpression of Plk1 has been observed in a number of human cancers including non-small-cell lung cancer, head and neck cancer, esophageal cancer, gastric cancer, melanomas, breast cancer, ovarian cancer, endometrial cancer, colorectal cancer, glioma, papillary carcinoma, pancreatic cancer, prostate cancer, hepatoma, leukemia and lymphoma, bladder cancer, and thyroid cancer. Many of these studies have demonstrated that Plk1 overexpression correlates with tumor progression and patient survival rate in a variety of cancers. Therefore, Plk1 is proposed as a prognostic marker for human cancers.

A subject study was performed on a patient with Stage IV head and neck cancer. For this study, the synthesis of polymer was scaled up to obtain 2 g of synthesized polymer, which was used to form siRNA nanoparticles for the treatment of cancer. The siRNA used was against PLK1 mRNA, which is a proto-oncogene. The therapy was termed "Nora-PLK1".

The scaling up procedure to synthesize the polymer was performed under aseptic conditions following Good Laboratory Practices (GLP). Following is the Standard Operating Procedure (SOP) as detailed herein,
1) 4 g of Chitosan LMW with 11.04 g of phthalic anhydride in 80 ml of DMF. Stirred for 8 hrs at 110° C. under $N_2$ atmosphere. Precipitate it in ice cold water and give a methanol wash overnight. Vacuum filter next morning using a whatman filter paper on a funnel and vacuum dry. The polymer will appear light brown in color). Product "c" in FIG. 1. (Phthalic anhydride should be 3 times mole excess of chitosan)

2) 60 g of PEG (M.W. 2000) dissolved in 200 ml toluene with 12 g of succinic anhydride dissolved in 40 ml of pyridine. Stir and reflux the reaction at 100° C. for 6 hrs. Precipitate with diethyl ether and vacuum filter using a whatman filter paper on a funnel. Dissolve the product back with chloroform and again precipitate with diethylether, followed by vacuum filter on a whatman filter paper using a funnel. Repeat this process twice. At the end vacuum dry the product. (The product will appear white in color). Product "a" in FIG. 1. (Succinic anhydride should be 4M excess of PEG). (Note: Repeat this step in batches for scale up if required).

3) To the dried PEG from step 2, dissolve it in 200 ml of toluene and add equimolar of thionyl chloride. Stir and reflux the reaction at 100° C. for 6 hrs, followed by degassing to remove excess $SO_2$ and thionyl chloride. Product "b" in FIG. 1.

4) After 6 hrs, from step 3, bring down the reaction to room temperature (RT) and add phthaloyl chitosan from step 1 (pre dissolved overnight in pyridine). 1.8 g of chitosan (pre-dissolved in 50 ml of pyridine) was reacted with 60 g of PEG2000 (predissolved in 200 ml of toluene). (As the chitosan (dissolved in pyridine) is added to the PEG (toluene) solution. The reaction will look heterogeneous).

5) Let the reaction continue for 2 hrs at RT and then reflux at 100° C. for 24 hrs. After 24 hrs, bring the reaction down to RT and precipitate in methanol and vacuum filter dry on a whatman filter paper using funnel. (The product will appear pale brown in color). Product "d" in FIG. 1. (PEG2000 should be 10M excess of phthaloyl chitosan).

6) The filtered product from step 4, mix 3 g of PEGylated phthaloyl chitosan with 174 mg of Aluminum chloride in 80 ml of ethanethiol. Let the reaction stir at 23-25° C. for 12 hrs. After the reaction, dilute it with water and acidify with 10% HCl. Vacuum Filter the product on a whatman filter paper using funnel. Mix the resultant product with deionized water transfer it to a separating funnel. Extract the purified product in the separating funnel using dichloromethane three times. Rotavap the dichloromethane and obtain the dried product. (The product will appear brown and sticky). Product "e" in FIG. 1

7) To the dried product from step 5, 2.6 g of PEGylated chitosan was dissolved in 100 ml of toluene and mixed with 452.35 mg of succinic anhydride (predissolved in 5 ml of pyridine). The reaction is stirred at 100° C. for 12 hrs. After the reaction the product brought down to RT and is precipitated in methanol and vacuum filtered (whatman paper and funnel) and vacuum dry. (The polymer will appear dark brown solid in color). Product "f" in FIG. 1. (Succinic anhydride should be 4M excess of PEGylated chitosan).

8) Take 1 g of the dried CS-PEG-COOH from step 6 and dissolve it in 25 ml of DMF. Add 1.3 mole equivalent of EDC.HCl to it (87.5 mg) and 0.1 mole equivalent of DMAP (5.3 mg). Dissolve 500 mg of TAT peptide in 5 ml of DMF and add it to the above mixture. Stir it for 24 hrs at room temperature. Precipitate the mixture in ice cold water and filter (whatman paper and funnel), give the filtrate a brief wash in methanol and again filter dry it. (The product will appear brown in color). Product "g" in FIG. 1.

9) Take 1 g of the dried product from step 7 and dissolve it in 20 ml of DMF and dissolve at 80° C. under inert conditions, after that add 2.6 ml of hydrazine monohydrate to it and let the reaction stir at similar conditions for 2 hrs. (The product will appear pale yellow-white in color). Product "h" in FIG. 1. Bring the reaction to room temperature and Dialyze the product using slide-a-lyzer (dialysis tube) MW cut off of 3,500 for 2-3 days in sterilized water. While doing dialysis change the water at least 3-4 times a day. After dialysis, concentrate the product to remove excess water by vacuum filter (whatman paper and funnel) and/or freeze dry the sample, overnight and you will obtain an off-white colored fluffy polymer.

10) To prepare Nora-PLK1 nanoparticles, dissolve the synthesized Lyophilized polymer at a concentration of (0.5 mg/ml) in a sterilized water, containing 2% acetic acid and adjust the pH to 5 using 5M NaOH solution. Stir this solution overnight at 50° C. Filter the polymer solution using sterile STERICUPS™ (filters) with pore size of 0.2 μm.

11) Mix 2 μg of siRNA (20 μM siRNA stock) to the polymer (0.5 mg/ml) solution. [To prepare a dose of 50 μg of siRNA. Aliquout 25 ml of filtered chitosan polymer solution in a falcon tube and add 195 μl of (20 μM siRNA stock) and vortex vigorously for 5-10 seconds and keep at bench for 30 minutes for complexation and stabilization.

12) The nanoparticles after complexation with siRNA, be filtered through a sterile 0.45 μm filters. The sterile filtered nanoparticles should be concentrated using Am icon centrifugal concentrators (MW. Cut-off of 30,000) and spun down at 4000 rpm for 30-40 minutes to obtain a concentrate of 1.5 to 2 ml volume. (While concentrating care must be taken that the nanoparticles do not precipitate or aggregate)..

13) For freeze-drying, the concentrated siRNA-nanoparticles should be transferred to autoclaved eppendorf tubes and 300 μl of 60% sucrose solution should be added. The concentrated siRNA-nanoparticle solution, containing sucrose should be stored in −20° C. for 30 minutes, followed by freezing in −80° C. for 1-2 hrs and be placed in a lyophilizer for overnight drying. After lyophilisation, the siRNA-nanoparticle material can be stored at −80° C. until use or can be reconstituted in sterilized water up to 0.5 to 1 ml for delivery (intra tumor or intra venous) purposes.

14) The synthesis proved to be reproducible after being scaled up. The average nanoparticle size was <200 nm with a zeta potential of 16-20 mV.

The subject study was performed on female, aged 55 years old. The patient had Stage IV head and neck cancer, specifically called squamous cell carcinoma of tonsil. The patient had sub-mandibular lymph node metastasis and smaller in the right neck. There are 3 small metastasis in as many left ribs and multiple lung metastasis in both lungs. The patient had no prior treatment with chemo or radio therapy. The major outcome of the study was based on the reduction in the size of the tumors based on the CT scans. The intervention used for this study included TAT peptide-tagged PEGylated chitosan nanoparticle carrying PLK1 siRNA, termed as "Nora-PLK1" therapy.

The intervention included a total dose of 100 μg (siRNA) of Nora-PLK1 therapy, administered locally via intra-tumoral injections at alternate sites in the neck and tongue and/or via inhalation using a nebulizer/inhaler to reach lungs. The Nora-PLK1 therapy was initiated on Sep. 28, 2014 and was given for a total of 6 weeks, everyday excluding weekends.

Figure 26A:
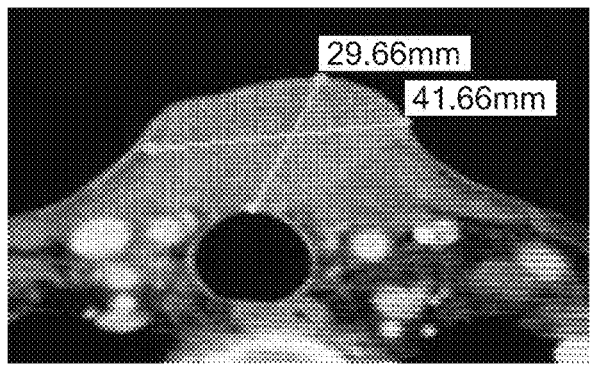
FIGS. 26A-26B show a CT scan of the neck before (FIG. 26A) and after (FIG. 26B) the 10 day therapy cycle of Nora-PLK1 therapy (intra-tumor), initiated on Sep. 27, 2014. The CT obtained on Oct. 13, 2014 shows a dramatic reduction of the tumor mass. Volumetrically the tumor reduced from 29.66×41.66×46 mm to 18.66×35.55×41 mm or from 56,839.2 $mm^3$ to 27,197.8 $mm^3$ (a 46% reduction).
Figure 26B:
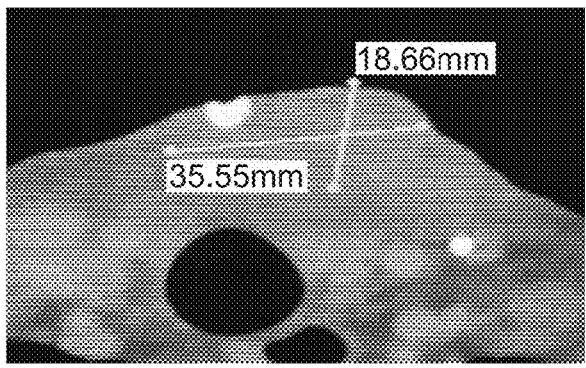
Figure 27A:
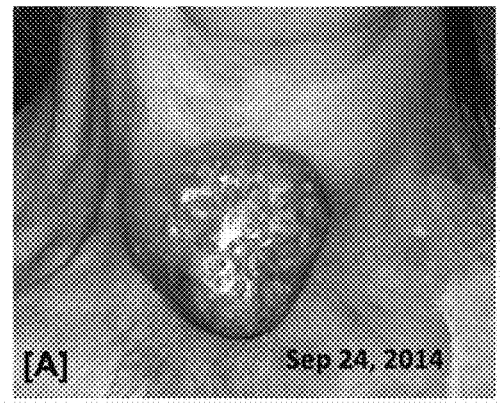
FIGS. 27A-27D show photographic evidence of the reduction of stage IV, squamous cell carcinoma (head and neck cancer) with the Nora-PLK1 therapy (nanoparticle-siRNA), administered directly into the tumor of a 55 years old, female patient. The dose administered was 100 μg of siRNA/day.
Figure 27B:
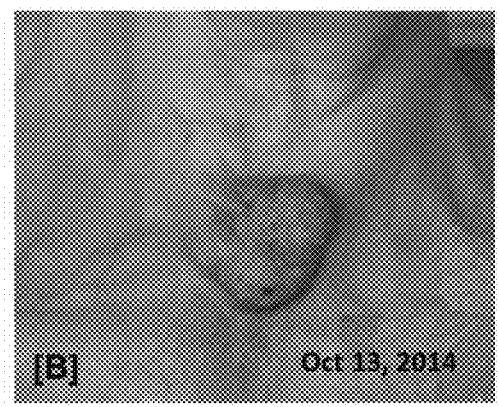
Figure 27C:
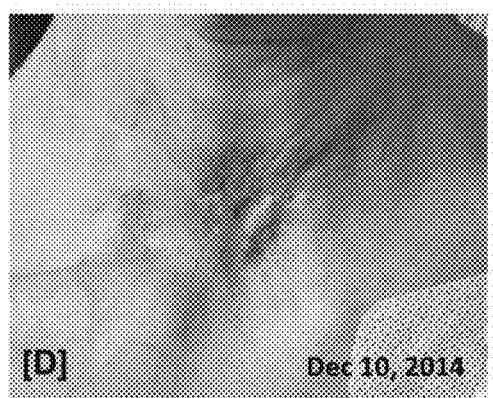
Figure 27D:
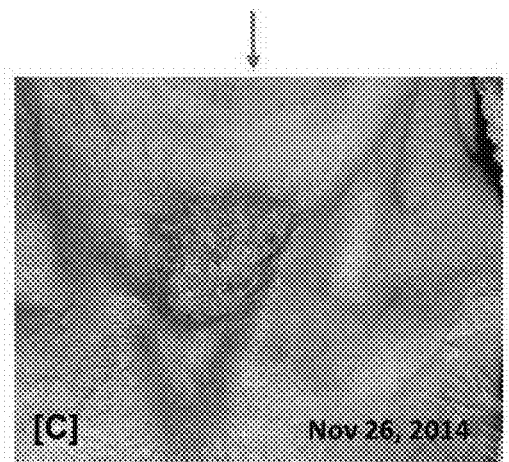

The intratumoral application resulted in a dramatic reduction of the tumor mass. Volumetrically the tumor reduced from 29.66×41.66×46 mm to 18.66×35.55×41 mm or from 56,839.2 m$^3$ to 27,197.8 m$^3$ (a 46% reduction) for the first 10 day therapy cycle of the Nora-PLK1 treatment (FIG. 26 and FIG. 27). Followed by complete disappearance of tumor mass by December 2014.

Figure 28A:
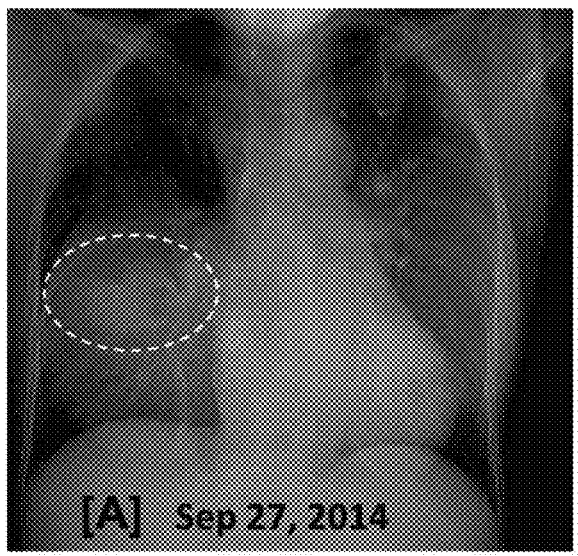
FIGS. 28A-28B show a chest CT scan of a 55 year old female patient.
Figure 28B:
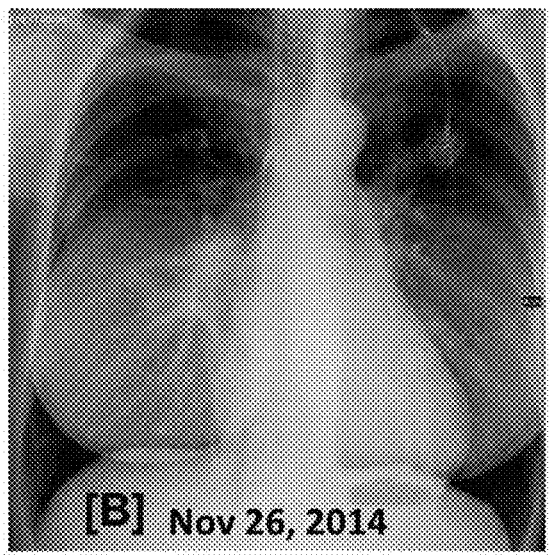

Complete disappearance of the tumor mass from lungs was observed (CT scans) with Nora-PLK1 therapy administered via inhalation using a nebulizer (FIG. 28).

The successful results obtained from the subject study showed, improved health benefits such as, disappearance of cancer from neck and lungs, improved speech, ability to eat and swallow food, gain in body-weight. The therapy worked without the need of any invasive techniques such as surgery or radio/chemotherapy. The present invention represents a platform technology, wherein the peptide used in the polymeric synthesis can be replaced with any other cell-targeting peptide, protein, antibiotic, antibody, pharmaceutical compounds. The therapeutic payload, complexed with the nanoparticle is not limited to siRNA, but can include, pDNA, miRNA, small oligonucleotides, chemotherapeutic drugs, nutraceutical compounds. The nanoparticles produced can also be formulated in a hydrogel for topical application purposes, or mixed with microparticles for oral delivery purposes to provide a varied range of its health beneficial effects.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

REFERENCES

Calvo, P, Remunan-Lopez, C, Vila-Jato, J L, Alonso, M J: Novel hydrophilic chitosan-polyethylene oxide nanoparticles as protein carriers. J Appl Polym Sci 63:125-132, 1997.

Kurita K, Ikeda H, Yoshida Y, Shimojoh M, Harata M: Chemoselective protection of the amino groups of chitosan by controlled phthaloylation: facile preparation of a precursor useful for chemical modifications. Biomacromolecules 3:1-4, 2002.

Lin W J, Chen M H: Synthesis of multifunctional chitosan with galactose as a targeting ligand for glycoprotein receptor. Carbohydrate polymers 67:474-480, 2007.

Malhotra, M, Kulamarva, A, Sebak, S, Paul, A, Bhathena, J, Mirzaei, M, Prakash, S: Ultrafine chitosan nanoparticles as an efficient nucleic acid delivery system targeting neuronal cells. Drug Development and Industrial Pharmacy 35:719-726, 2009.

What is claimed is:

1. A method for in vivo targeted delivery of a nucleic acid or an anionic agent to an individual in need thereof, said method comprising:

(a) providing a polymeric delivery system comprising the nucleic acid or the anionic agent,
   wherein the polymeric delivery system comprises non-viral nanoparticles comprising: a plurality of cationic chitosan polymers, polyethylene glycol and a peptide sequence,
   and wherein the non-viral nanoparticles comprise an internal core and the nucleic acid or the anionic agent are placed in the inner core,
   and wherein the peptide sequence comprises a cell penetrating peptide, a protein transduction domain, and a cell surface receptor targeting moiety,
   and the polymeric delivery system is made by a method comprising:
   a) reacting amine groups of chitosan with phthalic anhydride as a protection step;
   b) activating monomethoxy polyethylene glycol (mPEG-OH) with succinic anhydride to form mPEG-COOH;
   c) activating mPEG-COOH with thionyl chloride to form mPEG-COCl to form an activated PEG;
   d) reacting hydroxyl groups of chitosan with the activated mPEG-COCl to form PEGylated chitosan;
   e) reacting the monomethoxy group of the PEGylated chitosan with aluminum chloride in ethane thiol to convert the monomethoxy group to a hydroxyl group to form hydroxyl terminated PEGylated chitosan;
   f) reacting the hydroxyl terminated PEGylated chitosan with succinic anhydride to form an activated chitosan-PEG-COOH;
   g) reacting the activated chitosan-PEG-COOH with a peptide sequence comprising a cell penetrating peptide, a protein transduction domain, and a cell surface receptor targeting moiety, wherein said peptide sequence comprises a terminal amine, and wherein this reaction is done using EDC and DMAP as a catalyst to form chitosan-PEG-peptide; and
   h) reacting the chitosan-PEG-peptide with hydrazine monohydrate to deprotect amine groups of chitosan,
   and wherein the plurality of cationic chitosan polymers are cross linked to each other to form the outer layer of the nanoparticle to generate an internal core;
   and the nanoparticles have an average diameter of between 5 to 300 nm; and (b) administering the non-viral nanoparticle to the individual.

2. The method of claim 1, wherein the nucleic acid or anionic agent is delivered to the individual in need thereof to treat a disease or a condition.

3. The method of claim 2, wherein the disease or condition is a cancer or a neurodegenerative disease.

4. The method of claim 3, wherein the cancer is a brain cancer or colon cancer.

5. The method of claim 1, wherein the nucleic acid is a siRNA.

6. The method of claim 5, wherein the siRNA is a Plk1-targeting siRNA.

7. The method of claim 1, wherein the nanoparticles have an average diameter of between 100 nm to 200 nm.

8. The method of claim 1, wherein the average molecular weight of the cationic chitosan polymers is from about 50 kDa to about 200 kDa.

9. The method of claim 1, wherein the degree of deacetylation of the cationic chitosan polymers is about 80%.

10. The method of claim 1, wherein the nanoparticles have an average diameter of less than 20 nm.

11. The method of claim 1, wherein the nanoparticles are formulated for intranasal administration and the administration is intranasal.

12. The method of claim 1, wherein the nanoparticles are formulated for intravenous administration and the administration is intravenous.

13. The method of claim 1, wherein the non-viral nanoparticle is formulated for intratumoral administration and the administration is intratumoral.

* * * * *

SEQUENCE LISTING

```
<160> NUMBER OF SEQ ID NOS: 16

<210> SEQ ID NO 1
<211> LENGTH: 24
<212> TYPE: PRT
<213> ORGANISM: Artificial Sequence
<220> FEATURE:
<223> OTHER INFORMATION: MGF peptide

<400> SEQUENCE: 1

Tyr Gln Pro Pro Ser Thr Asn Lys Asn Thr Lys Ser Gln Arg Arg Lys
1               5                   10                  15

Gly Ser Thr Phe Glu Glu His Lys
            20

<210> SEQ ID NO 2
<211> LENGTH: 7
<212> TYPE: PRT
<213> ORGANISM: Artificial Sequence
<220> FEATURE:
<223> OTHER INFORMATION: CP15 peptide

<400> SEQUENCE: 2

Val His Leu Gly Tyr Ala Thr
1               5

<210> SEQ ID NO 3
<211> LENGTH: 12
<212> TYPE: PRT
<213> ORGANISM: Artificial Sequence
<220> FEATURE:
<223> OTHER INFORMATION: P160 peptide

<400> SEQUENCE: 3
```

```
Val Pro Trp Met Glu Pro Ala Tyr Gln Arg Phe Leu
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: TAT peptide

<400> SEQUENCE: 4

```
Arg Lys Lys Arg Arg Gln Arg Arg Arg
1               5
```

<210> SEQ ID NO 5
<211> LENGTH: 21
<212> TYPE: RNA
<213> ORGANISM: Artificial Sequence
<220> FEATURE:
<223> OTHER INFORMATION: PSN1 siRNA

<400> SEQUENCE: 5
aagguccacu ucguaugcug g                                         21

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide

<400> SEQUENCE: 6
ccgaaatcac agccaaga                                             18

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
cattcacaga agataccaag ac                                        22

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide

<400> SEQUENCE: 8
taaagggcat cctgggctac act                                       23

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide

<400> SEQUENCE: 9
ttactccttg gaggccatgt agg                                       23

<210> SEQ ID NO 10
<211> LENGTH: 21

```
<212> TYPE: RNA
<213> ORGANISM: Artificial Sequence
<220> FEATURE:
<223> OTHER INFORMATION: PLK siRNA sense
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (18)..(18)
<223> OTHER INFORMATION: um

<400> SEQUENCE: 10
agaucacccu ccuuaaauau u                                    21

<210> SEQ ID NO 11
<211> LENGTH: 21
<212> TYPE: RNA
<213> ORGANISM: Artificial Sequence
<220> FEATURE:
<223> OTHER INFORMATION: PLK siRNA antisense
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (17)..(17)
<223> OTHER INFORMATION: um

<400> SEQUENCE: 11
uauuuaagga gggugaucuu u                                    21

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
ggcaaccttt tcctgaatga                                      20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
aatggaccac acatccacct                                      20

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide

<400> SEQUENCE: 14
```

```
taaagggcat cctgggctac act                                              23

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

<400> SEQUENCE: 15
ttactccttg gaggccatgt agg                                              23

<210> SEQ ID NO 16
<211> LENGTH: 11
<212> TYPE: PRT
<213> ORGANISM: Artificial Sequence
<220> FEATURE:
<223> OTHER INFORMATION: synthetic peptide

<400> SEQUENCE: 16

Lys Lys Leu Val Pro Pro Ala Glu Lys Gly Cys
1               5                   10
```